US011827886B2

(12) United States Patent
Brown, Jr. et al.

(10) Patent No.: US 11,827,886 B2
(45) Date of Patent: Nov. 28, 2023

(54) COMPOSITIONS AND METHODS FOR MODULATING DYSFERLIN EXPRESSION

(71) Applicant: University of Massachusetts, Boston, MA (US)

(72) Inventors: Robert H. Brown, Jr., Needham, MA (US); Janice A. Dominov, North Reading, MA (US)

(73) Assignee: University of Massachusetts, Boston, MA (US)

(*) Notice: Subject to any disclaimer, the term of this patent is extended or adjusted under 35 U.S.C. 154(b) by 447 days.

(21) Appl. No.: 16/872,448

(22) Filed: May 12, 2020

(65) Prior Publication Data

US 2020/0339999 A1    Oct. 29, 2020

Related U.S. Application Data

(63) Continuation of application No. 15/316,027, filed as application No. PCT/US2015/033973 on Jun. 3, 2015, now Pat. No. 10,689,653.

(60) Provisional application No. 62/007,397, filed on Jun. 3, 2014.

(51) Int. Cl.
| | |
|---|---|
| *C12N 15/113* | (2010.01) |
| *C12Q 1/6883* | (2018.01) |
| *C07K 16/18* | (2006.01) |
| *C12N 15/86* | (2006.01) |
| *G01N 33/68* | (2006.01) |

(52) U.S. Cl.
CPC .......... *C12N 15/1138* (2013.01); *C07K 16/18* (2013.01); *C12N 15/86* (2013.01); *C12Q 1/6883* (2013.01); *G01N 33/6872* (2013.01); *C07K 2317/34* (2013.01); *C12N 2310/11* (2013.01); *C12N 2320/33* (2013.01); *C12N 2320/53* (2013.01); *C12N 2750/14143* (2013.01); *C12Q 2600/156* (2013.01); *G01N 2333/705* (2013.01); *G01N 2800/2878* (2013.01)

(58) Field of Classification Search
None
See application file for complete search history.

(56) References Cited

U.S. PATENT DOCUMENTS

| | | | |
|---|---|---|---|
| 5,470,967 A | 11/1995 | Huie et al. | |
| 5,478,745 A | 12/1995 | Samulski et al. | |
| 5,871,982 A | 2/1999 | Wilson et al. | |
| 6,251,677 B1 | 6/2001 | Wilson et al. | |
| 6,485,966 B2 | 11/2002 | Gao et al. | |
| 6,544,786 B1 | 4/2003 | Xiao et al. | |
| 6,673,909 B1 | 1/2004 | Brown et al. | |
| 6,953,690 B1 | 10/2005 | Gao et al. | |
| 7,022,519 B2 | 4/2006 | Gao et al. | |
| 7,235,393 B2 | 6/2007 | Gao et al. | |
| 7,427,396 B2 | 9/2008 | Arbetman et al. | |
| 7,456,015 B2 | 11/2008 | Bohn et al. | |
| 7,906,111 B2 | 3/2011 | Wilson et al. | |
| 8,222,221 B2 | 7/2012 | Corey et al. | |
| 8,524,446 B2 | 9/2013 | Gao et al. | |
| 8,734,809 B2 | 5/2014 | Gao et al. | |
| 9,217,155 B2 | 12/2015 | Gao et al. | |
| 9,249,424 B2 | 2/2016 | Wolf et al. | |
| 10,689,653 B2 | 6/2020 | Brown et al. | |
| 2001/0016355 A1 | 8/2001 | Samulski et al. | |
| 2002/0164783 A1 | 11/2002 | Feldhaus | |
| 2002/0192823 A1 | 12/2002 | Bartlett | |
| 2003/0103939 A1 | 6/2003 | Engelhardt et al. | |
| 2003/0110526 A1 | 6/2003 | Brown et al. | |
| 2003/0138772 A1 | 7/2003 | Gao et al. | |
| 2004/0101514 A1 | 5/2004 | Liu et al. | |
| 2004/0123343 A1 | 6/2004 | La Rosa et al. | |
| 2004/0219528 A1 | 11/2004 | Morris et al. | |
| 2005/0032219 A1 | 2/2005 | Aubourg et al. | |
| 2005/0197313 A1 | 9/2005 | Roelvink | |
| 2005/0255086 A1 | 11/2005 | Davidson et al. | |
| 2005/0255089 A1 | 11/2005 | Chiorini et al. | |
| 2006/0063174 A1 | 3/2006 | Turner et al. | |
| 2006/0093589 A1 | 5/2006 | Warrington et al. | |
| 2006/0153826 A1 | 7/2006 | Arnould et al. | |
| 2006/0189564 A1 | 8/2006 | Burright et al. | |
| 2006/0228800 A1 | 10/2006 | Lin et al. | |
| 2006/0292117 A1 | 12/2006 | Loiler et al. | |
| 2007/0036760 A1 | 2/2007 | Wilson et al. | |
| 2007/0243526 A1 | 10/2007 | Kay et al. | |
| 2007/0292410 A1 | 12/2007 | Cashman et al. | |
| 2009/0042828 A1 | 2/2009 | Xu et al. | |
| 2009/0111766 A1 | 4/2009 | Atkinson et al. | |
| 2009/0149409 A1 | 6/2009 | Bohn et al. | |
| 2009/0215879 A1 | 8/2009 | DiPrimio et al. | |

(Continued)

FOREIGN PATENT DOCUMENTS

| | | |
|---|---|---|
| EP | 2261242 A1 | 12/2010 |
| WO | WO 2003/042397 | 5/2003 |

(Continued)

OTHER PUBLICATIONS

EP 19814935.3, Sep. 16, 2022, Extended European Search Report.
PCT/US2019/036045, Dec. 17, 2020, International Preliminary Report on Patentability.
PCT/US2015/033973, Sep. 29, 2015, *International Search Report and Written Opinion.
PCT/US2015/033973, Dec. 15, 2016, *International Preliminary Report on Patentability.
PCT/US2019/036045, Nov. 5, 2019, International Search Report and Written Opinion.

(Continued)

*Primary Examiner* — Sean McGarry
(74) *Attorney, Agent, or Firm* — Wolf, Greenfield & Sacks, P.C.

(57) ABSTRACT

Aspects of the disclosure relate to methods of altering RNA splicing in a subject. In some embodiments, methods are provided for correcting splicing in a cell that contains a DYSF gene having a mutation that results in defective splicing.

15 Claims, 11 Drawing Sheets

Specification includes a Sequence Listing.

(56) References Cited

U.S. PATENT DOCUMENTS

| | | |
|---|---|---|
| 2010/0266551 A1 | 10/2010 | Richard et al. |
| 2010/0323001 A1 | 12/2010 | Pachuk |
| 2011/0171262 A1 | 7/2011 | Bakker et al. |
| 2011/0172293 A1 | 7/2011 | Fish et al. |
| 2011/0212520 A1 | 9/2011 | Davidson et al. |
| 2011/0258716 A1 | 10/2011 | Baltimore et al. |
| 2012/0077870 A1 | 3/2012 | Blanks et al. |
| 2012/0137379 A1 | 5/2012 | Gao et al. |
| 2012/0208865 A1 | 8/2012 | Levy et al. |
| 2012/0270930 A1* | 10/2012 | Van Der Maarel .. C12N 15/113 435/6.12 |
| 2012/0309050 A1 | 12/2012 | Kumon et al. |
| 2013/0030042 A1 | 1/2013 | Couto |
| 2013/0101558 A1 | 4/2013 | Gao et al. |
| 2013/0109742 A1 | 5/2013 | Hewitt et al. |
| 2013/0195801 A1 | 8/2013 | Gao et al. |
| 2013/0281516 A1 | 10/2013 | Gao et al. |
| 2013/0323226 A1 | 12/2013 | Wilson et al. |
| 2014/0142161 A1 | 5/2014 | Flotte et al. |
| 2014/0142288 A1 | 5/2014 | Davidson et al. |
| 2014/0179770 A1 | 6/2014 | Zhang et al. |
| 2014/0201857 A1 | 7/2014 | Fahrenkrug et al. |
| 2014/0296486 A1 | 10/2014 | Gao et al. |
| 2014/0335054 A1 | 11/2014 | Gao et al. |
| 2015/0065560 A1 | 3/2015 | Bjorklund et al. |
| 2016/0017005 A1 | 1/2016 | Asokan et al. |
| 2016/0208257 A1 | 1/2016 | Gao et al. |
| 2016/0060624 A1 | 3/2016 | Davidson et al. |
| 2016/0076054 A1 | 3/2016 | Auricchio et al. |
| 2016/0135438 A1 | 5/2016 | Gao et al. |
| 2016/0153005 A1 | 6/2016 | Zhang et al. |
| 2016/0185832 A1 | 6/2016 | Drivas et al. |
| 2016/0186211 A1 | 6/2016 | Flotte et al. |
| 2016/0194374 A1 | 7/2016 | Wijnholds et al. |
| 2016/0272976 A1 | 9/2016 | Kaspar |
| 2017/0029785 A1 | 2/2017 | Zhao et al. |
| 2017/0101645 A1 | 4/2017 | Brown et al. |
| 2017/0114340 A1 | 4/2017 | Mueller et al. |
| 2017/0165377 A1 | 6/2017 | Gao et al. |
| 2021/0246443 A1 | 8/2021 | Brown et al. |

FOREIGN PATENT DOCUMENTS

| | | |
|---|---|---|
| WO | WO 2005/033321 | 4/2005 |
| WO | WO 2006/031267 A2 | 3/2006 |
| WO | WO 2006/066066 A2 | 6/2006 |
| WO | WO 2006/119432 A2 | 11/2006 |
| WO | WO 2008/125846 A2 | 10/2008 |
| WO | WO 2008/150897 A2 | 12/2008 |
| WO | WO 2009/043936 | 4/2009 |
| WO | WO 2009/146178 A1 | 12/2009 |
| WO | WO 2010/071454 A1 | 6/2010 |
| WO | WO 2010/099383 A2 | 9/2010 |
| WO | WO 2010/129021 A1 | 11/2010 |
| WO | WO 2010/138263 A2 | 12/2010 |
| WO | WO 2011/094198 A1 | 8/2011 |
| WO | WO 2013/055865 A1 | 4/2013 |
| WO | WO 2013/123503 A1 | 8/2013 |
| WO | WO 2013/190059 A1 | 12/2013 |
| WO | WO 2014/160092 A1 | 10/2014 |
| WO | WO 2014/186746 A1 | 11/2014 |
| WO | WO 2015/121501 A1 | 8/2015 |
| WO | WO 2015/164786 A1 | 10/2015 |
| WO | WO 2015/168666 A2 | 11/2015 |
| WO | WO 2015/187825 A2 | 12/2015 |
| WO | WO 2016/054615 A2 | 4/2016 |
| WO | WO 2016/065001 A1 | 4/2016 |
| WO | WO 2017/023724 A1 | 2/2017 |
| WO | WO 2017/106292 A1 | 6/2017 |

OTHER PUBLICATIONS

International Search Report and Written Opinion for Application No. PCT/US2019/036045, dated Nov. 5, 2019.

Uniprot Submission; Accession No. A8IGP7; Nov. 13, 2013.

Uniprot Submission; Accession No. T2BRA8; Nov. 13, 2013.

Uniprot Submission; Accession No. H3GK32; Feb. 6, 2013.

Aartsma-Rus et al., New insights in gene-derived therapy: the example of Duchenne muscular dystrophy. Ann N Y Acad Sci. Dec. 2010;1214:199-212. doi: 10.1111/j.1749-6632.2010.05836.x. Epub Dec. 1, 2010.

Alisky et al., Gene therapy for amyotrophic lateral sclerosis and other motor neuron diseases. Hum Gene Ther. Nov. 20, 2000;11(17):2315-29.

Arbuthnot et al., Hepatic delivery of RNA interference activators for therapeutic application. Curr Gene Ther. Apr. 2009;9(2):91-103.

Asokan et al., The AAV vector toolkit: poised at the clinical crossroads. Mol Ther. Apr. 2012;20(4):699-708. doi: 10.1038/mt.2011.287. Epub Jan. 24, 2012.

Azzouz et al., VEGF delivery with retrogradely transported lentivector prolongs survival in a mouse ALS model. Nature. May 27, 2004;429(6990):413-7.

Baek et al., AAV-mediated gene delivery in adult GM1-gangliosidosis mice corrects lysosomal storage in CNS and improves survival. PLoS One. Oct. 18, 2010;5(10):e13468. doi: 10.1371/journal.pone.0013468.

Berns et al., Biology of adeno-associated virus. Curr Top Microbiol Immunol. 1996;218:1-23.

Beutler et al., AAV for pain: steps towards clinical translation. Gene Ther. Apr. 2009;16(4):461-9. Epub Mar. 5, 2009.

Boillée et al., Onset and progression in inherited ALS determined by motor neurons and microglia. Science. Jun. 2, 2006;312(5778):1389-92.

Bourdenx et al., Systemic gene delivery to the central nervous system using Adeno-associated virus. Front Mol Neurosci. Jun. 2, 2014;7:50. doi: 10.3389/fnmol.2014.00050. eCollection 2014.

Buning et al., Receptor targeting of adeno-associated virus vectors. Gene Ther. Jul. 2003;10(14):1142-51.

Calcedo et al., Worldwide epidemiology of neutralizing antibodies to adeno-associated viruses. J Infect Dis. Feb. 1, 2009;199(3):381-90.

Carter et al., Adeno-associated virus gene expression and regulation. CRC Handbook of parvoviruses. 1990:227-54.

Carter, in "Handbook of Parvoviruses", ed., P. Tijsser, CRC Press, pp. 155-168 (1990).

Cearley et al., Expanded repertoire of AAV vector serotypes mediate unique patterns of transduction in mouse brain. Mol Ther. Oct. 2008;16(10):1710-8. doi: 10.1038/mt.2008.166. Epub Aug. 19, 2008.

Chadderton et al., Improved retinal function in a mouse model of dominant retinitis pigmentosa following AAV-delivered gene therapy. Mol Ther. Apr. 2009;17(4):593-9. Epub Jan. 27, 2009.

Chen et al., Molecular signatures of disease brain endothelia provide new sites for CNS-directed enzyme therapy. Nat Med. Oct. 2009;15(10):1215-8. doi: 10.1038/nm.2025. Epub Sep. 13, 2009.

Cheng et al., Development of optimized AAV3 serotype vectors: mechanism of high-efficiency transduction of human liver cancer cells. Gene Ther. Apr. 2012;19(4):375-84. doi: 10.1038/gt.2011.105. Epub Jul. 21, 2011.

Chiorini et al., Cloning and characterization of adeno-associated virus type 5. J Virol. Feb. 1999;73(2):1309-19.

Choudhury et al., Identification of Novel vectors capable of CNS transduction in adult mice after single round selection using DNA shuffled AAV capsid library. Mol Ther. May 1, 2013;21(1):S1.

Conlon et al., Ribozyme Approaches towards Down-Regulation of Pi*Z Mutant Human a-1 Anti-Trypsin. Mol. Therapy. 2004;9:S333. Abstract 875.

Cruz et al., The promise of gene therapy for the treatment of alpha-1 antitrypsin deficiency. Pharmacogenomics. Sep. 2007;8(9):1191-8.

Davidoff et al., Sex significantly influences transduction of murine liver by recombinant adeno-associated viral vectors through an androgen-dependent pathway. Blood. Jul. 15, 2003;102(2):480-8. Epub Mar. 13, 2003.

Daya et al., Gene therapy using adeno-associated virus vectors. Clin Microbiol Rev. Oct. 2008;21(4):583-93. doi: 10.1128/CMR.00008-08.

(56) References Cited

OTHER PUBLICATIONS

Di Giorgio et al., Non-cell autonomous effect of glia on motor neurons in an embryonic stem cell-based ALS model. Nat Neurosci. May 2007;10(5):608-14. Epub Apr. 15, 2007.
Dominov et al., A novel dysferlin mutant pseudoexon bypassed with antisense oligonucleotides. Ann Clin Transl Neurol. Sep. 2014;1(9):703-20. doi: 10.1002/acn3.96. Epub Sep. 27, 2014.
Duque et al., Intravenous administration of self-complementary AAV9 enables transgene delivery to adult motor neurons. Mol Ther. Jul. 2009;17(7):1187-96. doi: 10.1038/mt.2009.71. Epub Apr. 14, 2009.
Eberling et al., Results from a phase I safety trial of hAADC gene therapy for Parkinson disease. Neurology. May 20, 2008;70(21):1980-3. doi: 10.1212/01.wnl.0000312381.29287.ff. Epub Apr. 9, 2008.
Fechner et al., Cardiac-targeted RNA interference mediated by an AAV9 vector improves cardiac function in coxsackievirus B3 cardiomyopathy. J Mol Med (Berl). Sep. 2008;86(9):987-97. doi: 10.1007/s00109-008-0363-x. Epub Jun. 12, 2008.
Feigin et al., Modulation of metabolic brain networks after subthalamic gene therapy for Parkinson's disease. Proc Natl Acad Sci U S A. Dec. 4, 2007;104(49):19559-64. Epub Nov. 27, 2007.
Fisher et al., Transduction with recombinant adeno-associated virus for gene therapy is limited by leading-strand synthesis. J Virol. Jan. 1996;70(1):520-32.
Flotte et al., Phase I trial of intramuscular injection of a recombinant adeno-associated virus alpha 1-antitrypsin (rAAV2-CB-hAAT) gene vector to AAT-deficient adults. Hum Gene Ther. Jan. 2004;15(1):93-128.
Foust et al., Intravascular AAV9 preferentially targets neonatal-neurons and adult-astrocytes. Nature Biotechnology, 27; 59-65 2009.
Foust et al., Over the barrier and through the blood: to CNS delivery we go. Cell Cycle. Dec. 15, 2009;8(24):4017-8.
Fraldi et al., Functional correction of CNS lesions in an MPS-IIIA mouse model by intracerebral AAV-mediated delivery of sulfamidase and SUMF1 genes. Hum Mol Genet. Nov. 15, 2007;16(22):2693-702. Epub Aug. 27, 2007.
Gadalla et al., Improved survival and reduced phenotypic severity following AAV9/MECP2 gene transfer to neonatal and juvenile male Mecp2 knockout mice. Mol Ther. Jan. 2013;21(1):18-30. doi:10.1038/mt.2012.200. Epub Sep. 25, 2012.
Gao et al., Inadvertent gene transfer of co-packaged rep and cap sequences during the production of AAV vector and its potential impact on vector performance. Molecular Therapy. May 2008;16(Suppl. 1):S105-S106. Abstract 279.
Gao et al., RAAV-mediated targeting in adult mice and its potential in generating animal models of tissue-specific somatic transgenics or knock down. Molecular Therapy. May 2008;16(1):S118-S119. Abstract 316.
Grimm, Small silencing RNAs: state-of-the-art. Adv Drug Deliv Rev. Jul. 25, 2009;61(9):672-703. doi: 10.1016/j.addr.2009.05.002. Epub May 7, 2009.
Iida et al., Systemic Delivery of Tyrosine-Mutant AAV Vectors Results in Robust Transduction of Neurons in Adult Mice. BioMed Res Int. 2013;2013.
Koornneef et al., Apolipoprotein B knockdown by AAV-delivered shRNA lowers plasma cholesterol in mice. Mol Ther. Apr. 2011;19(4):731-40. doi:10.1038/mt.2011.6. Epub Feb. 8, 2011.
Jakobsson et al., Lentiviral vectors for use in the central nervous system. Mol Ther. Mar. 2006;13(3):484-93. Epub Jan. 3, 2006.
Janson et al., Clinical protocol. Gene therapy of Canavan disease: AAV-2 vector for neurosurgical delivery of aspartoacylase gene (ASPA) to the human brain. Hum Gene Ther. Jul. 20, 2002;13(11):1391-412.
Kaspar et al., Retrograde viral delivery of IGF-1 prolongs survival in a mouse ALS model. Science. Aug. 8, 2003;301(5634):839-42.
Kotin et al., Organization of adeno-associated virus DNA in latently infected Detroit 6 cells. Virology. Jun. 1989;170(2):460-7.
Kotin et al., Site-specific integration by adeno-associated virus. Proc Natl Acad Sci U S A. Mar. 1990;87(6):2211-5.

Lawlor et al., Efficient gene delivery and selective transduction of glial cells in the mammalian brain by AAV serotypes isolated from nonhuman primates. Mol Ther. Oct. 2009;17(10):1692-702. doi:10.1038/mt.2009.170.
Li et al., Efficient and Targeted Transduction of Nonhuman Primate Liver With Systemically Delivered Optimized AAV3B Vectors. Mol Ther. Dec. 2015;23(12):1867-76. doi: 10.1038/mt.2015.174. Epub Sep. 25, 2015.
Li et al., Protein trans-splicing as a means for viral vector-mediated in vivo gene therapy. Hum Gene Ther. Sep. 2008;19(9):958-64. doi: 10.1089/hum.2008.009.
Lowenstein, Crossing the rubicon. Nat Biotechnol. Jan. 2009;27(1):42-4.
Lux et al., Green fluorescent protein-tagged adeno-associated virus particles allow the study of cytosolic and nuclear trafficking. J Virol. Sep. 2005;79(18):11776-87.
Maguire et al., Gene therapy for the nervous system: challenges and new strategies. Neurotherapeutics. Oct. 2014;11(4):817-39. doi: 10.1007/s13311-014-0299-5.
Mandel et al., Recombinant adeno-associated viral vectors as therapeutic agents to treat neurological disorders. Mol Ther. Mar. 2006;13(3):463-83. Epub Jan. 18, 2006.
Matalon et al., Adeno-associated virus-mediated aspartoacylase gene transfer to the brain of knockout mouse for canavan disease. Mol Ther. May 2003;7(5 Pt 1):580-7.
McBride et al., Artificial miRNAs mitigate shRNA-mediated toxicity in the brain: implications for the therapeutic development of RNAi. Proc Natl Acad Sci U S A. Apr. 15, 2008;105(15):5868-73. Epub Apr. 8, 2008.
McCarty et al., Adeno-associated virus terminal repeat (TR) mutant generates self-complementary vectors to overcome the rate-limiting step to transduction in vivo. Gene Ther. Dec. 2003;10(26):2112-8.
McCarty et al., Integration of adeno-associated virus (AAV) and recombinant AAV vectors. Annu Rev Genet. 2004;38:819-45.
McCarty et al., Self-complementary recombinant adeno-associated virus (scAAV) vectors promote efficient transduction independently of DNA synthesis. Gene Ther. Aug. 2001;8(16):1248-54.
McCarty, Self-complementary AAV vectors; advances and applications. Mol Ther. Oct. 2008;16(10):1648-56. Epub Aug. 5, 2008.
McCurdy et al., Sustained normalization of neurological disease after intracranial gene therapy in a feline model. Sci Transl Med. Apr. 9, 2014;6(231):231ra48. doi: 10.1126/scitranslmed.3007733.
Mietzsch et al., OneBac 2.0: Sf9 Cell Lines for Production of AAV5 Vectors with Enhanced Infectivity and Minimal Encapsidation of Foreign DNA. Hum Gene Ther. Oct. 2015;26(10):688-97. doi:10.1089/hum.2015.050. Epub Aug. 6, 2015.
Mueller et al., Development of Simultaneous Gene Augmentation and Reduction of Mutant Gene Expression with a Single Recombinant AAV for Alpha-1 Antitrypsin Disease. Molecular Therapy May 2009;17(1):S391-S392. Abstract 1030.
O'Reilly et al., RNA interference-mediated suppression and replacement of human rhodopsin in vivo. Am J Hum Genet. Jul. 2007;81(1):127-35. Epub May 23, 2007.
Passini et al., CNS-targeted gene therapy improves survival and motor function in a mouse model of spinal muscular atrophy. J Clin Invest. Apr. 2010;120(4):1253-64. doi: 10.1172/JCI41615. Epub Mar. 15, 2010.
Ralph et al., Silencing mutant SOD1 using RNAi protects against neurodegeneration and extends survival in an ALS model. Nat Med. Apr. 2005;11(4):429-33. Epub Mar. 13, 2005.
Raoul et al., Lentiviral-mediated silencing of SOD1 through RNA interference retards disease onset and progression in a mouse model of ALS. Nat Med. Apr. 2005;11(4):423-8. Epub Mar. 13, 2005.
Schattgen et al., Cutting Edge: DNA in the Lung Microenvironment during Influenza Virus Infection Tempers Inflammation by Engaging the DNA Sensor AIM2. J Immunol. Jan. 1, 2016;196(1):29-33. doi:10.4049/jimmunol.1501048.
Schnepp et al., Characterization of adeno-associated virus genomes isolated from human tissues. J Virol. Dec. 2005;79(23):14793-803.
Snyder et al., Comparison of adeno-associated viral vector serotypes for spinal cord and motor neuron gene delivery. Hum Gene Ther. Sep. 2011;22(9):1129-35. doi: 10.1089/hum.2011.008. Epub Jul. 25, 2011.

(56) References Cited

OTHER PUBLICATIONS

Stoica et al., Targeting Human SOD1 Using AAV mediated RNAi in a mouse model of amyotrophic lateral sclerosis. Mol ther. Jun. 2013;21(1):S149.

Storkebaum et al., Treatment of motoneuron degeneration by intracerebroventricular delivery of VEGF in a rat model of ALS. Nat Neurosci. Jan. 2005;8(1):85-92. Epub Nov. 28, 2004.

Tenenbaum et al., Recombinant AAV-mediated gene delivery to the central nervous system. J Gene Med. Feb. 2004;6 Suppl 1:S212-22.

Tomar et al., Use of adeno-associated viral vector for delivery of small interfering RNA. Oncogene. Aug. 28, 2003;22(36):5712-5.

Towne et al., Systemic AAV6 delivery mediating RNA interference against SOD1: neuromuscular transduction does not alter disease progression in fALS mice. Mol Ther. Jun. 2008;16(6):1018-25. doi:10.1038/mt.2008.73. Epub Apr. 15, 2008.

Truong et al., Development of an intein-mediated split-Cas9 system for gene therapy. Nucleic Acids Res. Jul. 27, 2015;43(13):6450-8. doi: 10.1093/nar/gkv601. Epub Jun. 16, 2015.

Vandenberghe et al., Tailoring the AAV vector capsid for gene therapy. Gene Ther. Mar. 2009;16(3):311-9. Epub Dec. 4, 2008.

Vandendriessche et al., Efficacy and safety of adeno-associated viral vectors based on serotype 8 and 9 vs. lentiviral vectors for hemophilia B gene therapy. J Thromb Haemost. Jan. 2007;5(1):16-24. Epub Sep. 26, 2006.

Wang et al., Neuroprotective effects of glial cell line-derived neurotrophic factor mediated by an adeno-associated virus vector in a transgenic animal model of amyotrophic lateral sclerosis. J Neurosci. Aug. 15, 2002;22(16):6920-8.

Wang et al., Rescue and replication of adeno-associated virus type 2 as well as vector DNA sequences from recombinant plasmids containing deletions in the viral inverted terminal repeats: selective encapsidation of viral genomes in progeny virions. J Virol. Mar. 1996;70(3):1668-77.

Wang et al., Somatically Repairing Compound Heterozygous Recessive Mutations by Chromosomal Cut-and-Paste for in Vivo Gene Therapy. May 2016. 24(1):S289. Abstract 733.

Wang et al., The design of vectors for RNAi delivery system. Curr Pharm Des. 2008;14(13):1327-40.

Wang et al., The potential of adeno-associated viral vectors for gene delivery to muscle tissue. Expert Opin Drug Deliv. Mar. 2014;11(3):345-64. doi: 10.1517/17425247.2014.871258. Epub Jan. 3, 2014.

Wang et al., Therapeutic gene silencing delivered by a chemically modified small interfering RNA against mutant SOD1 slows amyotrophic lateral sclerosis progression. J Biol Chem. Jun. 6, 2008;283(23):15845-52. doi: 10.1074/jbc.M800834200. Epub Mar. 26, 2008.

Wang et al., Widespread spinal cord transduction by intrathecal injection of rAAV delivers efficacious RNAi therapy for amyotrophic lateral sclerosis. Hum Mol Genet. Feb. 1, 2014;23(3):668-81. doi: 10.1093/hmg/ddt454. Epub Sep. 18, 2013.

Watson et al., Intrathecal administration of AAV vectors for the treatment of lysosomal storage in the brains of MPS I mice. Gene Ther. Jun. 2006;13(11):917-25.

Wein et al., Efficient bypass of mutations in dysferlin deficient patient cells by antisense-induced exon skipping. Hum Mutat. Feb. 2010;31(2):136-42. doi: 10.1002/humu.21160.

Weismann et al., Systemic AAV9 gene transfer in adult GM1 gangliosidosis mice reduces lysosomal storage in CNS and extends lifespan. Hum Mol Genet. Aug. 1, 2015;24(15):4353-64. doi: 10.1093/hmg/ddv168. Epub May 10, 2015.

Weismann, Approaches and Considerations Towards a Safe and Effective Adena-Associated Virus Mediated Therapeutic Intervention for GM 1-Gangliosidosis: A Dissertation. University Massachusetts Medical School. Aug. 5, 2014.

Xia et al., Allele-specific RNAi selectively silences mutant SOD1 and achieves significant therapeutic benefit in vivo. Neurobiol Dis. Sep. 2006;23(3):578-86. Epub Jul. 20, 2006.

Xie et al., 676. DNA Sequences Encoding shRNAs Can Replace Mutant ITR in scAAV Genome for Efficient Replication and Packaging and Transcribe shRNAs by pol III Promoter Activity of wt ITR for Efficient Gene Silencing Mol Therapy. May 2015;23(1):S269.

Xie et al., Characterization of positioning effect of pol III-shRNA transcription unit in scAAV vector genome on the packaging efficiency and functionality of shRNA silencing. Molecular Therapy. May 2010;18(1): S262. Abstract 671.

Xie et al., rAAV-mediated delivery of micro RNA scavengers leads to efficient and stable knock-down of cognate micro RNAs, upregulation of their natural target genes and phenotypic changes in mice. Molecular Therapy. May 2010;18(1): S140. Abstract 362.

Xie et al., Short DNA Hairpins Compromise Recombinant Adeno-Associated Virus Genome Homogeneity. Mol Ther. Jun. 7, 2017;25(6):1363-1374. doi: 10.1016/j.ymthe.2017.03.028. Epub Apr. 24, 2017.

Xu et al., Delivery of MDR1 small interfering RNA by self-complementary recombinant adeno-associated virus vector. Mol Ther. Apr. 2005;11(4):523-30.

Zincarelli et al., Analysis of AAV serotypes 1-9 mediated gene expression and tropism in mice after systemic injection. Mol Ther. Jun. 2008;16(6):1073-80. doi: 10.1038/mt.2008.76. Epub Apr. 15, 2008.

Zolotukhin et al., Production and purification of serotype 1, 2, and 5 recombinant adeno-associated viral vectors. Methods. Oct. 2002;28(2):158-67.

Extended European Search Report for Application No. 19814935.3, dated Sep. 16, 2022.

International Preliminary Report on Patentability for Application No. PCT/US2019/036045, dated Dec. 17, 2020.

Blandin et al., UMD-DYSF, a novel locus specific database for the compilation and interactive analysis of mutations in the dysferlin gene. Hum Mutat. Mar. 2012;33(3):E2317-31. doi: 10.1002/humu.22015. Epub Dec. 29, 2011.

Dominov et al., Correction of pseudoexon splicing caused by a novel intronic dysferlin mutation. Ann Clin Transl Neurol. Mar. 3, 2019;6(4):642-654. doi: 10.1002/acn3.738.

\* cited by examiner

A.

B.

A.

COMPOSITIONS AND METHODS FOR MODULATING DYSFERLIN EXPRESSION

RELATED APPLICATIONS

This application is a continuation under 35 U.S.C. § 120 of U.S. application Ser. No. 15/316,027, filed Dec. 2, 2016, entitled "COMPOSITIONS AND METHODS FOR MODULATING DYSFERLIN EXPRESSION", which is a national stage filing under 35 U.S.C. § 371 of International Patent Application Serial No. PCT/US2015/033973, filed Jun. 3, 2015, entitled "COMPOSITIONS AND METHODS FOR MODULATING DYSFERLIN EXPRESSION", which claims the benefit under 35 U.S.C. § 119(e) of U.S. Application Ser. No. 62/007,397, filed Jun. 3, 2014, entitled "COMPOSITIONS AND METHODS FOR MODULATING DYSFERLIN EXPRESSION"; the entire contents of each of which are incorporated herein by reference.

BACKGROUND

Dysferlin (DYSF) is a large transmembrane protein and a member of the ferlin family of $Ca^{2+}$-dependent phospholipid-binding proteins that play a role in membrane vesicle fusion and membrane repair. Insufficient levels of normal dysferlin lead to specific forms of muscular dystrophy (dysferlinopathies) that include Miyoshi myopathy (MM), limb-girdle muscular dystrophy type 2B (LGMD-2B) and distal myopathy with anterior tibial onset (DMAT). These recessively-inherited diseases are characterized by progressive, muscle weakness with typical onset in late teens to early twenties, beginning either in proximal (LGMD-2B) or in distal muscles (MM, DMAT) but eventually affecting broader groups of muscles similarly. Clinical symptoms include muscle degeneration accompanied by substantial elevation serum creatine kinase (CK), indicative of muscle damage, inflammation and abnormal muscle morphology. As with other forms of muscular dystrophy, there is currently no cure for dysferlinopathies, and a need exists for new therapeutic approaches to treat these genetic diseases.

SUMMARY

Aspects of the disclosure relate to compositions and methods for modulating dysferlin expression by altering splicing of RNA expressed from a DYSF gene. In particular, aspects of the disclosure relate to a new deep intronic mutation identified in dysferlin intron 44i that alters the splicing of mRNA and leads to the inclusion of a pseudoexon between exons 44 and 45 (DYSF PE44.1). DYSF PE44.1 maintains the reading frame, adding 59 amino acids within the conserved C2F domain, and disrupting function. In some embodiments, an exon-skipping strategy is provided that induces altered splicing in this PE44.1 mutant region of DYSF mRNA. In such embodiments, antisense nucleic acids designed to prevent DYSF PE44.1 splicing restore normal mRNA splicing and thus normal protein (as opposed to a modified or truncated version currently possible with other exon targets). Antisense nucleic acids provided herein that target DYSF PE44.1 reduce expression of the mutant mRNA splice form and restore higher levels of the normal form of mRNA and greater protein levels.

Aspects of the disclosure relate to a method of modulating splicing in a cell that contains a DYSF gene comprising a c.4886+1249 (G>T) mutation. In some embodiments, the method involves delivering to the cell an antisense nucleic acid that targets a pre-messenger RNA expressed from the DYSF gene and alters splicing of the pre-messenger RNA such that exons 44 and 45 of the pre-messenger RNA are spliced together without an intervening pseudoexon. In some embodiments, the cell is heterozygous for the c.4886+1249 (G>T) point mutation. In some embodiments, the cell is homozygous for the c.4886+1249 (G>T) point mutation. In certain embodiments, the cell contains a second DYSF gene encoding a wild-type DYSF protein. In some embodiments, the cell contains a second DYSF gene comprising a mutation that causes a premature stop codon. In certain embodiments, the premature stop codon is within a region encoding the C2D domain of DYSF protein. In some embodiments, the second DYSF gene is a human DYSF gene, and the mutation that causes the premature stop codon is a c.3444_3445delTGinsAA mutation. In certain embodiments, the cell is in vitro. In some embodiments, the cell is in vivo. In certain embodiments, the cell is a non-human cell engineered to contain the DYSF gene comprising the c.4886+1249 (G>T) mutation. In some embodiments, the cell is a human cell. In certain embodiments, the human cell is engineered to contain the DYSF gene comprising the c.4886+1249 (G>T) mutation. In some embodiments, the human cell is from a subject having a muscular dystrophy that is associated at least in part with the DYSF gene comprising the c.4886+1249 (G>T) mutation. In certain embodiments, the muscular dystrophy is of the Miyoshi Myopathy-type, or other muscular dystrophy caused by abnormal expression of the dysferlin gene product.

Aspects of the disclosure relate to a method of modulating splicing in a cell containing a DYSF gene that encodes a pre-messenger RNA having a pseudoexon incorporated between exons 44 and 45. In some embodiments, the method involves delivering to the cell an antisense nucleic acid (e.g., an oligonucleotide) that targets the pre-messenger RNA encoded by the human DYSF gene and alters splicing of the pre-messenger RNA such that the pseudoexon is not incorporated between exons 44 and 45 of the pre-messenger RNA. In some embodiments, the DYSF gene is a human DYSF gene that comprises a c.4886+1249 (G>T) mutation. In certain embodiments, the antisense nucleic acid is an oligonucleotide of 10 to 25 nucleotides in length comprising a region of complementarity that is complementary with at least 8 contiguous nucleotides of a sequence within a region between exons 43 and 46 encoded by the DYSF gene. In some embodiments, the antisense nucleic acid is an oligonucleotide of 10 to 25 nucleotides in length comprising a region of complementarity that is complementary with at least 8 contiguous nucleotides of a sequence within a region between exons 44 and 45 encoded by the DYSF gene. In certain embodiments, the antisense nucleic acid is an oligonucleotide comprising a sequence of any one of AON1 to AON20 as set forth in Tables 4 and 8. In some embodiments, the antisense nucleic acid is expressed from a transgene. In some embodiments, the transgene is delivered to the cell using a viral vector. In certain embodiments, the viral vector is a recombinant AAV vector.

Aspects of the disclosure relate to a method of altering RNA splicing in a subject. In some embodiments, the method involves administering to the subject an antisense nucleic acid (e.g., an oligonucleotide) that targets a pre-messenger RNA encoded by a human DYSF gene and alters splicing of the pre-messenger RNA such that exons 44 and 45 of the RNA are spliced together without an intervening pseudoexon, wherein the human DYSF gene comprises a c.4886+1249 (G>T) mutation. In some embodiments, the method further involves, prior to administering the antisense nucleic acid, detecting that the subject has the human DYSF gene that comprises the c.4886+1249 (G>T) mutation. In certain embodiments, the human DYSF gene is detected using a hybridization assay that discriminates between the presence of a guanosine and a thymidine at position c.4886+1249 of the human DYSF gene. In some embodiments, the hybridization assay is a polymerase chain reaction (PCR) assay. In certain embodiments, the PCR assay comprises using a primer or probe that is at least partially complementary with a nucleic acid having a sequence as set forth in any one of SEQ ID NOs: 117 to 121 or a complementary sequence thereof. In some embodiments, the antisense nucleic acid is an oligonucleotide of 10 to 25 nucleotides in length comprising a region of complementarity that is complementary with at least 8 contiguous nucleotides of a sequence within a region between exons 43 and 46 encoded by a human DYSF gene. In certain embodiments, the antisense nucleic acid is an oligonucleotide of 10 to 25 nucleotides in length comprising a region of complementarity that is complementary with at least 8 contiguous nucleotides of a sequence within a region between exons 44 and 45 encoded by a human DYSF gene. In certain embodiments, the antisense nucleic acid is an oligonucleotide comprising a sequence of any one of AON1 to AON20 as set forth in Tables 4 and 8. In some embodiments, the antisense nucleic acid is expressed from a transgene. In certain embodiments, the transgene is administered to the subject using a viral vector. In some embodiments, the viral vector is a recombinant AAV vector.

Aspects of the disclosure relate to oligonucleotides of 10 to 25 nucleotides in length comprising a region of complementarity that is complementary with at least 8 contiguous nucleotides of a sequence within a region between exons 43 and 46 encoded by a human DYSF gene. In some embodiments, the oligonucleotide comprises at least one modified nucleotide or at least one modified internucleotide linkage. In some embodiments, the human DYSF gene comprises a c.4886+1249 (G>T) mutation. In certain embodiments, the region of complementarity is complementary with at least 8 contiguous nucleotides of a sequence as set forth as SEQ ID NO: 116. In some embodiments, the region of complementarity is complementary with at least 8 contiguous nucleotides of a sequence as set forth as SEQ ID NO: 117, 118, 119, 120, or 121. In some embodiments, the region of complementarity is complementary with an exonic splice enhancer or inhibitor sequence. In certain embodiments, the region of complementarity is complementary with a splice donor motif. In some embodiments, the region of complementarity is complementary with a splice acceptor motif. In certain embodiments, the region of complementarity is complementary with a lariat branch point. In some embodiments, the human DYSF gene comprises a mutation that results an in-frame pseudoexon between exons 44 and 45. In certain embodiments, the oligonucleotide, when present in a cell that contains the human DYSF gene, alters splicing of a pre-messenger RNA expressed from the human DYSF gene such that the pseudoexon is not incorporated between exons 44 and 45. In some embodiments, the oligonucleotide comprises at least one modified nucleotide. In certain embodiments, the at least one modified nucleotide is a 2'-modified nucleotide. In some embodiments, the 2'-modified nucleotide is a 2'-deoxy, 2'-fluoro, 2'-O-methyl, 2'-O-methoxyethyl, 2'-amino and 2'-aminoalkoxy modified nucleotides. In certain embodiments, the 2'-modified nucleotide comprises a 2'-O-4'-C methylene bridge. In some embodiments, the oligonucleotide comprises at least one modified internucleotide linkage. In certain embodiments, the at least one modified internucleotide linkage is a phosphorothioate modified linkage. In some embodiments, the oligonucleotide is a morpholino (or modified morpholino, e.g. peptide conjugated morpholino). In certain embodiments, the oligonucleotide comprises alternating LNA and RNA nucleotides. In some embodiments, the oligonucleotide comprises alternating LNA and DNA nucleotides. In certain embodiments, the oligonucleotide comprises alternating RNA and DNA nucleotides. In some embodiments, the oligonucleotide, when present in a cell that contains the human DYSF gene, is capable of hybridizing with RNA expressed from the human DYSF gene without inducing cleavage of the RNA by an RNase. In certain embodiments, the oligonucleotide comprises a sequence of any one of AON1 to AON20 as set forth in Tables 4 and 8. In some embodiments, the oligonucleotide comprises a region of complementarity that is complementary with at least 8 contiguous nucleotides of a sequence within a region between exons 44 and 45 encoded by a human DYSF gene. Further aspects of the disclosure relate to compositions comprising one or more oligonucleotides disclosed herein and a carrier. In some embodiments, the composition is a pharmaceutical composition comprising a pharmaceutically-acceptable carrier.

Aspects of the disclosure relate to a preparation of oligonucleotides, in which at least 95% (e.g., at least 98%, at least 99%) of the oligonucleotides are 10 to 25 nucleotides in length and comprise a region of complementarity that is complementary with at least 8 contiguous nucleotides of a sequence within a region between exons 43 and 46 encoded by a human DYSF gene. In some embodiments, the region of complementarity is complementary with at least 8 contiguous nucleotides of a sequence as set forth in SEQ ID NO: 116. In certain embodiments, the region of complementarity is complementary with at least 8 contiguous nucleotides of a sequence as set forth in SEQ ID NO: 117, 118, 119, 120 or 121. In some embodiments, the region of complementarity is complementary with an exonic splice enhancer or inhibitor sequence. In certain embodiments, the region of complementarity is complementary with a splice donor motif. In some embodiments, the region of complementarity is complementary with a splice acceptor motif. In certain embodiments, the region of complementarity is complementary with a lariat branch point. In some embodiments, the human DYSF gene comprises a mutation that results an in-frame pseudoexon between exons 44 and 45. In certain embodiments, the oligonucleotide, when present in a cell that contains the human DYSF gene, alters splicing of an RNA expressed from the human DYSF gene such that the pseudoexon is not incorporated between exons 44 and 45. In some embodiments, the oligonucleotides are lyophilized. In certain embodiments, at least 95%, at least 98%, or at least 99% of the oligonucleotides are identical. In some embodiments, the oligonucleotides comprises a sequence of any one of AON1 to AON20 as set forth in Tables 4 and 8. In certain embodiments, the preparation comprise a region of complementarity that is complementary with at least 8 contiguous nucleotides of a sequence within a region between exons 44 and 45 encoded by a human DYSF gene.

Aspects of the disclosure relate to kits comprising a container housing a preparation disclosed herein.

Aspects of the disclosure relate to a pair of PCR primers having sequences selected from the primer sequences set forth Table 1 or Table 5.

Aspects of the disclosure relate to compositions comprising a pair of PCR primers disclosed herein and a template comprising at least a portion of a human DYSF gene.

Further aspects of the disclosure relate to a composition comprising a pair of PCR primers disclosed herein and a probe having as sequence as set forth in Table 3.

Still further aspects of the disclosure relate to a labelled oligonucleotide comprising a sequence set forth as: CACC-TACCACTTCCCTCCA (SEQ ID NO: 51) or ACCTAC-CACTTACCTCCA (SEQ ID NO: 52) or a fragment thereof that is useful for detecting presence or absence of a c.4886+1249 (G>T) mutation in a DYSF gene.

In certain aspects, the disclosure relates to an expression construct encoding an antisense nucleic acid having a region of complementarity that is complementary with a sequence between exons 43 and 46 encoded by a human DYSF gene. In some embodiments, the human DYSF gene comprises a c.4886+1249 (G>T) mutation. In certain embodiments, the region of complementarity is complementary with at least 8 contiguous nucleotides of a sequence as set forth as SEQ ID NO: 116. In some embodiments, the region of complementarity is complementary with at least 8 contiguous nucleotides of a sequence as set forth as SEQ ID NO: 117, 118, 119, 120 or 121. In certain embodiments, the region of complementarity comprises a sequence complementary with an exonic splice enhancer or inhibitor sequence. In some embodiments, the region of complementarity comprises a sequence complementary with a splice donor motif. In certain embodiments, the region of complementarity comprises a sequence complementary with a splice acceptor motif. In some embodiments, the region of complementarity comprises a sequence complementary with a lariat branch point. In certain embodiments, the antisense nucleic acid expressed from the vector, when present in a cell that contains the human DYSF gene, alters splicing of a pre-messenger RNA expressed from the human DYSF gene such that the pseudoexon is not incorporated between exons 44 and 45. Further aspects of the disclosure relate to a recombinant AAV or other viral vector comprising an expression construct disclosed herein.

According to some aspects of the disclosure, an engineered cell is provided that comprises an exogenous human DYSF gene having a c.4886+1249 (G>T) mutation, in which the cell expresses a pre-messenger RNA from the exogenous DYSF gene containing a pseudoexon between exons 44 and 45. In some embodiments, the cell is not of a human origin. In certain embodiments, the cell is of a human origin. In some aspects, a composition is provided that comprises cells containing a human DYSF gene having a c.4886+1249 (G>T) mutation and an artificial cell culture medium. In some embodiments, a tissue culture system is provided that comprises such a composition. In some embodiments, the composition further comprise an oligonucleotide disclosed herein, e.g., which oligonucleotide has been delivered to the cells to modulate DYSF expression.

In still further aspects of the disclosure a transgenic organism is provided that comprises an engineered cell disclosed herein. In some embodiments, the organism is a mammal. In some embodiments, the mammal is a rodent. In some embodiments, the rodent is mouse or rat.

In some aspects, the disclosure provides an antibody or antigen binding fragment thereof that binds selectively to a DYSF variant or portion thereof. In some embodiments, the DYSF variant or portion thereof comprises or consists of a peptide encoded by SEQ ID NO: 116. In some embodiments, the antibody targets the C-terminal portion of the peptide encoded by SEQ ID NO: 116. In some embodiments, the antibody targets an amino acid sequence as set forth in SEQ ID NO: 122.

In some aspects, the disclosure provides a method of identifying and/or treating a DYSF intronic mutation, the method comprising: (a) amplifying and/or sequencing a nucleic acid obtained from or prepared from a biological sample obtained from a subject (e.g., using at least one primer set as set forth in Table 1, Table 2 and/or Table 3) to detect the presence of a c.4886+1249 (G>T) mutation in a DYSF gene; or (b) performing an immunoassay (e.g., an ELISA, Western blot, e.g., using an anti-PE44.1 antibody) on a biological sample obtained from a subject; and, (c) diagnosing or aiding in diagnosing the subject has having an intronic mutation in the DYSF gene based upon detection of the c.4886+1249 (G>T) mutation in (a) or detection of the protein product encoded by PE44.1 in (b).

In some aspects, the disclosure provides a method of identifying and/or treating a DYSF intronic mutation, the method comprising: (a) amplifying the cDNA of a biological sample obtained from a subject using at least one primer set as set forth in Table 1, Table 2 and/or Table 3 to detect the presence of a c.4886+1249 (G>T) mutation in a DYSF gene; or (b) performing a Western blot on a biological sample obtained from a subject, wherein the Western blot is probed with an anti-PE44.1 antibody; and, (c) diagnosing the subject has having an intronic mutation in the DYSF gene based upon detection of the c.4886+1249 (G>T) mutation in (a) or detection of the protein product encoded by PE44.1 in (b).

In some embodiments, the biological sample is blood or muscle tissue. In some embodiments, the blood comprises monocytes. In some embodiments, the monocytes are isolated, optionally by cell a sorting method.

In some embodiments, the method further comprises administering to the subject an antisense oligonucleotide (e.g., an antisense oligonucleotide as described by the disclosure).

DETAILED DESCRIPTION

Figure 1:
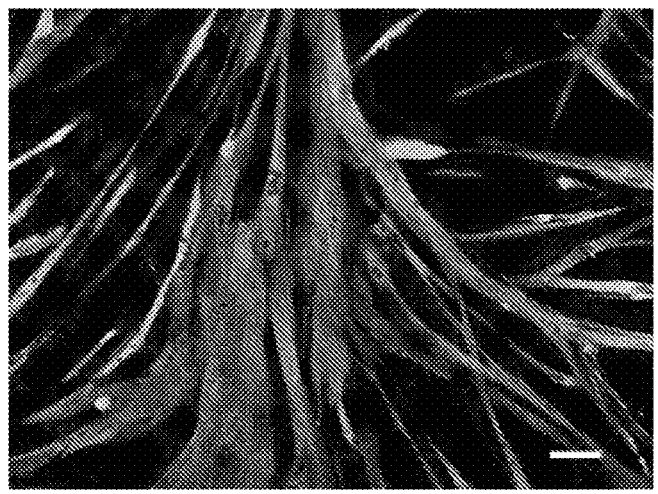
FIG. 1. (A) Myosin Heavy Chain (MHC) expression in iFDMS derived from patient P1 dermal fibroblasts stained with anti-MHC antibody. Nuclei are stained blue. (Scale bar 100 lam). (B) Western blots show dysferlin protein in iFDMs from patients P1 and P2, normal fibroblasts (N), and human UBic myotubes (Mt). iFDMs from patients express lower levels of DYSF than normal iFDMs, and this appears to be of normal size. GAPDH levels are shown as a control for protein loading.
Figure 1:
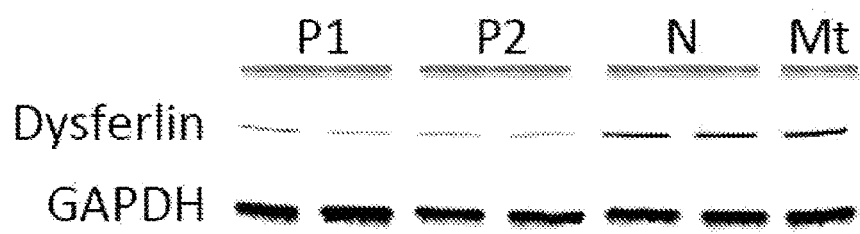

Aspects of the disclosure relate to methods of altering RNA splicing in a subject. In some embodiments, the disclosure relates to compositions and methods for modulating splicing in a cell that contains a DYSF gene having a mutation that results an in-frame pseudoexon between exons 44 and 45 that results in defects in dysferlin protein expression. There are a number of specific features of the dysferlin protein that contribute to its function and interaction with other proteins. As a member of the ferlin family, dysferlin has seven $Ca^{2+}$-sensitive phospholipid binding C2 domains (C2A through C2G) that vary in their phospholipid binding characteristics, relative importance for dysferlin dimerization and membrane interaction but collectively may play a role in altering the structure or curvature of lipid bilayers facilitating membrane fusion and interaction with other membrane associated proteins. Dysferlin interacts with a number of proteins that function in membrane trafficking and fusion including caveolin-3, annexins, affixin, calpain-3 and AHNAK. Through these interactions, dysferlin plays an important role in sarcolemma repair following membrane damage, as well as vesicle trafficking, membrane turnover, and T-tubule formation and stability.

Synthesis of the large (237 kDa) dysferlin is a protein is involved. The protein is derived from a ~6.2 kb transcript assembled from up to 55 exons. There are 14 isoforms of DYSF that can arise from use of two separate promoters and alternate exon splicing, with isoform 8 being the predominant form in skeletal muscle. Disease-causing mutations in dysferlin occur throughout the gene. Genetic data compiled in Universal Mutation Database for Dysferlin (UMD-DYSF, v.1.1 Apr. 26,2013) lists 337 disease-causing mutations that have been found in 725 patients worldwide. Approximately 48% of these patients are homozygous for specific mutations and approximately 52% are heterozygous. Roughly 17% of patients have only one mutant allele identified, and it is likely that the unknown allele carries a mutation within intronic or regulatory regions that are not identifiable through standard exome sequencing approaches. Alternative approaches are required to identify these other mutant alleles.

In some embodiments, there are at least 14 variants (e.g., isoforms) of DYSF transcripts that arise from the use of two separate promoters and/or alternate exon splicing events. In some embodiments, variant 8 is a predominant form of DYSF in skeletal muscle. In some embodiments, DYSF mRNA variant 8 (NM_003494.3) is used as a reference sequence for RNA and cDNA analyses and/or as a context for specifying exon and intron numeric assignments and nomenclature.

Some aspects of the present disclosure relate to the identification of a novel mutant allele in certain Miyoshi myopathy (MM) patients that have only one of their mutant alleles identified. In some embodiments, such patients lack normal dysferlin in their muscles and are heterozygous for a nonsense mutation in an exon of one allele of the DYSF gene but the other disease causing mutation has not been identified despite multiple exome sequencing efforts. Some aspects of the present disclosure relate to the identification of a deep intronic point mutation within intron 44 (44i) that leads to abnormal mRNA and protein structure. Other aspects of the present disclosure relate to the partial restoration of normal DYSF mRNA and protein levels in myogenic cells from these patients using antisense nucleic acids to by-pass the effects of the 44i mutation, providing a novel therapeutic strategy to restore DYSF function.

Accordingly, methods are provided herein that involve delivering to the cell an antisense nucleic acid that targets a pre-messenger RNA expressed from the DYSF gene and alters splicing of the pre-messenger RNA such that exons 44 and 45 of the pre-messenger RNA are spliced together without an intervening pseudoexon. In some embodiments, the DYSF gene comprises a c.4886+1249 (G>T) mutation. In this context, c.4886+1249 refers to the mutational position relative to the ATG start codon of the transcript (the coding sequence) for dysferlin using the predominant mRNA in muscle, isoform 8 (NCBI Reference Sequence: NM_003494.3), as the reference. c.4886 is the last nucleotide of exon 44. The mutation is at the 1249th nucleotide after this position, within the intron (44i). Normally this 1249th nucleotide is a "G", but certain diseased patients this is mutated to a "T". In some embodiments, the cell is heterozygous for the c.4886+1249 (G>T) point mutation.

As used herein, the term, "antisense nucleic acid," refers to a nucleic acid that has sequence complementarity to a target sequence and is specifically hybridizable, e.g., under stringent conditions, with a nucleic acid having the target sequence. An antisense nucleic acid is specifically hybridizable when binding of the antisense nucleic acid to the target nucleic acid is sufficient to produce complementary based pairing between the antisense nucleic acid and the target nucleic acid, and there is a sufficient degree of complementarity to avoid non-specific binding of the antisense nucleic acid to non-target nucleic acid under conditions in which specific binding is desired, e.g., under physiological conditions in the case of in vivo assays or therapeutic treatment, and in the case of in vitro assays, under conditions in which the assays are performed.

In some embodiments, an antisense nucleic acid is used that has a region of complementarity that is perfectly complementary to a portion of a target nucleic acid (e.g., target RNA). However, it should be appreciated that in some embodiments, an antisense nucleic acid may be used that has less than 100% sequence complementarity with a target nucleic acid. An antisense nucleic acid oligonucleotide may comprise a region of complementarity that is complementary with sequence as set forth in SEQ ID NO: 116, 117, 118 or 119. The region of complementarity of the antisense nucleic acid may be complementary with at least 6, e.g., at least 7, at least 8, at least 9, at least 10, at least 15 or more consecutive nucleotides of a target nucleic acid. In addition, to minimize the likelihood of off-target effects, an antisense nucleic acid may be designed to ensure that it does not have a sequence (e.g., of 5 or more consecutive nucleotides) that is complementary with an off-target nucleic acid.

Complementary refers to the capacity for precise pairing between two nucleotides. For example, if a nucleotide at a certain position of an antisense nucleic acid is capable of hydrogen bonding with a nucleotide at the corresponding position of a target nucleic acid (e.g., target RNA), then the antisense nucleic acid and target nucleic acid are considered to be complementary to each other at that position. The antisense nucleic acid and target nucleic acid are complementary to each other when a sufficient number of corresponding positions in each molecule are occupied by nucleotides that can hydrogen bond with each other through their bases. Thus, "complementary" is a term that is used to indicate a sufficient degree of complementarity or precise pairing such that stable and specific binding occurs between the antisense nucleic acid and target nucleic acid. However, it should be appreciated that 100% complementarity is not required. For example, in some embodiments, an antisense nucleic acid (e.g., an oligonucleotide) may be at least 80% complementary to (e.g., at least 85%, 90%, 91%, 92%, 93%, 940%, 95%, 96%, 97%, 98%, 99% or 100% complementary to) the consecutive nucleotides of a target nucleic acid.

Thus, it is understood in the art that a complementary nucleotide sequence need not be 100% complementary to that of its target to be specifically hybridizable. In some embodiments, a complementary nucleic acid sequence for purposes of the present disclosure is specifically hybridizable when binding of the sequence to the target nucleic acid produces the desired alterations in splicing to occur and there is a sufficient degree of complementarity to avoid non-specific binding to non-target nucleic acids under conditions in which avoidance of non-specific binding is desired, e.g., under physiological conditions in the case of in vivo assays or therapeutic treatment, and in the case of in vitro assays, under conditions in which the assays are performed under suitable conditions of stringency.

Sequence identity, including determination of sequence complementarity for nucleic acid sequences, may be determined by sequence comparison and alignment algorithms known in the art. To determine the percent identity of two nucleic acid sequences, the sequences are aligned for optimal comparison purposes (e.g., gaps can be introduced in the first sequence or second sequence for optimal alignment). The nucleotides at corresponding nucleotide positions are then compared. When a position in the first sequence is occupied by the same residue as the corresponding position in the second sequence, then the molecules are identical at that position. In some embodiments, the percent identity between the two sequences is a function of the number of identical positions shared by the sequences (e.g., % homology=# of identical positions/total # of positions×100), optionally penalizing the score for the number of gaps introduced and/or length of gaps introduced.

In some embodiments, an antisense nucleic acid is an antisense oligonucleotide (AON), which may be referred to simply as an oligonucleotide. For example, in some embodiments, oligonucleotides are provided that comprise a region of complementarity that is complementary with at least 8, at least 9, at least 10, at least 11, at least 12, at least 13, at least 14, at least 15 or more contiguous nucleotides of a sequence within a region between exons 44 and 45 encoded by a human DYSF gene. Such oligonucleotides are useful for modulating splicing of dysferlin and prevent incorporation of a pseudoexon between exons 44 and 45. In some embodiments, an antisense nucleic acid is an antisense oligonucleotide (AON) recited in Table 4 or Table 8.

In some embodiments, oligonucleotides of the disclosure have a length in a range of 5 to 40 nucleotides, 5 to 30 nucleotides, 10 to 30 nucleotides, 10 to 25 nucleotides, or 15 to 25 nucleotides. In some embodiments of the disclosure, oligonucleotides have a length of 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 or more. In some embodiments, the oligonucleotide comprises a region of complementarity that is complementary with a region within 5, 10, 15, 25, 50, 100 or 200 nucleotides of a c.4886+1249 (G>T) mutation in a human DYSF gene. In some embodiments, the oligonucleotide comprises a region of complementarity that is complementary with at least 8 contiguous nucleotides of a sequence as set forth as SEQ ID NO: 116. In some embodiments, the oligonucleotide comprises a region of complementarity that is complementary with at least 8 contiguous nucleotides of a sequence as set forth as SEQ ID NO: 117, 118 or 119. The region of complementarity may be complementary with an exonic splice enhancer or inhibitor sequence, a splice donor motif, a splice acceptor motif or a lariat branch point encoded by a human DYSF gene (e.g., within a region spanning from exon 44 to exon 45).

In some embodiments, antisense nucleic acids (e.g., oligonucleotides) are provided in a homogeneous preparation, e.g., in which at least 85%, at least 90%, at least 95%, or at least 99% of the oligonucleotides are identical. For example, in some embodiments, homogeneous preparations of oligonucleotides are provided in which at least 85%, at least 90%, at least 95%, or at least 99% of the oligonucleotides in the preparation are 10 to 25 nucleotides in length and comprise a region of complementarity that is complementary with at least 8 contiguous nucleotides of a sequence within a region between exons 43 and 46 encoded by a human DYSF gene.

Antisense nucleic acids of the disclosure may be modified to achieve one or more desired properties, such as, for example, improved cellular uptake, improved stability, reduced immunogenicity, improved potency, improved target hybridization, susceptibility to RNAse cleavage, etc. In some embodiments, an antisense nucleic acid is modified such that when present in a cell that contains a human DYSF gene, it is capable of hybridizing with RNA expressed from the human DYSF gene without inducing cleavage of the RNA by an RNase. Antisense nucleic acids can be modified at a base moiety, sugar moiety and/or phosphate backbone. Accordingly, antisense nucleic acids may have one or more modified nucleotides (e.g., a nucleotide analog) and/or one or more backbone modifications (e.g., a modified internucleotide linkage). Antisense nucleic acids may have a combination of modified and unmodified nucleotides. Antisense nucleic acids may also have a combination of modified and unmodified internucleotide linkages.

Antisense nucleic acids may include ribonucleotides, deoxyribonucleotides, and combinations thereof. Examples of modified nucleotides which can be used in antisense nucleic acids include, for example, 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil. 5-methyluracil, uracil-5-oxyacetic acid methylester, uracil-5-oxyacetic acid (v), 5-methyl-2-thiouracil, 3-(3-amino-3-N-2-carboxypropyl) uracil, and 2,6-diaminopurine.

In some embodiments, a modified nucleotide is a 2'-modified nucleotide. For example, the 2'-modified nucleotide may be a 2'-deoxy, 2'-fluoro, 2'-O-methyl, 2'-O-methoxyethyl, 2'-amino and 2'-aminoalkoxy modified nucleotides. In some embodiments, the 2'-modified nucleotide comprises a 2'-O-4'-C methylene bridge, such as a locked nucleic acid (LNA) nucleotide. In some embodiments of a 2' modified nucleotide the 2'-hydroxyl group is linked to the 3' or 4' carbon atom of the sugar ring thereby forming a bicyclic sugar moiety. In such embodiments, the linkage may be a methelyne (—CH2—)$_n$ group bridging the 2' oxygen atom and the 3' or 4' carbon atom wherein n is 1 or 2.

Antisense nucleic acids may include combinations of LNA nucleotides and unmodified nucleotides. Antisense nucleic acids may include combinations LNA and RNA nucleotides. Antisense nucleic acids may include combinations LNA and DNA nucleotides. A further preferred oligonucleotide modification includes Locked Nucleic Acids (LNAs) in which the 2'-hydroxyl group is linked to the 3' or 4' carbon atom of the sugar ring thereby forming a bicyclic sugar moiety.

Antisense nucleotide acids may also include nucleobase-modified nucleotides, e.g., nucleotides containing a non-naturally occurring nucleobase instead of a naturally occurring nucleobase. Bases may be modified to block the activity of adenosine deaminase, for example. Examples of modified nucleobases include, but are not limited to, uridine and/or cytidine modified at the 5-position, e.g., 5-(2-amino)propyl uridine, 5-bromo uridine; adenosine and/or guanosines modified at the 8 position, e.g., 8-bromo guanosine; deaza nucleotides, e.g., 7-deaza-adenosine; O- and N-alkylated nucleotides, e.g., N6-methyl adenosine are suitable. It should be noted that the above modifications may be combined.

Within antisense nucleic acids (e.g., oligonucleotides) of the disclosures, as few as one and as many as all nucleotides can be modified. For example, an oligonucleotide (e.g., an oligonucleotide of 20 nucleotides in length) may contain 1, 2, 3, 4, 5, 6, 7, 8, 9, 10, 11, 12, 13, 14, 15, 16, 17, 18, 19 or 20 modified nucleotides. In some embodiments, a modified oligonucleotide will contain as few modified nucleotides as are necessary to achieve a desired level of in vivo stability and/or bioaccessibility or other desired property.

Certain antisense nucleic acids may include nonionic DNA analogs, such as alkyl- and aryl-phosphates (in which the charged phosphonate oxygen is replaced by an alkyl or aryl group), phosphodiester and alkylphosphotriesters, in which the charged oxygen moiety is alkylated. Nucleic acids which contain a diol, such as tetraethyleneglycol or hexaethyleneglycol, at either or both termini have also been shown to be substantially resistant to nuclease degradation and may be used herein. In some embodiments, antisense nucleic acids may include at least one lipophilic substituted nucleotide analog and/or a pyrimidine-purine dinucleotide.

In some embodiments, antisense nucleic acids (e.g., oligonucleotides) may have one or two accessible 5' ends. It is possible to create modified oligonucleotides having two such 5' ends, for instance, by attaching two oligonucleotides through a 3'-3' linkage to generate an oligonucleotide having one or two accessible 5' ends. The 3'3'-linkage may be a phosphodiester, phosphorothioate or any other modified internucleoside bridge. Additionally, 3'3'-linked oligonucleotides where the linkage between the 3' terminal nucleosides is not a phosphodiester, phosphorothioate or other modified bridge, can be prepared using an additional spacer, such as tri- or tetra-ethylenglycol phosphate moiety.

A phosphodiester internucleotide linkage of an antisense nucleic acid can be replaced with a modified linkage. The modified linkage may be selected from, for example, phosphorothioate, phosphorodithioate, NR1R2-phosphoramidate, boranophosphate, α-hydroxybenzyl phosphonate, phosphate-(C1-C21)—O-alkyl ester, phosphate-[(C6-C12) aryl-(C1-C21)—O-alkyl]ester, (C1-C8)alkylphosphonate and/or (C6-C12)arylphosphonate bridges, and (C7-C12)-α-hydroxymethyl-aryl.

A phosphate backbone of the antisense nucleic acid can be modified to generate peptide nucleic acid molecules. As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols, for example.

Antisense nucleic acids can also be formulated as morpholino oligonucleotides. In such embodiments, the riboside moiety of each subunit of an oligonucleotide of the oligonucleotide reagent is converted to a morpholine moiety. Morpholinos may also be modified, e.g. as peptide conjugated morpholino)

In other embodiments, the antisense nucleic acid (e.g., oligonucleotide) can be linked to functional groups such as peptides (e.g., for targeting host cell receptors in vivo), or agents facilitating transport across the cell membrane or the blood-brain barrier. Oligonucleotide reagents of the disclosure also may be modified with chemical moieties (e.g., cholesterol) that improve the in vivo pharmacological properties of the oligonucleotide reagents.

Treatment Methods

Aspects of the disclosure relate to methods of altering RNA splicing in a subject involving administering to the subject an antisense nucleic acid that targets a pre-messenger RNA encoded by a human DYSF gene and alters splicing of the pre-messenger RNA such that exons 44 and 45 of the RNA are spliced together without an intervening pseudoexon. In some embodiments, the subject is heterozygous a c.4886+1249 (G>T) mutation in the DYSF gene. However, in some embodiments, the subject is homozygous a c.4886+1249 (G>T) mutation in the DYSF gene. Often the subject has or is suspected of having muscular dystrophy (e.g., of the Miyoshi Myopathy-type) caused by abnormal expression of the dysferlin gene product and the methods are being implemented for purposes of treating the muscular dystrophy. Treating, in this case, includes improving dysferlin expression and/or ameliorating one or more symptoms of muscular dystrophy.

Any appropriate antisense nucleic acid disclosed herein may be administered. For example, the antisense nucleic acid may be an oligonucleotide (e.g., of 10 to 25 nucleotides in length) comprising a region of complementarity that is complementary with a sequence within a region between exons 43 and 46 encoded by a human DYSF gene. An antisense oligonucleotide may for example comprise a sequence of AON1 to AON20 as set forth in Tables 4 and 8.

In some embodiments, an antisense nucleic acid is expressed from a transgene, e.g., as an antisense RNA transcript. A transgene may be administered to a subject in a DNA expression construct that is engineered to express an antisense RNA transcript in a subject. A DNA expression construct may be administered directly or using a viral vector (e.g., a recombinant AAV (rAAV) vector) or other suitable vector. Viral vectors that have been used for gene therapy protocols include, but are not limited to, retroviruses, other RNA viruses such as poliovirus or Sindbis virus, adenovirus, adeno-associated virus (AAV), herpes viruses, SV 40, vaccinia, lentivirus and other DNA viruses.

Alternatively, a transgene may be express ex vivo and the resulting antisense RNA transcript may be administered directly to the subject.

As disclosed herein antisense nucleic acids (including DNA expression constructs that may be used to expressed them) may be administered by any suitable route. For use in therapy, an effective amount of the antisense nucleic acid (e.g. oligonucleotide) and/or other therapeutic agent can be administered to a subject by any mode that delivers the agent to the desired tissue, e.g., muscle tissue. In some embodiments, agents (e.g., antisense nucleic acids) are administered intramuscularly. Other suitable routes of administration include but are not limited to oral, parenteral, intravenous, intraperitoneal, intranasal, sublingual, intratracheal, inhalation, subcutaneous, ocular, vaginal, and rectal. Systemic routes include oral and parenteral. Several types of devices are regularly used for administration by inhalation. These types of devices include metered dose inhalers (MDI), breath-actuated MDI, dry powder inhaler (DPI), spacer/holding chambers in combination with MDI, and nebulizers.

For oral administration, the agents can be formulated readily by combining the active compound(s) with pharmaceutically acceptable carriers well known in the art. Such carriers enable the agents of the disclosure to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally oral formulations may also be formulated in saline or buffers for neutralizing internal acid conditions or may be administered without any carriers.

Pharmaceutical preparations that can be used orally include push fit capsules made of gelatin, as well as soft, sealed capsules made of gelatin and a plasticizer, such as glycerol or sorbitol. The push fit capsules can contain the active ingredients in admixture with filler such as lactose, binders such as starches, and/or lubricants such as talc or magnesium stearate and, optionally, stabilizers. In soft capsules, the active agents may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. Formulations for oral administration are typically in dosages suitable for such administration.

For buccal administration, the compositions may take the form of tablets or lozenges formulated in conventional manner.

For administration by inhalation, agents (e.g., antisense nucleic acids) for use according to the present disclosure may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The agents (e.g., antisense nucleic acids), when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of agents (e.g., antisense nucleic acids) in water-soluble form. Additionally, suspensions of agents may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the agents to allow for the preparation of highly concentrated solutions. Alternatively, agents (e.g., antisense nucleic acids) may be in powder form for constitution with a suitable vehicle, e.g., sterile pyrogen-free water, before use. Agents (e.g., antisense nucleic acids) may also be formulated in rectal or vaginal compositions such as suppositories or retention enemas, e.g., containing conventional suppository bases such as cocoa butter or other glycerides.

Other delivery systems can include time-release, delayed release or sustained release delivery systems. Such systems can avoid repeated administrations of the agents (e.g., antisense nucleic acids), increasing convenience to the subject and the physician. Many types of release delivery systems are available. They include polymer base systems such as poly(lactide glycolide), copolyoxalates, polycaprolactones, polyesteramides, polyorthoesters, polyhydroxybutyric acid, and polyanhydrides. Delivery systems also include non-polymer systems that are: lipids including sterols such as cholesterol, cholesterol esters and fatty acids or neutral fats such as mono, di, and tri glycerides; hydrogel release systems; silastic systems; peptide-based systems; wax coatings; compressed tablets using conventional binders and excipients; partially fused implants; and others disclosed herein.

Analytical Methods

In some aspects, the disclosure relates to the methods for detecting presence of a mutation causing an insertion in between exon 44 and exon 45 of the DYSF gene. In some embodiments, a clinical sample is obtained from a subject for the purpose of identifying a mutation. As used herein, a clinical sample refers to a specimen of biological matter obtained from a subject for the purpose of analysis or diagnosis. Non-limiting examples of clinical samples include blood, saliva, urine, feces, tissue, semen, cerebral spinal fluid, nucleic acids, epithelial cells, sweat, tears, hair and mucous.

In some embodiments, a clinical sample may be obtained from the blood of the patient. In some embodiments, a clinical sample may be obtained from the cells in the blood of a subject. In some embodiments, the cells may be blood cells. In some embodiments, the cells may be monocytes. In some embodiments, a clinical sample may be obtained from the tissue of a subject. In some embodiments, the tissue of the subject is muscle tissue. In some embodiments, the muscle tissue comprises skeletal muscle. In some embodiments, the muscle tissue comprises smooth muscle. In some embodiments, the muscle tissue comprises cardiac tissue. In some embodiments the clinical sample is obtained from a tissue that is not a muscle tissue. In some embodiments the non-muscle tissue comprises mesenchymal cells. In some embodiments, the tissue of the subject is skin tissue. In some embodiments, the non-muscle tissue comprises fibroblasts.

In some embodiments, a non-muscle tissue comprises stem cells, including, for example, embryonic stem cells, tissue stem cells, umbilical cord stem cells, mesenchymal stem cells, induced pluripotent stem cells, multipotent stem cells, totipotent stem cells, unipotent stem cells, progenitor cells, blastocysts, bone marrow stromal cells, hematopoietic stem cells, oligopotent stem cells, neural stem cells, and trophoblast stem cells.

In some embodiments, methods may involve genotyping a subject with respect to the human DYSF gene for purposes of selecting an appropriate treatment for the subject. For example, a subject may be administered an antisense nucleic acid disclosed herein if it is determined that the subject has a DYSF gene having a mutation that results an in-frame pseudoexon being coded for between exons 44 and 45 (e.g., a c.4886+1249 (G>T) mutation.) Often the subject has or is suspected of having muscular dystrophy (e.g., of the Miyoshi Myopathy-type) caused by abnormal expression of the dysferlin gene product.

The genotype of the subject may be assessed using a hybridization assay that discriminates between the presence of a guanosine and a thymidine at position c.4886+1249 of the human DYSF gene. An example of a suitable hybridization is a polymerase chain reaction (PCR) based allelic discrimination assay. A PCR based assay may be performed, for example, by using a primers that are at least partially complementary with a nucleic acid having a sequence as set forth in SEQ ID NO: 116, 117, 118, 119, 120, or 121 or a complementary sequence thereof together with a suitable probe for detecting presence or absence of a particular mutation. In some embodiments, a primer and probe of Table 3 is used. In some embodiments, one or more PCR amplicons may be sequenced and the obtained sequence may be evaluated for purposes of detecting presence or absence of a particular mutation. In some embodiments, a pair of primers disclosed in Table 1, 2 or 5 may be used to amplify one or more regions of the DYSF gene for purposes of determining the sequence of the DYSF and/or detecting presence or absence of a particular mutation in the DYSF gene.

In some aspects, the disclosure relates to the methods for detecting presence of a pseudoexon peptide insertion in between exon 44 and exon 45 of the DYSF gene (e.g., the peptide encoded by PE44.1). In some embodiments, the peptide insertion is detected by an immunoassay, such as an ELISA or Western blot. However, other protein detection assays may be used such as immunohistochemistry, immunocytochemistry, radioimmunoassays, or peptide sequencing by mass spectroscopy. In some embodiments, the immunoassay is probed with an anti-PE44.1 antibody. Antibodies against a mutant DYSF protein can target any region, for example the N-terminus or C-terminus, of the protein. In some embodiments, an antibody (e.g., an anti-PE44.1 antibody) targets a peptide encoded by the PE44.1 pseudo exon. In some embodiments an anti-PE44.1 antibody targets the C-terminal portion of the peptide encoded by the PE44.1 pseudoexon. In some embodiments, an anti-PE44.1 antibody targets SEQ ID NO: 116.

As used herein, the term "antibody" refers to an immunoglobulin, whether natural or wholly or partially synthetically produced. All derivatives thereof which maintain specific binding ability are also included in the term. The term also covers any protein having a binding domain which is homologous or largely homologous to an immunoglobulin binding domain. These proteins may be derived from natural sources, or partly or wholly synthetically produced. An antibody may be monoclonal or polyclonal. The antibody may be a member of any immunoglobulin class, including any of the human classes: IgG, IgM, IgA, IgD, and IgE. Derivatives of the IgG class, however, are preferred in the present invention.

The term "antigen binding fragment" or "antibody fragment" refers to any derivative of an antibody which is less than full-length. In some embodiments, the antibody fragment retains at least a significant portion of the full-length antibody's specific binding ability. Examples of such fragments include, but are not limited to, Fab, Fab', F(ab')$_2$, scFv, Fv, dsFv diabody, and Fd fragments. The antibody fragment may be produced by any appropriate means. For instance, the antibody fragment may be enzymatically or chemically produced by fragmentation of an intact antibody or it may be recombinantly produced from a gene encoding the partial antibody sequence. Alternatively, the antibody fragment may be wholly or partially synthetically produced. The antibody fragment may optionally be a single chain antibody fragment. Alternatively, the fragment may comprise multiple chains which are linked together, for instance, by disulfide linkages. The fragment may also optionally be a multimolecular complex. A functional antibody fragment will typically comprise at least about 50 amino acids and more typically will comprise at least about 200 amino acids.

Single-chain Fvs (scFvs) are recombinant antibody fragments consisting of only the variable light chain ($V_L$) and variable heavy chain ($V_H$) covalently connected to one another by a polypeptide linker. Either $V_L$ or $V_H$ may be the NH$_2$-terminal domain. The polypeptide linker may be of variable length and composition so long as the two variable domains are bridged without serious steric interference. Typically, the linkers are comprised primarily of stretches of glycine and serine residues with some glutamic acid or lysine residues interspersed for solubility.

An Fv fragment is an antibody fragment which consists of one $V_H$ and one $V_L$ domain held together by noncovalent interactions. The term dsFv is used herein to refer to an Fv with an engineered intermolecular disulfide bond to stabilize the $V_H$-$V_L$ pair.

A F(ab'), fragment is an antibody fragment essentially equivalent to that obtained from immunoglobulins (typically IgG) by digestion with an enzyme pepsin at pH 4.0-4.5. The fragment may be recombinantly produced.

A Fab fragment is an antibody fragment essentially equivalent to that obtained by reduction of the disulfide bridge or bridges joining the two heavy chain pieces in the F(ab'), fragment. The Fab' fragment may be recombinantly produced.

A Fab fragment is an antibody fragment essentially equivalent to that obtained by digestion of immunoglobulins (typically IgG) with the enzyme papain. The Fab fragment may be recombinantly produced. The heavy chain segment of the Fab fragment is the Fd piece.

Cells

In some aspects, the present disclosure relates to the delivery of antisense nucleic acids (e.g. oligonucleotides) to a target cell. In some embodiments, the cell is of a subject having a DYSF gene containing a c.4886+1249 (G>T) mutation. The cell may be heterozygous for the mutated gene or may be homozygous. The cell may have a second DYSF gene (a second allele of the gene) encoding a wild-type DYSF protein. The cell may have a second DYSF gene (a second allele of the gene) having a different mutation than the c.4886+1249 (G>T) mutation. For example, the cell may contain a DYSF gene comprising a mutation that causes a premature stop codon (e.g., within a region encoding the C2D domain of DYSF protein). For example, the premature stop codon may be a c.3444_3445delTGinsAA mutation. The cell to which the antisense nucleic acid is delivered may be in vitro or in vivo.

In some embodiments, the cell is a mammalian cell. In some embodiments the mammalian cell is a human cell. The cell may be from a subject having a muscular dystrophy that is associated at least in part with the DYSF gene comprising the c.4886+1249 (G>T) mutation. For example, the muscular dystrophy is of the Miyoshi Myopathy-type, or other muscular dystrophy caused by abnormal expression of the dysferlin gene product. In some embodiments, the cell is a myoblast or other muscle progenitor cell. In some embodiments, the cells are muscle cells. In some embodiments of the disclosure the muscle cells are striated (e.g. skeletal) muscle cells (e.g., myotubes). In some embodiments, the muscle cells are cardiac smooth muscle cells. In some embodiments, the muscle cells are smooth muscle cells. In some embodiments the cells are not muscle cells. In some embodiments, cells are of the brain, heart, kidneys, lungs, uterus, spleen, pancreas or muscle tissue of a subject. In some embodiments, the cell is a non-human cell (e.g., a non-human mammalian cell, e.g., a mouse cell). For example, the cell may be a non-human cell (e.g., a mouse cell) engineered to contain one or more copies of the human DYSF gene comprising the c.4886+1249 (G>T) mutation.

Pharmaceutical Compositions

According to some aspects of the disclosure, compositions are provided that comprise an agent (e.g., an antisense nucleic acid (e.g., an oligonucleotides) or vector comprising the same) and a carrier. As used herein, the term, "carrier" refers to an organic or inorganic ingredient, natural or synthetic, with which the active ingredient is combined to facilitate an intended use. For example, pharmaceutical compositions are provided that comprise an antisense nucleic acid and a pharmaceutically-acceptable carrier. As used herein the term "pharmaceutically acceptable carrier" refers to a carrier that is suitable for pharmaceutical administration. The term pharmaceutically-acceptable carrier includes compatible solid or liquid fillers, diluents or encapsulating substances that are suitable for administration to a human or other vertebrate animal.

Components of pharmaceutical compositions also are capable of being commingled with the agents of the present disclosure, and with each other, in a manner such that there is no interaction that would substantially impair the desired pharmaceutical efficiency. Pharmaceutical compositions may include solvents, dispersion media, coatings, antibacterial and antifungal s, isotonic and absorption delaying agents, and other suitable components compatible with pharmaceutical administration. Supplementary active agents can also be incorporated into the compositions. Active ingredients (e.g., oligonucleotides) may be admixed or compounded with any conventional, pharmaceutically acceptable carrier or excipient. Pharmaceutical compositions are generally sterile and prepared using aseptic technique. A sterile phosphate-buffered saline is one example of a pharmaceutically acceptable carrier. Other suitable carriers may be used. Pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Antisense nucleic acids may be administered per se (neat) or in the form of a pharmaceutically acceptable salt. When used in medicine the salts are generally pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

The compositions may conveniently be presented in unit dosage form and may be prepared by any of the methods well known in the art of pharmacy. All methods include the step of bringing the agents into association with a carrier that constitutes one or more accessory ingredients. In general, the compositions are prepared by uniformly and intimately bringing the agents into association with a liquid carrier, a finely divided solid carrier, or both, and then, if necessary, shaping the product. Liquid dose units are vials or ampoules. Solid dose units are tablets, capsules and suppositories.

An effective amount, also referred to as a therapeutically effective amount, of an antisense nucleic acid (e.g. oligonucleotide) capable of modulating splicing in a cell in which the DYSF gene is expressed is an amount sufficient to ameliorate at least one adverse effect associated with expression, or reduced expression, of the gene in a cell or in an individual in need of such modulation. The therapeutically effective amount to be included in pharmaceutical compositions may be selected based upon several factors, e.g., the type, size and condition of the patient to be treated, the intended mode of administration, the capacity of the patient to incorporate the intended dosage form, etc.

In some cases, antisense nucleic acids may be prepared in a colloidal dispersion system. Colloidal dispersion systems include lipid-based systems including oil-in-water emulsions, micelles, mixed micelles, and liposomes. An example of a colloidal system that may be used in methods provided herein is a liposome. Liposomes are artificial membrane vessels that are useful for delivering antisense nucleic acids in vivo or in vitro. It has been shown that large unilamellar vesicles can encapsulate large macromolecules. Nucleic acids and other components (e.g., viral vectors) can be encapsulated within the aqueous interior and be delivered to cells in a biologically active form. Liposomes may be targeted to a particular tissue by coupling the liposome to a specific ligand such as a monoclonal antibody, sugar, glycolipid, or protein. Ligands which may be useful for targeting a liposome to, for example, a smooth muscle cell or skeletal muscle cell include, but are not limited to: intact or fragments of molecules that interact with muscle cell specific receptors and molecules, such as antibodies, which interact with the cell surface markers. Lipid formulations for transfection are commercially available from QIAGEN, for example, as EFFECTENE™ (a non-liposomal lipid with a special DNA condensing enhancer) and SUPERFECT™ (a dendrimeric technology). Liposomes are commercially available from Invitrogen, Life Technologies, for example, as LIPOFECTIN™, which is formed of cationic lipids such as N-[1-(2, 3 dioleyloxy)-propyl]-N, N, N-trimethylammonium chloride (DOTMA) and dioleoyl phophotidylethanolamine (DOPE), as well as other lipid-based reagents including Lipofectamine and Oligofectamine. Certain cationic lipids, including in particular N-[1-(2, 3 dioleoyloxy)-propyl]-N,N,N-trimethylammonium methyl-sulfate (DOTAP), may be advantageous when combined with the antisense nucleic acids (e.g. oligonucleotides) analogs of the disclosure.

In one embodiment, antisense nucleic acids may be formulated with a biocompatible microparticle or implant that is suitable for implantation or administration to a recipient. Bioerodible implants may include a biodegradable polymeric matrix, for example, for containing an exogenous expression construct engineered to express an antisense nucleic acid under the control of an appropriate promoter. The polymeric matrix can be used to achieve sustained release of the therapeutic agent in the subject. A polymeric matrix may be in the form of a microparticle such as a microsphere, in which an antisense nucleic acid and/or other therapeutic agent is dispersed throughout a solid polymeric matrix, or a microcapsule, in which antisense nucleic acid and/or other therapeutic agent is stored in the core of a polymeric shell. Other forms of the polymeric matrix for containing a therapeutic agent include films, coatings, gels, implants, and stents. The matrix composition also can be selected not to degrade, but rather, to release by diffusion over an extended period of time. In some embodiments, antisense nucleic acids are administered to the subject via an implant while the other therapeutic agent is administered.

Both non-biodegradable and biodegradable polymeric matrices can be used to deliver antisense nucleic acids (e.g, oligonucleotides) and/or the other therapeutic agent to a subject. Biodegradable matrices are preferred. Such polymers may be natural or synthetic polymers. The polymer is selected based on the period of time over which release is desired, generally in the order of a few hours to a year or longer. Typically, release over a period ranging from between a few hours and three to twelve months may be used. A polymer may be in the form of a hydrogel, e.g., a hydrogel that can absorb up to about 90% of its weight in water and which is optionally cross-linked with multi-valent ions or other components, e.g., polymers.

Other exemplary compositions that can be used to facilitate uptake of a nucleic acid include calcium phosphate and other chemical mediators of intracellular transport, micro-injection compositions, electroporation and homologous recombination compositions (e.g., for integrating a nucleic acid into a preselected location within the target cell chromosome).

In addition to the formulations described previously, the agents may also be formulated as a depot preparation. Such long-acting formulations may be formulated with suitable polymeric or hydrophobic materials (for example as an emulsion in an acceptable oil) or ion exchange resins, or as sparingly soluble derivatives, for example, as a sparingly soluble salt.

Other suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems.

Kits

Agents (e.g., antisense nucleic acids) described herein may, in some embodiments, be assembled into pharmaceutical or diagnostic or research kits to facilitate their use in therapeutic, diagnostic or research applications. A kit may include one or more containers housing the components and instructions for use. Specifically, such kits may include one or more agents (e.g., antisense nucleic acids) described herein, along with instructions describing the intended therapeutic application and the proper administration of these agents. In certain embodiments agents in a kit may be in a pharmaceutical formulation and dosage suitable for a particular application and for a method of administration of the agents.

The kit may be designed to facilitate use of the methods described herein by physicians and can take many forms. Each of the agents of the kit, where applicable, may be provided in liquid form (e.g., in solution), or in solid form, (e.g., a dry powder). In certain cases, some of the compositions may be constitutable or otherwise processable (e.g., to an active form), for example, by the addition of a suitable solvent or other species (for example, water or a cell culture medium), which may or may not be provided with the kit. As used herein, "instructions" can define a component of instruction and/or promotion, and typically involve written instructions on or associated with packaging of the disclosure. Instructions also can include any oral or electronic instructions provided in any manner such that a user will clearly recognize that the instructions are to be associated with the kit, for example, audiovisual (e.g., videotape, DVD, etc.), Internet, and/or web-based communications, etc. The written instructions may be in a form prescribed by a governmental agency regulating the manufacture, use or sale of pharmaceuticals or biological products, which instructions can also reflects approval by the agency of manufacture, use or sale for human administration.

The kit may contain any one or more of the components described herein in one or more containers. As an example, in one embodiment, the kit may include instructions for mixing one or more components of the kit and/or isolating and mixing a sample and applying to a subject. The kit may include a container housing agents described herein. The agents may be in the form of a liquid, gel or solid (powder). The agents may be prepared sterilely, packaged in syringe and shipped refrigerated. Alternatively it may be housed in a vial or other container for storage. A second container may have other agents prepared sterilely. Alternatively the kit may include the active agents premixed and shipped in a syringe, vial, tube, or other container. The kit may have one or more or all of the components required to administer the agents to a patient, such as a syringe, topical application devices, or IV needle tubing and bag.

The kit may have a variety of forms, such as a blister pouch, a shrink wrapped pouch, a vacuum sealable pouch, a sealable thermoformed tray, or a similar pouch or tray form, with the accessories loosely packed within the pouch, one or more tubes, containers, a box or a bag. The kit may be sterilized after the accessories are added, thereby allowing the individual accessories in the container to be otherwise unwrapped. The kits can be sterilized using any appropriate sterilization techniques, such as radiation sterilization, heat sterilization, or other sterilization methods known in the art. The kit may also include other components, depending on the specific application, for example, containers, cell media, salts, buffers, reagents, syringes, needles, a fabric, such as gauze, for applying or removing a disinfecting agent, disposable gloves, a support for the agents prior to administration etc.

EXAMPLES

Example 1: Materials and Methods

Patients.

Two Miyoshi myopathy patients (ID#8597, 8601, designated herein as P1 and P2, respectively) are siblings that exhibited typical MM disease symptom onset and progression. They do not express dysferlin in either their muscles or monocytes and exome sequencing determined that they are heterozygous for a nonsense mutation in dysferlin exon 32 (c.3444_3445delTGinsAA) that causes a premature stop codon within the C2D domain. Further sequencing analyses failed to identify a second pathogenic allele, suggesting that this mutation lies within non-coding regions of the gene. Dermal fibroblasts and blood were collected from these patients and their immediate relatives for DNA analyses and the fibroblasts were used to develop myogenic cell culture lines.

DNAs from 112 unrelated patients representing 81 pedigrees clinically diagnosed with MM or LGMD2B, and from an additional 724 random individuals, (either clinically normal or with non-related conditions) were used in these studies. In the second phase of the study, samples from eight unrelated MM patients who were DYSF negative in monocyte assays and for whom at least one of the pathogenic DYSF mutations had not been identified by exon sequencing, were tested.

Cell Cultures.
Dermal Fibroblast Cultures.

Patient skin biopsies were obtained with informed consent and cultured as explants in RPMI Medium (RPMI1640 (GIBCO) or DMEM Medium (DMEM Glutamax with pyruvate (GIBCO)), each containing 15% FBS (Sigma), 100 units/ml penicillin, 100, µg/ml streptomycin and 0.25 µg/ml Fungizone (Gibco)) to generate fibroblast lines. These were later routinely passaged in DMEM Fibroblast Growth Medium (GM) (DMEM, 15% FBS, 1× Non-Essential Amino Acids (GIBCO), 10 mM HEPES (GIBCO). Normal adult human dermal fibroblasts were obtained from Lonza, ATCC, and Lifeline Cell Technology (termed NHDF-1, -2, and -3, respectively).

Myogenic Conversion of Dermal Fibroblasts and Myoblast Lines.

Immortalized inducible fibroblast-derived myogenic (iFDM) cell cultures were established from patient and normal NHDF fibroblast lines using methods described. Fibroblasts were transduced with a tamoxifen-inducible MyoD lentivirus (Lv-CMV-MyoD-ER(T), Addgene). These cells proliferate as fibroblasts until induced to express MyoD by 4-hydroxytamoxifen (TMX) treatment (5 µM TMX (Sigma, H-7904) in GM for 1 day followed by 3 days in 1 µM TMX in differentiation medium (DM) (DMEM Glutamax with pyruvate: Medium 199 (Gibco) (3:1), 2% horse serum (HyClone), 20 mM HEPES, and 20 µg/ml insulin, 11 µg/ml transferrin, 1.3 µg/ml selenium (2× ITS, Gibco), replacing DM every third day. In initial experiments TMX was added throughout the differentiation period, but equivalent differentiation was observed with 3 days of treatment, so the TMX induction in DM was shortened to 3 days. Some fibroblasts were also immortalized by transduction with an hTERT lentiviral vector (Lv-CMV-hTERT-IRES-Puro, UCLA Vector Core) prior to myogenic conversion with the MyoD lentivirus, extending the proliferative potential of these cells. Applicants have also obtained a myoblast cell line (01Ubic-CT2 ("UBic")) derived from normal human biceps muscle and immortalized by transduction with hTERT and CDK4 retroviruses to generate an unrestricted supply of 'normal' myogenic cells.

Figure 7:
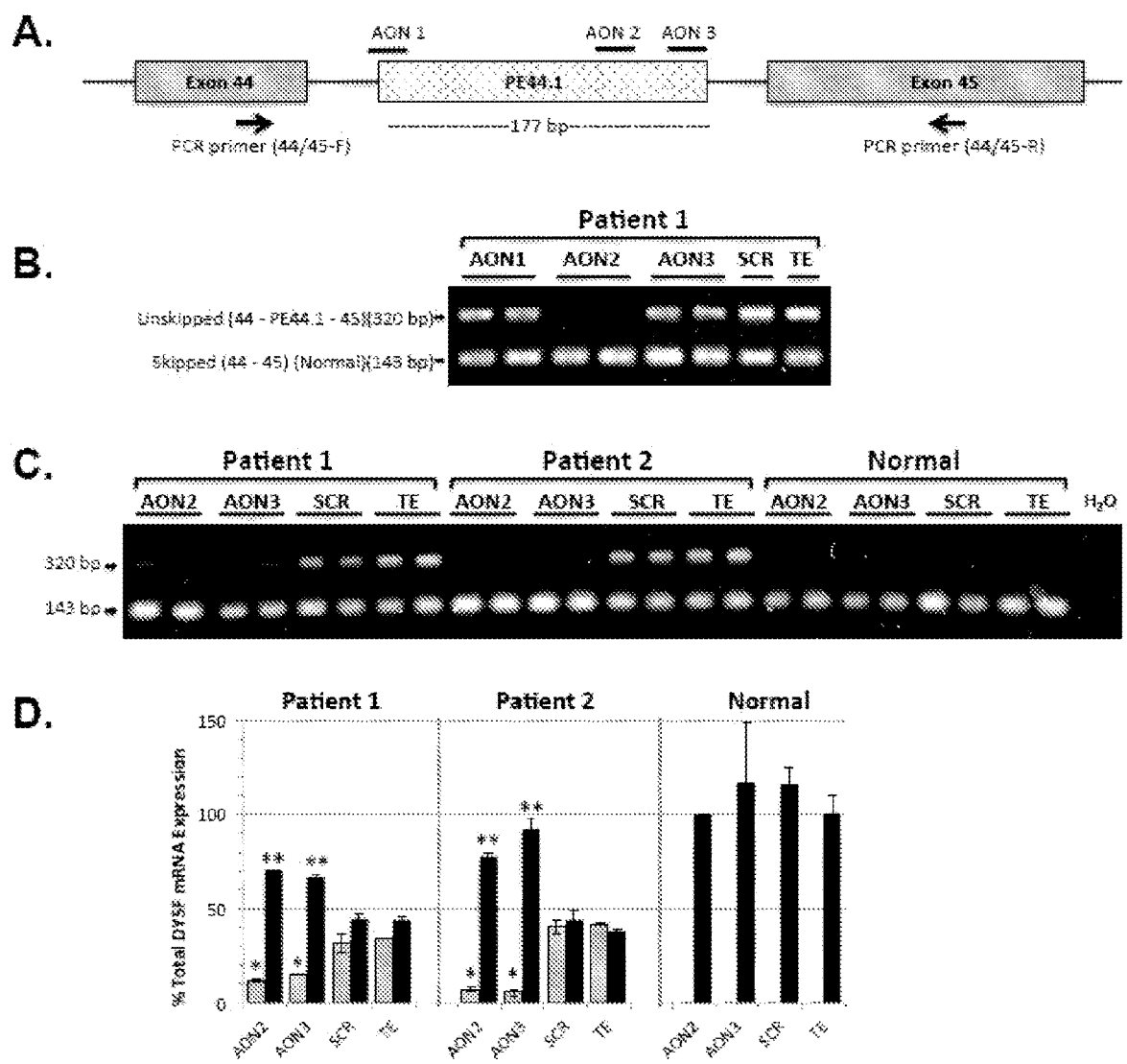
FIG. 7. Antisense oligonucleotide-mediated skipping of PE44.1 in iFDM cells from patients P1 and P2. (A) AON1, AON2 and AON3 (see Table 4) target potential exonic splicing enhancers in PE44.1 in the areas shown. Primers within exon 44 and 45 were used to amplify cDNAs from iFDMs treated with AONs to distinguish normal mRNA transcripts (143 bp product containing exon 44+45) from mutant PE44.1 transcripts (320 bp product containing exon 44+PE44.1+45). (B) iFDM cells from Patient P1 treated with AON2 and AON3 (duplicate cultures for each) expressed reduced amounts of PE44.1 mutant mRNA and slightly higher normal DYSF mRNA compared with AON1-treated, non-specific scrambled (SCR) AON-treated or TE treated cells, which showed approximately equal proportions of mutant PE44.1 and normal mRNAs. (C) A separate experiment using patient P1, P2 and normal iFDMs (duplicate cultures for each treatment) showed that AON2 and AON3 treatments again reduced PE44.1 mutant mRNA expression and increased the relative abundance of normal DYSF mRNA. As expected, normal iFDMs only expressed normal DYSF transcripts. (D) Quantitative RT-PCR analysis of the same RNAs in panel C show that treatment if patient iFDMs with AON2 and AON3 significantly reduces the expression of the mutant transcripts (gray bars, mean±SD, *$p<0.05$) and increases expression of the normal transcripts (black bars, mean±SD, **, $p<<0.05$) compared to SCR and TE controls. The relative expression of each form is calculated using the amplification of a PCR product spanning the exon 50/51 junction as representative of 100% DYSF expression.
Figure 9:
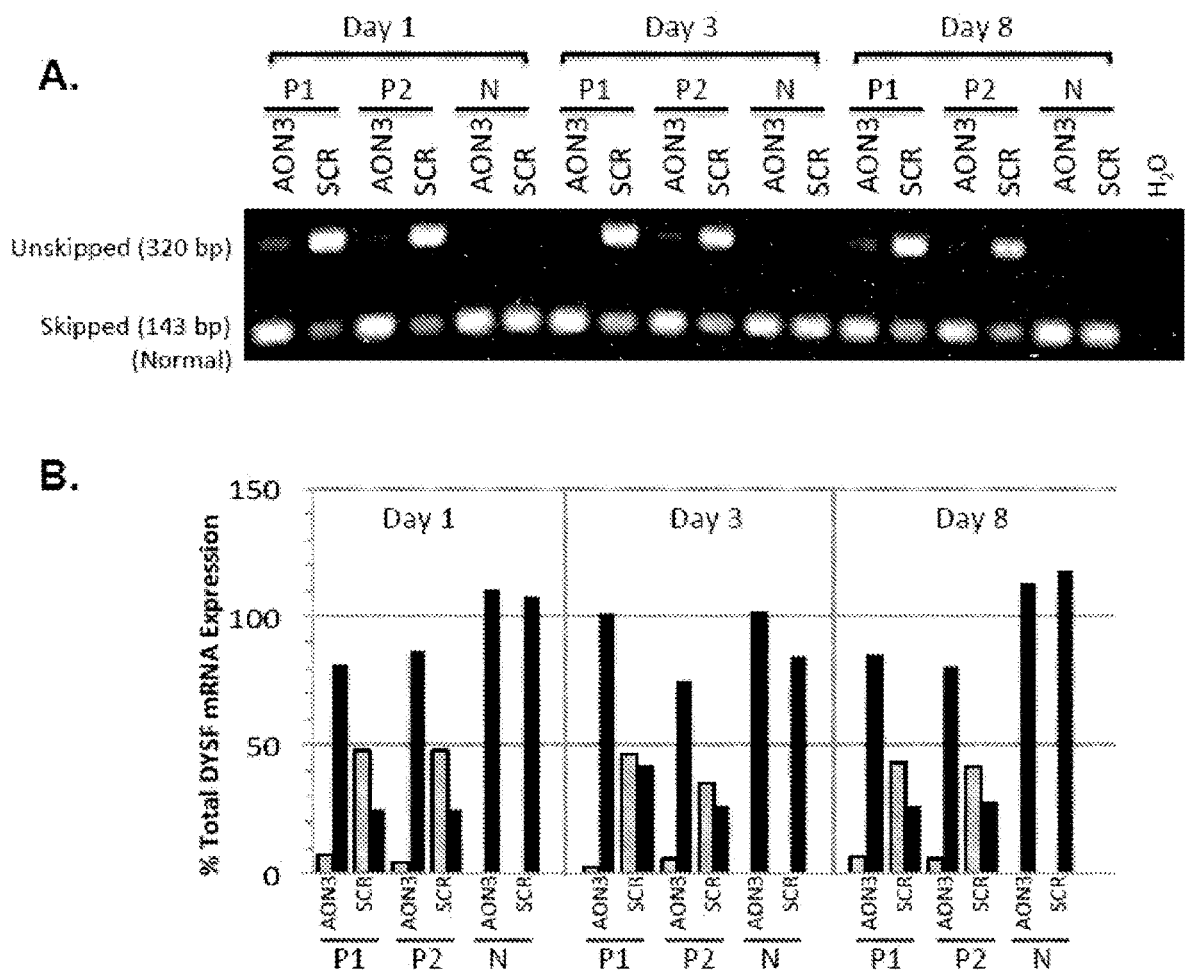
FIG. 9. AON3 treatment of patient iFDMs alters expression of DYSF PE44.1 mutant and normal mRNA splice forms at 1, 3 and 8 days after AON addition. (A) RT-PCR analysis of mRNA from cultures collected in parallel with those in FIG. 8 show that treatment if Patient 1 (P1) and Patient 2 (P2) iFDMs with AON3 reduces the expression of the PE44.1 mutant transcript and increases normal transcript expression. Normal iFDMs (N) express only the normal DYSF form, not affected by AON treatments. (B) Quantitative RT-PCR analysis of the same mRNAs confirms the effects of AON3 treatment. (PE44.1 mutant transcript expression: gray bars; normal transcript expression: black bars). The relative expression of each form is calculated using exon 50/51 amplicon levels as 100% DYSF expression as in FIG. 7.

As shown in FIGS. 7 and 9, AON-mediated PE44.1-skipping can be induced in the differentiated iFDM cells from patient fibroblasts (P1 and P2). In these experiments using standard and quantitative RT-PCR to evaluate mRNA transcripts, treatment with AONs (e.g., AONs 2 and 3) led to a significant reduction of PE44.1 containing transcripts to ~15-45% that found in control SCR or TE-treated cells, accompanied by a significant (~50-100%) increase in the normal transcript levels. These results illustrate an in vitro model with which a functional impact of AON-mediated DYSF PE44.1-skipping on patients' cells may be evaluated, for example.

Immunocytochemistry.

Differentiated iFDM cells were fixed with 4% paraformaldehyde then for 10 min. then permeabilized and immunostained using anti-myosin heavy chain antibody (MF20, monoclonal supernatant 1/10 dil., Developmental Studies Hybridoma Bank) and detected with Alexa 488 anti-mouse IgG (Invitrogen) and Hoechst 33258 to stain nuclei with methods as described.

Protein Analysis.

Proteins were extracted from differentiated iFDM cells using RIPA buffer (40 mM Tris-HCl pH 8, 150 mM sodium chloride 1% Triton X—100, 0.5% sodium deoxycholate, 0.5% SDS) with protease inhibitors (cOmplete. Roche) then a sample was quantified using a BCA protein assay (Thermo) (Thermo) assay. The remaining protein was heated at 70° C. in SDS-PAGE Laemmli sample buffer 10 min, then 10 ug protein was separated on 7.5% SDS-PAGE gels and blotted onto nitrocellulose filters using an iBlot Gel Transfer Device (Life Technologies, program P3 for 10 min.) and analyzed by western immunostaining using LI-COR Odyssey blocking reagent and methods. Primary antibodies included and anti-dysferlin specific for the C-terminal end (NCL-Hamlet, Leica, 1/1000) or N-terminal end (Romeo, JAI-1-49-3, Abcam, 1/500), and anti-GAPHD (10R-G109a Fitzgerald, 1/1000). Blots were quantitatively analyzed using a LI-COR Odyssey infrared imager.

Nucleic Acid Purification And Reverse Transcription.

Genomic DNA and RNA were prepared from cells using Gentra Puregene (Qiagen) and TRIzol (Life Technologies) reagents, respectively and manufacturers protocols. RNA was DNAse digested (TURBO DNA-Free, Ambion), to remove DNA contaminants then 0.2-2 ug RNA was reverse transcribed (High Capacity cDNA Reverse Transcription Kit (Applied Biosystems)) using manufacturers protocols.

PCR Amplification.

For RNA and cDNA analyses used DYSF mRNA variant 8 (NM_003494.3) was used as the reference sequence, as it is the predominant isoform in skeletal muscle. PCR primers were used to amplify and sequence the cDNA from patient and normal iFDM cells to determine whether the exon 32 (c.3444_3445delTGinsAA) mutant allele is expressed in these cells. The following primers were used: DYSF31-F (5'-GTGTGAACAGACCCACGAT-3') and DYSF33-R (5'-GTCGTACAGCTCCACCACAA3').

In some embodiments, to facilitate sequencing of a complete DYSF cDNA, a PCRTiler v1.42 program was used to design 17 primer sets to amplify ~500 bp cDNA segments that overlapped by ~50 bp and spanned the entire 6.9 kb DYSF cDNA (Table 1). cDNAs from cell cultures (corresponding to 40 ng input RNA) was amplified by PCR using Hotmaster Taq DNA polymerase (5 PRIME) as follows: 95° C. for 5 min., 30 cycles of 95° C. for 30 sec., 59.1° C. for 30 sec., 72° C. for 1 min., then 72° C. for 10 min. PCR products were analyzed by gel electrophoresis and amplified products were isolated and sequenced.

Similarly primers were designed (Table 2) to amplify through and sequence DYSF intron 44i using 20 ng of genomic DNA from patient cells and blood samples. The same PCR conditions were used.

Allelic Discrimination Assays.

TaqMan Probes were designed (Applied Biosystems) to distinguish normal and mutant alleles of the novel point mutation in intron 44i of the two MM patients (Table 3). These were used in PCR reactions (Taqman Genotyping Master Mix Kit, Applied Biosystems) to amplify 10 ng of genomic DNA from the two MM patients, their immediate family members, 112 unrelated patients representing 81 pedigrees with individuals clinically diagnosed with MM or LGMD2B. Of these, 16 pedigrees had DYSF mutations defined in both alleles and 3 had a mutation defined in only one allele. 724 DNA samples from a random population of normal individuals and those with unrelated diseases were also screened. PCR conditions were: 95° C. for 10 min., then 50 cycles of 92° C. for 15 sec., 60° C. for 1 min. PCR products were analyzed on a Bio-Rad CFX384 Touch Real-Time PCR Detection System using the allelic discrimination software.

Antisense Oligonucleotide Transfections.

The 44i mutation identified leads to inclusion of an in-frame pseudoexon that disrupts the normal DYSF protein sequence. Inhibiting the splicing of PE44.1 allows restored synthesis of normally spliced DYSF transcripts. AONS targeting ESE sequences within PE44.1 were designed that could enhance its inclusion in spliced mRNA, along with a non-specific scrambled AON that does not target this region (Table 4). These AONs were synthesized as 2'-O-methyl RNA with full-length phosphorothioate backbones (Integrated DNA Technologies). iFDM cells from patient P1, P2 and normal NHDF-2 fibroblasts were allowed to differentiate for 6-9 days to form myotubes. Cells were transfected with each AON (600 nM) (or TE buffer as control) using Oligofectamine (Life Technologies) and the manufacturer's protocol. At specific times after AON addition (1 to 8 days), RNA was extracted and expression of wild type and PE44.1 containing mutant RNA evaluated by RT-PCR using primers that distinguish the two mRNA forms based on amplicons size. For this primers were: DYSF44/45-F- and DYSF44/45-R (Table 5) 5', which generate a 143 bp amplicon from the normal cDNA (exon 44+45) and 320 bp amplicons from the mutant cDNA containing PE44.1 (exon 44+PE44.1+45). cDNAs (corresponding to 20 ng input RNA) were amplified using Hotmaster Taq DNA polymerase as follows: 94° C. for 2 min., 30 cycles of 94° C. for 20 sec., 58° C. for 20 sec., 65° C. for 1 min., then 65° C. for 10 min. PCR products were analyzed by gel electrophoresis.

For quantitative PCR (Q-PCR), cDNAs (corresponding to 20 ng input RNA) were amplified using primers (Table 5) that distinguish PE44.1-containing mutant (DYSF 44.1-Q F and R) RNA and normal DYSF 44/45-Q F.2 and R.2). Primers for GAPDH were used to normalize RNA levels. Primers specific to sequences spanning the junction of exons 50 and 51, present in all DYSF forms, were used to determine the total DYSF mRNA levels, and this served as the 100% DYSF expression value to approximate the relative expression of the mutant and normal exon 44/45 splice forms. For Q-PCR, DyNAmo HS SYBR Green qPCR Kit reagents were used (Thermo Scientific) and a Bio-Rad CFX384 C-1000 Touch Real-Time PCR Detection System. The PCR conditions were 95° C. for 15 min., 50 cycles of 94° C. for 10 sec., 58° C. for 30 sec., 72° C. for 30 sec., then 72° C. for 10 min. followed by melt curve analysis (65-95° C.) to ensure product quality.

Statistics. Statistical significance was evaluated using one-way ANOVA with post-hoc Tukey tests. Prism 5.0 statistical analysis software (GraphPad Software) was used.

Example 2: A Novel Deep Intronic Mutation in Dysferlin Leads to Expression of a Pseudoexon Miyoshi Myopathy Patients: Restoration of Normal DYSF mRNA Mediated by Antisense Oligonucleotides Identification of a Deep Intronic Mutation in DYSF Intron 44.

The two MM patients in our study, P1 and P2, do not express dysferlin in either their muscles or monocytes and exome sequencing determined that they are heterozygous for a nonsense mutation in dysferlin exon 32 (c.3444_3445delTGinsAA) that causes a premature stop codon within the C2D domain. Further exome sequencing analyses failed to identify a second pathogenic allele, suggesting that this mutation lies within non-coding regions of the gene. To identify the other mutant allele, a myogenic cell culture system was established with cells from the patients and normal controls. Myogenic cell lines were generated from dermal fibroblasts cultured from patient skin biopsies. The fibroblasts from patients, along normal control fibroblasts, were converted to inducible fibroblast-derived myogenic (iFDM) cell cultures by using lentiviral constructs to introduce a tamoxifen-inducible form of the myogenic regulator MyoD, which drives the myogenic program. In addition lines were immortalized by introducing lentiviral hTERT to extend their proliferative lifespan. Upon treatment of cells with TMX, resulting cultures contained numerous multinucleate myotubes and expressed differentiated muscle proteins such as myosin heavy chain as shown in FIG. 1A, and on very rare occasion were observed to spontaneously contract. These lines thus provide an unrestricted supply of patient-derived myogenic cells with a high capacity to differentiate.

Western blots containing protein from patient-derived iFDMs probed with C-terminal anti-dysferlin antibodies (NCL-Hamlet) showed low levels of dysferlin protein of apparently normal size (at approximately 20-40% the amount in normal iFDMs) (FIG. 1B). Similar results were obtained with anti-N-terminal dysferlin antibody (Romeo). Therefore, though dysferlin protein was not detected in muscles or monocytes from these patients, low levels of dysferlin protein are produced in these mutant cell cultures. The known mutation in these patients that causes a premature stop codon within exon 32 and could generate a truncated protein. A mutation in the second DYSF allele allows the synthesis of some protein of normal or near-normal size.

cDNA was prepared using RNA from differentiated iFDM cells from derived patients P1, P2 and normal control NHDF-2 fibroblasts. PCR primers were used that amplify the cDNA region around the known exon 32 mutation to determine whether transcripts carrying this mutation are expressed in the patient-derived iFDMs. Sequence analysis of amplified RT-PCR products showed that RNA did not contain exon 32 nonsense mutant sequence but rather contained only the wild-type sequence in this region, indicating that the DYSF mRNAs are produced only from the other unknown allele. The products of the exon 32 mutant allele are therefore likely degraded due to rapid nonsense-mediated decay mechanisms. To define the structure of the mRNA produced in the mutant iFDMs, PCR primer sets that generated 17 overlapping amplicons (Table 1) were used to sequence the 6.9 kb DYSF cDNA from these cells. Most of these primer sets generated amplicons of the same size using iFDM cDNAs from patients P1, P2 and normal cells (FIG. 2A, panels A, D). However, two of the overlapping primer sets revealed a novel amplification product only in patient cDNAs (FIG. 2A, panels B, C). Using additional PCR primers that flank this 44/45 junction, cDNAs from skeletal muscle biopsy tissue RNA were amplified from Patient 1 and an unrelated, non-symptomatic individual. As shown in FIG. 2B, very low amounts of DYSF transcripts are present in the patient's muscle tissue and include both mutant and normal splice forms as detected by the two amplification products (320 and 143 bp, respectively). Only the normal cDNA amplification product is observed in the normal control muscle.

Figure 3:
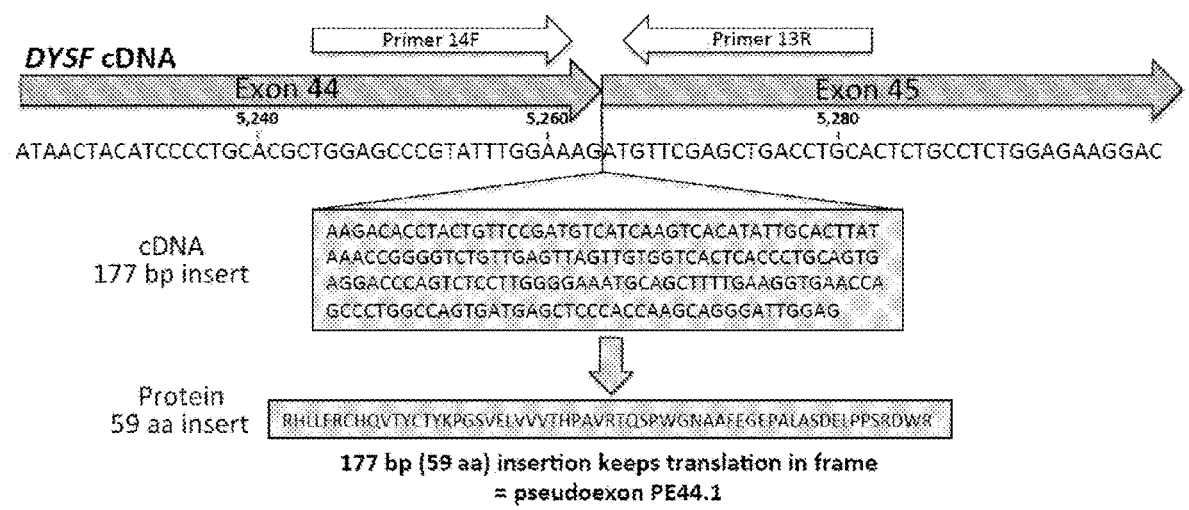
FIG. 3. cDNA sequencing shows that patients P1 and P2 have an insertion of insertion 177 nt at the junction of exons 44 and 45. This insertion maintains the reading frame and leads to inclusion of 59 additional amino acids in the protein sequence. The mRNA from these patients therefore contains a novel pseudoexon, PE44.1, spliced into the coding sequence.

Subsequent sequence analysis of these amplicons from each patient and control cDNAs revealed that the novel amplicons contained 177 bp of intron 44i sequence spliced into the cDNA at the exon 44 exon 45 junction, maintaining the normal reading frame (FIG. 3). As a result, 59 amino acids are inserted into the protein sequence. The patients therefore express a novel pseudoexon (PE), termed PE44.1, derived from sequences within DYSF 44i that are spliced into the mature transcript.

Figure 4:
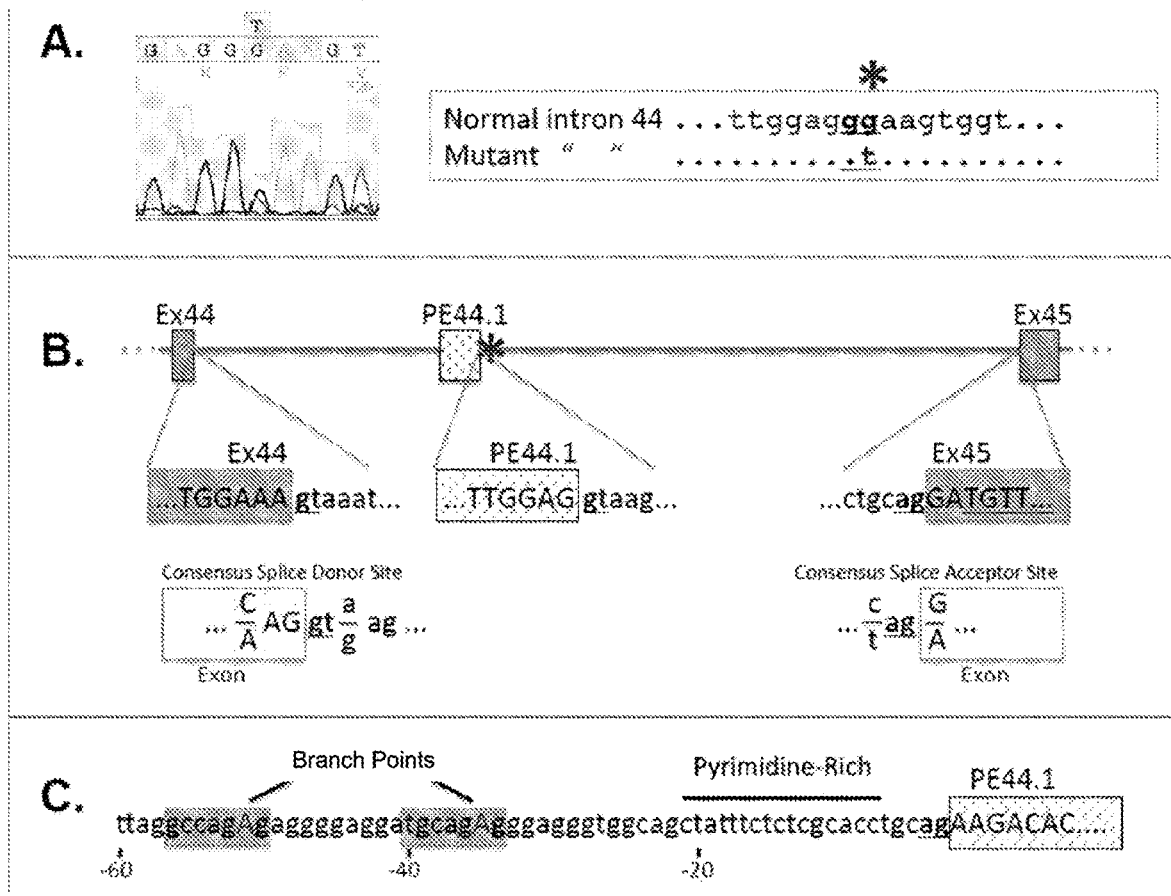
FIG. 4. A novel deep intronic point mutation leads to inclusion of PE44.1 in the mature mRNA of patients P1 and P2. (A) Genomic sequencing of DYSF intron 44i shows patients are heterozygous for a point mutation (c.4886+1249 (G>T)). The location of this 44i mutation, indicated with an asterisk (*), creates a novel splice donor consensus sequence at the 3' end of the PE44.1 sequence (B). (C) The intronic sequence upstream of PE44.1 contains additional consensus sites required for mRNA splicing including a splice acceptor site at the 5' end of PE44.1, an adjacent pyrimidine-rich region and two potential lariat branch point consensus sequences that could be used to promote splicing. These sequences, in the presence of (c.4886+1249 (G>T)) mutation, allow the new pseudoexon PE44.1 to be spliced between exons 44 and 45.

DYSF 44i region was sequence using genomic DNA from iFDMs and blood sample from both patients and compared it with the genomic NCBI reference sequence. Sequence analysis revealed a point mutation in both patients nearly midway in intron 44i (c.4886+1249 (G>T)) (FIG. 4A, B). This (G>T) mutation, which occurs 2 bp after the 3' end of the PE44.1 sequence, generates a consensus splice donor sequence at that site (FIG. 4B) that promote the aberrant splicing of PE44.1 into the mature transcript. Along with the novel splice donor site created by this (G>T) mutation, analysis of the intronic sequence upstream of PE44.1 reveals that other sequence elements required for splicing are also present in this region. As shown in FIG. 4C, there is a conserved splice acceptor site at the 5' end of PE44.1 along with a required pyrimidine-rich region immediately upstream and two potential lariat branch point sequences (as identified by Human Splicing Finder version 2.4.1, typically 2-50 bp upstream of the splice site). Therefore a multiple elements required by the splicing machinery are in place within this intronic region to allow the aberrant splicing of PE44.1 within the mRNA in the presence of this (G>T) point mutation.

In addition to the (c.4886+1249 (G>T)) mutation, 4 common sequence variants were identified in DYSF cDNA in patients P1 and P2 relative to the reference sequence (Table 6). Sequence analysis of DYSF intron 44i identified 6 additional polymorphisms (Table 7). All of these are common, previously identified polymorphisms not linked to disease.

Figure 2:
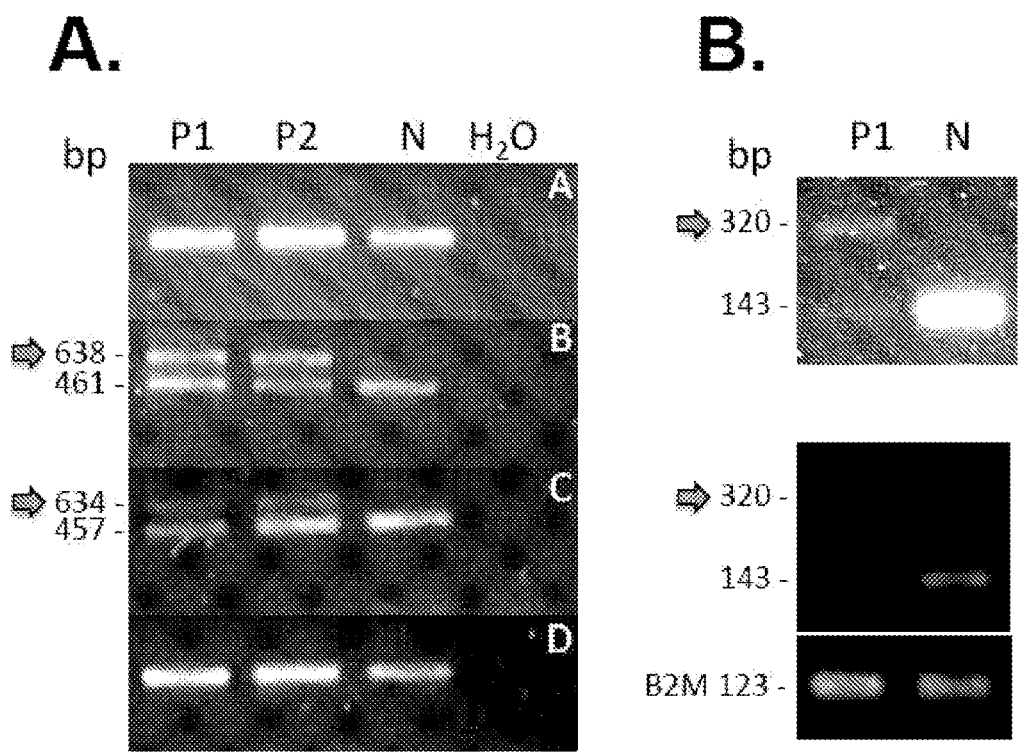
FIG. 2. (A) Identification of the DYSF intron 44i mutation. RT-PCR of cDNA from two patients (P1, P2) shows novel amplicons in patients (arrows) generated using with two primer sets (panels B, C) but not with any other sets (panels A, D), indicating the presence of additional sequence within the patient cDNA in the region amplified by primer sets used in panels B and C. The product was sequenced to identify the inserted sequence. (B) RT-PCR of cDNA from skeletal muscle tissue from patient P1 shows very low-level expression of DYSF mRNA compared to muscle from a normal control individual (N), and this includes mutant (320 bp) and wild-type (143 bp) transcripts for this locus detected by primers that flank the exon 44/45 junction. The top panel is a brighter gel exposure than the bottom two panels, allowing visualization of the PCR products in patient muscle. Lower two panels show the same exposure for both the DYSF and B2M loading control PCR products (123 bp).
Figure 5:
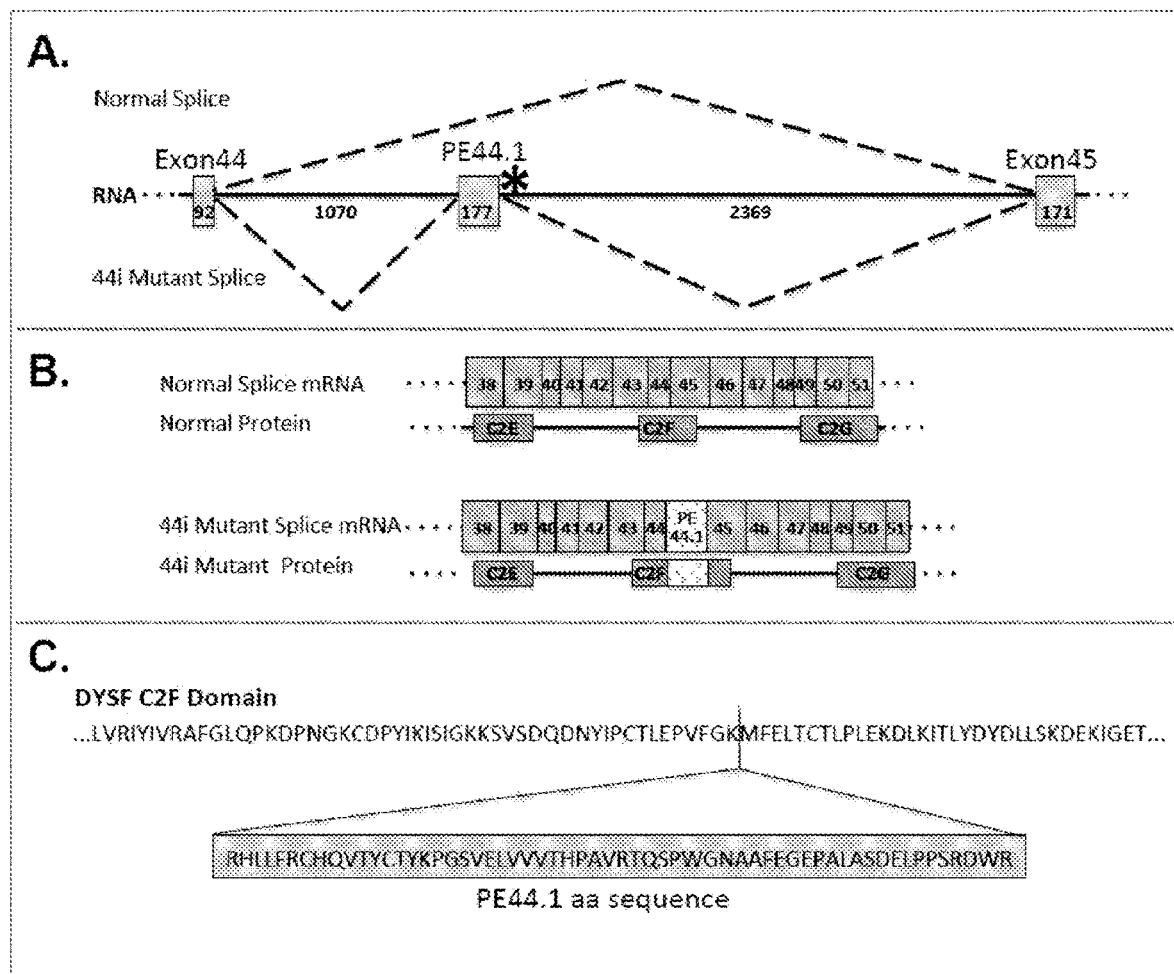
FIG. 5. Normal and mutant PE44.1 mRNA are expressed through alternative splicing of the DYSF transcripts. (A) The mRNA structure within the DYSF exon 44-intron 44i-exon 45 region is shown along with the normal and mutant splicing patterns. Numbers along the RNA indicate the size of each element in bp. The site of the 44i mutation (c.4886+1249 (G>T)) is indicated with an asterisk (*). (B, C) The normal and mutant splice product (including PE44.1) are shown (displaying the region of DYSF from exons 38-51). Also shown is the normal and mutant protein. PE44.1 results in a 59 amino acids insertion within the normal C2F domain (normally 84 aa), creating a large disruption in this region.

The alternate DYSF splice forms present in patients P1 and P2 cells are shown in FIG. 5A. Our cDNA amplification and sequencing results show that both normal and mutant PE44.1 mRNA splice forms are present in patient iFDM cells, typically present in approximately equal proportions (FIGS. 2, 7, 9). The impact of PE44.1 inclusion in the DYSF mRNA and protein is further shown in FIGS. 5B and C. DYSF exons 44-45 encode part of the conserved C2F domain of dysferlin. Insertion of the PE44.1 sequence leads to the in-frame insertion of 59 amino acids within the C2F domain and a large disruption of this domain that would significantly impair protein function. This 59 amino acid sequence is unique and not homologous to any other peptide or protein structure.

Pedigree Analysis.

Figure 6:
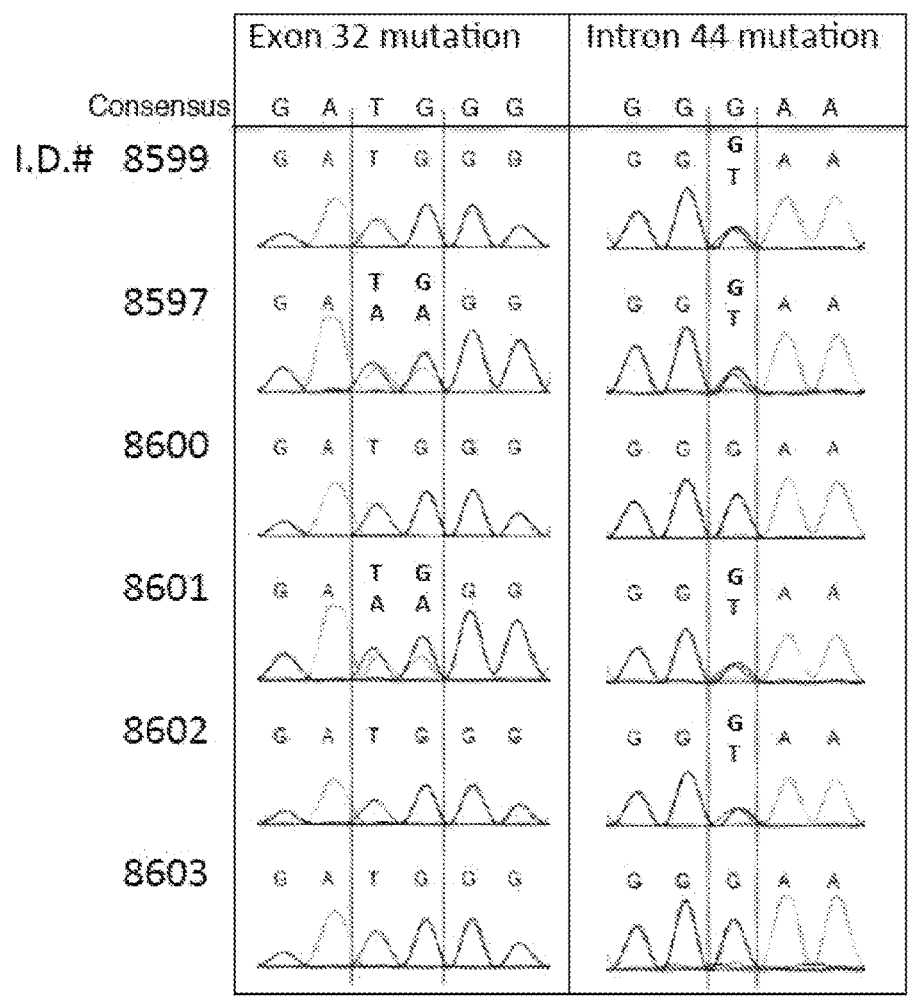
FIG. 6. Analysis of genomic DNA from four immediate relatives of patients P1 and P2 reveal the inheritance pattern of the two mutations in this family. (A) Genomic DNA from each family member (listed by global I.D.) was amplified and sequenced using primers flanking the previously known DYSF exon 32 mutation in these patients as well as the new DYSF 44i mutation associated with PE44.1 expression. Mutant nucleotides are shown in red. (B) Results show maternal inheritance of the DYSF 44i mutation.
Figure 6:
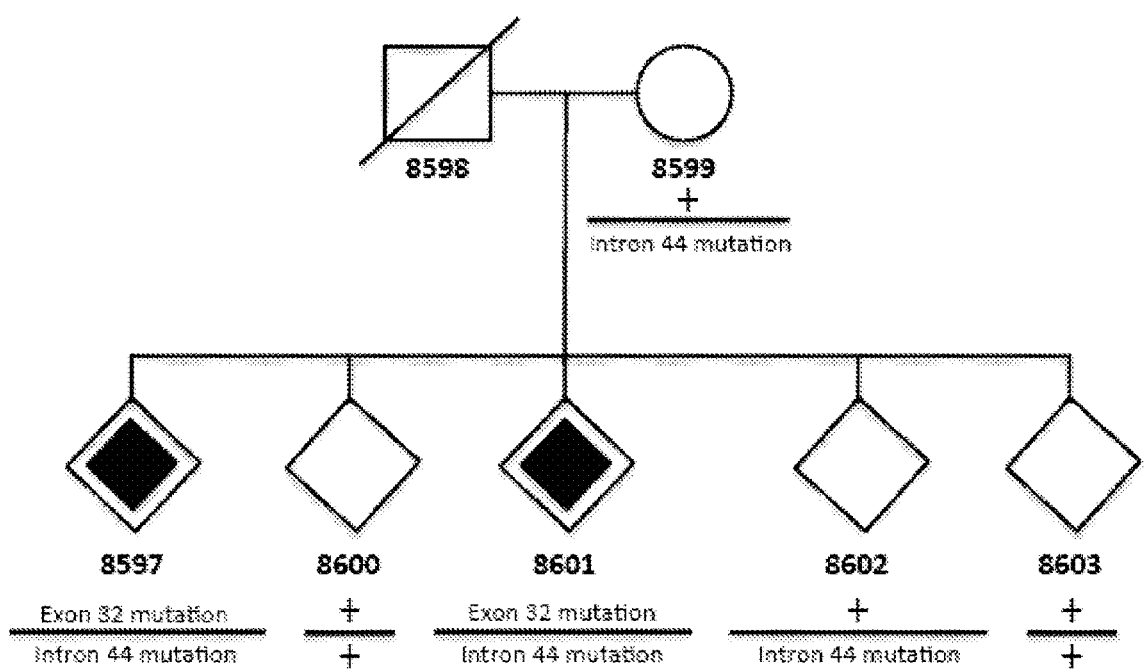

Genomic DNA was amplified and sequenced from blood samples taken from immediate relatives of P1 and P2 to determine the inheritance of all sequence variants in DYSF 44i, as well as the DYSF exon 32 mutation previously identified in these patients. FIG. 6 shows the DYSF genotypes of the family, revealing the maternal inheritance of the DYSF 44i mutation (c.4886+1249 (G>T)) responsible for PE44.1 expression. The segregation of all DYSF intron 44i allelic variants in family members is shown in Table 7.

Prevalence of the Deep Intronic DYSF (c.4886+1249 (G>T)) Mutation.

An allelic discrimination assay was used to screen genomic DNA from 112 patients (81 pedigrees) clinically diagnosed with either MM or LGMD2B, along with 724 individuals from a random population (either normal or with an unrelated disease), using the patient P1, P2 and their 4 family members as a reference. For this, TaqMan primers and probes were designed that distinguish the (c.4886+1249 (G>T)) point mutation from the normal genomic sequence in DYSF 44i. The 2 patients and 2 family members carry this mutation.

In the second phase of the study, separate analysis of eight suspected dysferlinopathy patients that had only one or neither of their pathogenic DYSF mutations identified by exon sequencing. These patients were screened for the C.4886+1249 (G>T) mutation. As shown in Table 9, DYSF protein was low or absent in these patients, with serum CK, an indicator of muscle damage, elevated in most. Of the eight patients screened, two carried the c.4886+1249 (G>T) variant allele.

Antisense Oligonucleotide-Mediated Pseudoexon PE44.1 Skipping.

The inclusion of PE44.1 leads to a disruptive insertion within the dysferlin protein; therefore preventing the spicing of this pseudoexon into the mature mRNA will promote the synthesis of normal mRNA. AONs directed against three possible exonic splice enhancer sequences within PE44.1 were designed (Table 4, FIG. 7A) to block these enhancer sequences and reduce the amount of PE44.1 included in mature transcripts. These AONS were transfected into patient and normal control iFDM cells and mRNAs were analyzed two to eight days later. As shown in FIG. 7B, AON1 treatment for 2 days did not detectably affect the levels of the mutant or normal transcripts and was similar to controls treated with TE or a non-targeting scrambled AON. However, AON2 and AON3, reduced the relative levels of the mutant splice form containing PE44.1, and led to an increase in the levels of the normal mRNA splice form in cells from both patients P1 and P2 (FIGS. 7B-D). For example, as shown in FIGS. 7C and D, the PE44.1 mutant form of RNA represented approximately 32-34% of the DYSF mRNA in P1 control cultures (TE or SCR scrambled control oligo), and approximately 41% in P2. AON2 treatment for 2 days reduced this mutant form to ~12% and 7% of the total DYSF levels in P1 and P2, respectively, while AON3 reduced it to ~15% and 6% (P1, P2 respectively). Concomitantly, there was an increase in the normal transcript levels in these cells: AON2 increased the normal form from ~45% of DYSF mRNA to ~70% in P1 cell, and from 38-44% to 78% in P2 cells. AON3 increased the normal form from ~45% of DYSF mRNA to ~66% in P1 cell, and from 38-44% to 92% in P2 cells. As expected, no PE44.1 containing mRNA was expressed in normal control cells. These results demonstrate that AONs can significantly modify mRNA splicing to inhibit mutant PE44.1 inclusion, which could potentially restore normal DYSF protein levels and function in these cells.

Figure 8:
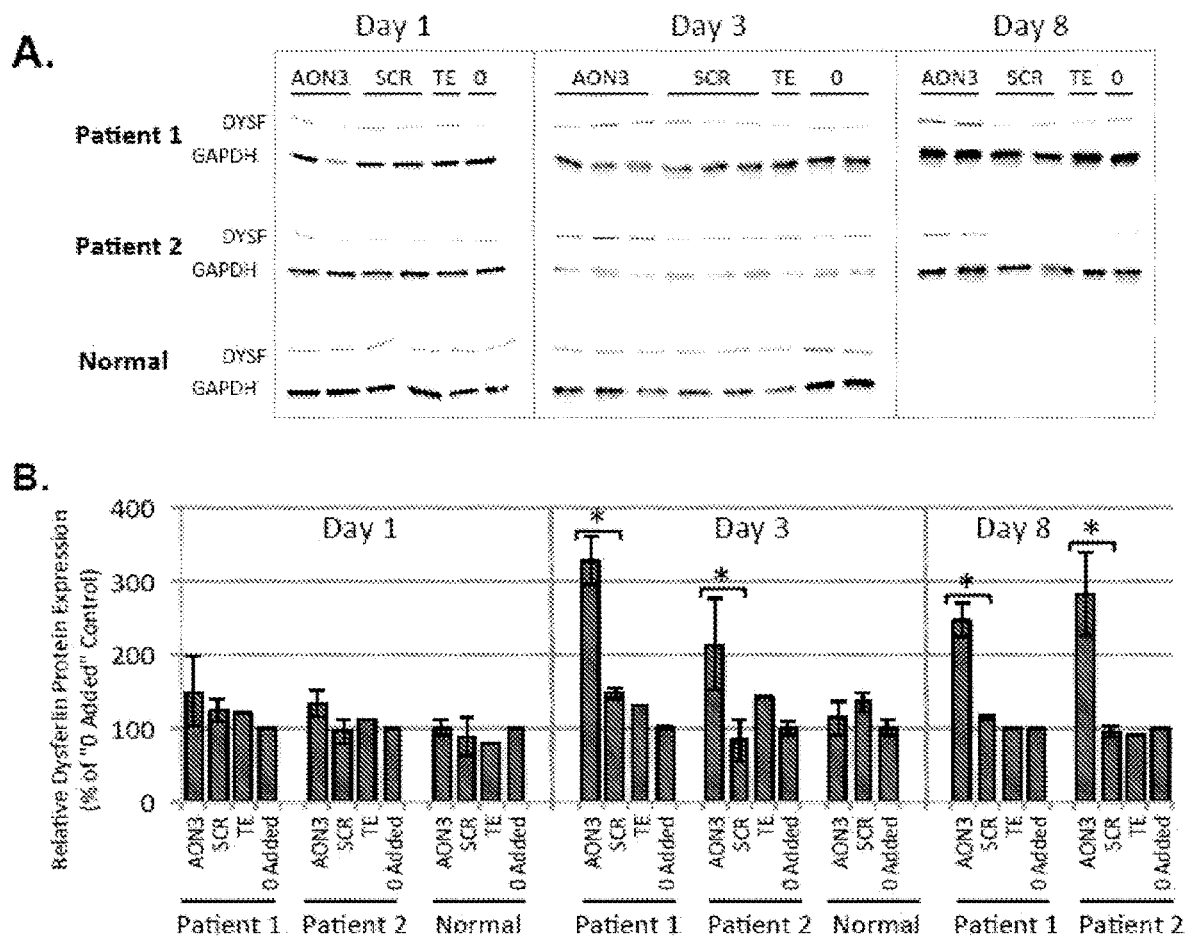
FIG. 8. Treatment of patient iFDMs with AONS directed to PE44.1 induces dysferlin protein expression. TMX-induced iFDMs (duplicate or triplicate cultures as shown) were cultured in DM for 6 days then treated with AONs in DM (or TE buffer or medium only (0) as controls). Cells were collected for protein analysis 1, 3 and 8 days after AON addition. For the 8-day samples, medium with AONS was removed on day 3 and replaced with DM only. (A) Western blots show that after 1 day of AON treatment there are no changes in DYSF protein expression, but DYSF levels were increased in AON3-treated cultures 3 and 8 days after AON addition. GAPDH expression served as a control for protein loading (5 μg protein/lane). (B) Quantitation of the bands shown in panel A reveals that there is a significant increase in DYSF protein in AON3-treated cultures compared with SCR oligo-treated controls (mean±SD, *$p<0.05$). Protein levels in normal control iFDM cultures are not affected by AON treatments.

Treatment of patient iFDMs with AON3 induced the synthesis of DYSF protein as well as higher levels of normal DYSF transcripts that don't contain PE44.1 (FIGS. 8 and 9).

Here, TMX-induced iFDM cells were treated with AONs after 6 days of differentiation, at a point when cells are undergoing fusion to form myotubes in these cultures. Eight days after adding AON3, there was a significant increase in DYSF protein detectable by Western blotting (FIGS. 8A-8B). After one day of AON3 treatment, there was a dramatic effect at the RNA level, with reduced expression of the mutant PE44.1 form and increase in the normal splice form (FIG. 9A, B). However, there was no significant change in the abundance of DYSF protein at this time (FIG. 8A, B). After three days of AON3 treatment, DYSF protein levels were significantly higher in cells from both patients, while normal control cells showed no differences due to AON3. These elevated DYSF protein levels persisted through 8 days post-AON3 addition (5 days after the AONs were removed on day 3). The effects of AON3 on the relative abundance of the PE44.1 and normal splice forms were also observed through 8 days post-AON3 addition (FIG. 9A, B). Therefore, AON-mediated skipping of PE44.1 can restore more normal levels of both DYSF mRNA and protein in these mutant cells.

Example 3: Production of an Anti-PE44.1 Antibody

Figure 10:
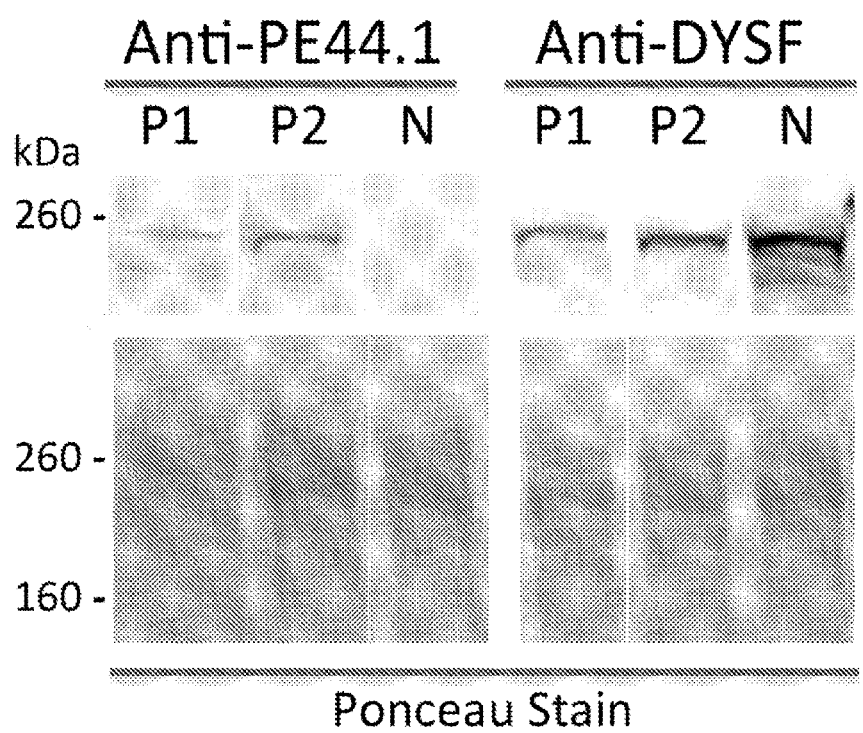
FIG. 10. Anti-PE44.1 antibody recognizes a protein (~237 kDa) in patient P1 and P2 iFDMs but not in normal (N) iFDMs. Protein blots (125 μg/lane) were probed with an antibody against PE44.1 or normal DYSF (Hamlet). P1 and P2 show reduced levels of normal DYSF compared with normal cells. Lower panels, Ponceau S stain of total proteins bound to the blot shows even protein loading.

Antibodies directed against the mutant peptide encoded by PE44.1 have been produced. An immunizing peptide having the amino acid sequence CAFEGEPALAS-DELPPSRDWR (SEQ ID NO: 122), corresponding to the C-terminal end of the 59 amino acid peptide encoded by PE44.1 (FIG. 3) was synthesized. Antibodies were produced in two rabbits, both of which had strong titers against the immunizing peptide. Western blot analysis of cultured myogenic iFDM cells from dysferlinopathy patients P1 and P2 (that carry the c.4886_1249 (G>T) dysferlin mutation) shows that the anti-PE44.1 antibodies detect a band near the size of dysferlin in patient but not in normal control cells (FIG. 10). Thus, the mutant form of dysferlin containing the extra PE44.1 encoded peptide is expressed in patient cells and can be identified using specific antibodies.

Example 4: Method of Detecting DYSF Mutation in Patient Samples

RNA from whole blood of patients (with pathologies unrelated to dysferlinopathy) were purified using the Qiagen PAXgene Blood RNA tubes and PAXgene Blood RNA Kit. Mutations in introns 44i were identified using the primers described above. RT-PCR was used to amplify DYSF cDNA from the blood RNA samples. Amplicons for each of the DYSF primer pairs were produced from the blood RNA, with products that included alternative DYSF mRNA isoforms known to be expressed normally in blood. These alternate isoforms arise from variant splicing of DYSF exons or different promoter usage. These results demonstrate screening of patient blood cells to identify intronic DYSF mutations that are not readily identifiable using standard methods of exon sequencing of genomic DNA. Additionally or alternatively, biological samples (e.g., blood) obtained from patients can be screened by Western blot using an anti-PE44.1 antibody, as shown in Example 3 (FIG. 10).

TABLE 1

Primers (forward (F) and reverse (R)) used to generate overlapping amplicons that span the entire dysferlin cDNA.

| Primer Name | Sequence | SEQ ID NO: |
|---|---|---|
| 1F | AGGTGCAAAATGCCGTGT | 1 |
| 1R | TTCACCCCTGCAAACACC | 2 |
| 2F | CACACCCGACACCGACAT | 3 |
| 2R | CTCCGCCTCATCTCCAGTG | 4 |
| 3F | CGACTCTGCCTGACCTGGA | 5 |
| 3R | AATGGTGCCCACGTCCAT | 6 |
| 4F | TCGTTCTCTCAGGACAGATGC | 7 |
| 4R | CTGAGGGTTGGCCGTCTT | 8 |
| 5F | GACCCCTTTGTGGAGGTCA | 9 |
| 5R | GCTCCACCAGCTTGGTCTC | 10 |
| 6F | GGGGGAAGGTGTGGCTTAT | 11 |
| 6R | CAGCGAGTCCACGTCCTC | 12 |
| 7F | CCAGCTGCTTGGGATTGC | 13 |
| 7R | TCCCACAATTCTTGCCACA | 14 |
| 8F | GCCCACCAAGTCCTCTTCTC | 15 |
| 8R | AAGCCGGGTCTGGTTCTC | 16 |
| 9F | TCACCTGAGCTTCGTGGAA | 17 |
| 9R | TTCTCCAGTGGCTCCATG C | 18 |
| 10F | CCACCTCGAGTACCGCAAG | 19 |
| 10R | CGTACAGCTCCACCACAATG | 20 |
| 11F | AACACCCTTAACCCCACCTG | 21 |
| 11R | CGGAGGTTCCTGATGACACA | 22 |
| 12F | CCCCAGCCTCGTGGTAGA | 23 |
| 12R | ACCTTCAGGGTGTCAAAATCC | 24 |
| 13F | TGCCTCCATAGGGGAGAGG | 25 |
| 13R | TGCAGGTCAGCTCGAACA | 26 |
| 14F | TGGAGCCCGTATTTGGAA | 27 |
| 14R | TGCAGGGGGCTGTAGAGG | 28 |

TABLE 1-continued

Primers (forward (F) and reverse (R)) used to generate overlapping amplicons that span the entire dysferlin cDNA.

| Primer Name | Sequence | SEQ ID NO: |
|---|---|---|
| 15F | CGTCTGGCTCTGCATGTG | 29 |
| 15R | CCACTCGTGCTGGGATTTT | 30 |
| 16F | CTGCCAGCTGAGCAAGTCTG | 31 |
| 16R | GCCGCCACAGGATGAACT | 32 |
| 17F | CCGACACCTCCTTCCTGTG | 33 |
| 17R | TTGTGGTTCCAACTGTTTTATACTGA | 34 |

TABLE 2

Primers (forward (F) and reverse (R)) used to generate overlapping amplicons that span dysferlin intron 44.

| Primer Name | Sequence | SEQ ID NO: |
|---|---|---|
| DYSFi44.1F | CCTGGGTGACAGAGCAAAAC | 35 |
| DYSFi44.1R | GCCTAAACAAGCTCACATCCA | 36 |
| DYSFi44.2F | TGAAATCTGAGAACAAGGAAAGGA | 37 |
| DYSFi44.2R | AATGGAAGGGTTTCTGTTGTGA | 38 |
| DYSFi44.3F | CCTCCCATGCCTGTTTCC | 39 |
| DYSFi44.3R | TATACACACACAACTGCATCCAAAGA | 40 |
| DYSFi44.4F | ACCCAGTCTCAGGCCATAACC | 41 |

TABLE 2-continued

Primers (forward (F) and reverse (R)) used to generate overlapping amplicons that span dysferlin intron 44.

| Primer Name | Sequence | SEQ ID NO: |
|---|---|---|
| DYSFi44.4R | AGGGCCCTTCCTTCCCTA | 42 |
| DYSFi44.5F | ATGTCTGTGTCCATG TGT CTGC | 43 |
| DYSFi44.5R | ATCTGAGAACTCCATCTACCATGT G | 44 |
| DYSFi44.6F | TCACCTGCAGGGAGCTCA T | 45 |
| DYSFi44.6R | GGAAGGGGACAGGACTTT | 46 |
| DYSFi44F | TTGGAGTCCCCCAATTTACC | 47 |
| DYSFi44R | GCAAATGCATCTTCTGAGCTT | 48 |

TABLE 3

TaqMan probes and primers used in allelic discrimination assays to screen genomic DNA for the dysferlin intron 44 mutation (c.4886 + 1249 (G > T)).

| Primer Name | Sequence (5' > 3') | SEQ ID NO: |
|---|---|---|
| DYSFi44.1F | GATGAGCTCCCACCAAGCA | 49 |
| DYSFi44.1R | AGCCCCTGGAACTCATACAGA | 50 |
| Probe Reporter Probe 1 (normal) | CACCTACCACTTCCCTCCA (VIC labeled) | 51 |
| Reporter Probe 2 (mutant) | ACCTACCACTTACCTCCA (FAM labeled) | 52 |

TABLE 4

AONs targeting human exonic splicing enhancer sequences (ESE) in DYSF PE44.1. AONs are 2'-O-methyl RNA with full-length phosphorothioate backbones.

| AON | AON Sequence (5' - 3') | Target Sequence (sense strand) (5' - 3') |
|---|---|---|
| DYSF44.1 AON1 | GAACAGUAGGUGUCUUCUGCAG (SEQ ID NO: 53) | CTGCAGAAGACACCTACTGTTC (SEQ ID NO: 54) |
| DYSF44.1 AON2 | CCAGGGCUGGUUCACCUUCAAA (SEQ ID NO: 55) | TTTGAAGGTGAACCAGCCCTGG (SEQ ID NO: 56) |
| DYSF44.1 AON3 | CUCCAAUCCCUGCUUGGUGG (SEQ ID NO: 57) | CCACCAAGCAGGGATTGGAG (SEQ ID NO: 58) |
| SCR (scrambled neg. control) | ACGGCGUGACUAGUGGUGAG (SEQ ID NO: 59) | |

TABLE 5

Primers (forward (F) and reverse (R)) used in RT-PCR assays to analyze RNA for expression for the dysferlin intron 44 mutant and normal transcripts.

| PCR Primer Name | Sequence (5' > 3') |
|---|---|
| DYSF 44/45-F | TAACTACATCCCCTGCACGC (SEQ ID NO: 60) |
| DYSF 44/45-R | CGACCGTCTCACCGATCTTT (SEQ ID NO: 61) |
| Quantitative PCR Primer Name | Sequence (5' > 3') |
| DYSF 44.1-Q-F | AGTGAGGACCCAGTCTCCTT (SEQ ID NO: 62) |
| DYSF 44.1-Q-R | AGCTCGAACATCCTCCAATCC (SEQ ID NO: 63) |
| DYSF 44/45-Q-F.2 | GCCCGTATTTGGAAAGATGT (SEQ ID NO: 64) |
| DYSF 44/45-Q-R.2 | CCGTCTCACCGATCTTTTCG (SEQ ID NO: 65) |
| DYSF 50/51-Q-F | CGTGCATTATCGTTCCCTGG (SEQ ID NO: 66) |
| DYSF 50/51-Q-R | AGGCATCCTTCTTGGCAATGG (SEQ ID NO: 67) |
| GAPDH-Q-F | ACCACAGTCCATGCCATCAC (SEQ ID NO: 68) |
| GAPDH-Q-R | ACCACAGTCCATGCCATCAC (SEQ ID NO: 69) |

TABLE 6 cDNA sequence variants in Miyoshi myopathy patients P1 and P2.

| SNP name | Ref. | Var. | Genotype 8597 (P1) | Genotype 8601 (P2) | Type | NT position | AA position | Exon | Sequence | Primers | Global MAF | Chromosomal location | SEQ ID NO |
|---|---|---|---|---|---|---|---|---|---|---|---|---|---|
| rs230359 6 | T | C | C\|C | C\|C | synonymous | c.1827 T > C | p.(D609=) | 20 | ATGTGGATGA[T/C]GCCATCCAGT | 6F + R | T = 0.4132/900 | 2: 71780215 | 70 |
| rs228835 5 | A | T | T\|T | T\|T | synonymous | c.2583 A > T | p.(S861=) | 25 | TTGGGCTCTC[A/T]GTGGATGAGA | 8F + R | A = 0.4463/972 | 2: 71795152 | 71 |
| rs230360 6 | C | A | A\|A | A\|A | synonymous | c.4008 C > A | p.(I1336=) | 38 | GTGCTTAGAT[C/A]CTGGCATGGG | 11F + R | A = 0.4784/1042 | 2: 71838597 | 72 |
| rs621459 39 | G | A | A\|A | A\|A | synonymous | c.4731 G > A | p.(E1577=) | 43 | GACCCCAGGA[G/A]TGCTTGGTCC | 13F + R | A = 0.0101/21 | 2: 71886100 | 73 |
| — | TG | AA | TG\|AA | TG\|AA | Indel | c.3444_3445 delTGinsAA | p.(Y1148X) | 32 | TTGGTGAAGA[T/A][G/A]GGAACCGCTA | 10F + R |  | 2:71817342-3 | 74 |

With reference to Table 6, reference (Ref.) and variant (Var.) alleles found in patients P1 and P2 and reported in the dbSNP database are shown. None of these SNP variants cause amino acid changes. The indel in exon 32 (c.3444_3445delTGinsAA) is a pathogenic mutation. The global minor allele frequency (MAF) and chromosomal location (GRCh37/hg19 assembly) are indicated, along with primer sets used to amplify and sequence these regions.

TABLE 7

Genomic DNA sequence variants in DYSF intron 44 of Miyoshi myopathy patients P1 and P2 and relatives.

| SNP name | Ref. | Var. | 8597 (P1) | 8601 (P2) | 8599 | 8600 | 8602 | 8603 | nt position | Sequence | Primers | Global MAF | Chromosomal location | SEQ ID NO |
|---|---|---|---|---|---|---|---|---|---|---|---|---|---|---|
| novel | G | T | G\|T | G\|T | G\|T | G\|T | G\|T | G\|G | c.4886 + 1249G > T | GGA TTG GAG G[G/T]A AGT GGT AGG T | i44.2F + RT | = 0/0* | 2: 718890 30 | 75 |
| rs3791825 | A | G | G\|G | G\|G | G\|G | G\|G | G\|G | G\|G | c.4886 + 1320A > G | CTG GCG CAG G[A/G]C CTC AGG CTA | i44.2F + RA | = 0.138 7/301 | 2: 718891 01 | 76 |
| rs3791826 | C | G | G\|G | G\|G | G\|G | G\|G | G\|G | G\|G | c.4886 + 1375C > G | AGT GGG TGG G[C/G]G TGT GTC AGG | i44.2F + RC | = 0.172 2/374 | 2: 718891 56 | 77 |
| rs2303598 | C | T | T\|T | T\|T | C\|T | C\|T | T\|T | T\|T | c.4887 − 162C > T | TAC ACA CAC A[C/T]TC AGG CCC AG | i44F + 13RC | = 0.374 7/816 | 2: 718912 36 | 78 |
| rs2303599 | C | T | T\|T | T\|T | T\|T | T\|T | T\|T | C\|T | c.4887 − 73C > T | TTG GGT GCC C[C/T]GT GTT GGC TG | i44F + 13RC | = 0.254 4/554 | 2: 718913 61 | 79 |
| rs55698153 | A | G | G\|G | G\|G | A\|G | A\|G | G\|G | G\|G | c.4887 − 11991A > G | TAG GGA AGG A[A/G] GGC CCT GCC | i44.5F + RA | = 0.292 9/637 | 2: 718901 99 | 80 |
| rs3791827 | C | G | G\|G | G\|G | C\|G | C\|G | G\|G | G\|G | c.4887 − 1083C > G | CTC ATG TGC C[C/G]A CCA CCG CTG | i44.5F + RC | = 0.400 4/871 | 2: 718903 15 | 81 |

With reference to Table 7, genomic variations within DYSF intron 44 in patients P1, P2 and relatives are listed. The novel mutation c.4886+1249 (G>T) results in PE44.1 inclusion in mature mRNAs. *The global MAF for the novel variant is calculated based on our screen of 836 unrelated individuals, in which 0 additional individuals were found with this variant. Other variations are reported in the dbSNP database and have not been shown to be pathogenic. The primer sets used to amplify and sequence these regions are shown.

TABLE 8

Additional AONs for enhancing expression of dysferlin mRNA and protein.

| AON | AON Sequence (5' - 3') | SEQ ID NO: | Target Sequence (sense strand) (5' - 3') | SEQ ID NO: |
|---|---|---|---|---|
| DYSF44.1 AON4 | CACCUACCACUUACCUCCAAUC | 82 | GATTGGAGGTAAGTGGTAGGTG | 99 |
| DYSF44.1 AON5 | CCUCUGCAUCCUCCCCUCUCUG | 83 | CAGAGAGGGGAGGATGCAGAGG | 100 |
| DYSF44.1 AON6 | GCGAGAGAAAUAGCUGCCAC | 84 | GTGGCAGCTATTTCTCTCGC | 101 |
| DYSF44.1 AON7 | AUACAGAGUUCCUCUCUCCC | 85 | GGGAGAGAGGAACTCTGTAT | 102 |
| DYSF44.1 AON8 | CAGCAAUUCAGGAUGCCUAGGAA | 86 | TTCCTAGGCATCCTGAATTGCTG | 103 |
| DYSF44.1 AON9 | GCCUAAACAAGCUCACAUCCAAA | 87 | TTTGGATGTGAGCTTGTTTAGGC | 104 |
| DYSF44.1 AON10 | AUAGCUGCCACCCUCCCUCU | 88 | AGAGGGAGGGTGGCAGCTAT | 105 |
| DYSF44.1 AON11 | GUCUUCUGCAGGUGCGAGAGAAA | 89 | TTTCTCTCGCACCTGCAGAAGAC | 106 |
| DYSF44.1 AON12 | UAUGUGACUUGAUGACAUCGGA | 90 | TCCGATGTCATCAAGTCACATA | 107 |
| DYSF44.1 AON13 | CAGACCCCGGUUUAUAAGUGCAA | 91 | TTGCACTTATAAACCGGGGTCTG | 108 |
| DYSF44.1 AON14 | GUGAGUGACCACAACUAACUCAA | 92 | TTGAGTTAGTTGTGGTCACTCAC | 109 |
| DYSF44.1 AON15 | GGAGACUGGGUCCUCACUGCAGG | 93 | CCTGCAGTGAGGACCCAGTCTCC | 110 |
| DYSF44.1 AON16 | UUCAAAAGCUGCAUUUCCCCAA | 94 | TTGGGGAAATGCAGCTTTTGAA | 111 |
| DYSF44.1 AON17 | UGGGAGCUCAUCACUGGCCAGGG | 95 | CCCTGGCCAGTGATGAGCTCCCA | 112 |
| DYSF44.1 AON18 | AGCUCGCCAGCCCCUGGAACUCA | 96 | TGAGTTCCAGGGGCTGGCGAGCT | 113 |
| DYSF44.1 AON19 | GAGGUCCUGCGCCAGCCCCUGGA | 97 | TCCAGGGGCTGGCGCAGGACCTC | 114 |
| DYSF44.1 AON20 | CUGCCCCAUCAGCAUUAGCCUGA | 98 | TCAGGCTAATGCTGATGGGGCAG | 115 |

TABLE 9

Dysferlin allele variants and the relative dysferlin expression in eight patients

| Patient No. | Age of onset | CK levels | Allele 1 | Allele 2 | Dysferlin expression in monocyte assay[1] |
|---|---|---|---|---|---|
| JF01 | 28 | 3369 | c.1834C > T (p.Q612X) | c.4886 + 1249 G > T | Absent |
| JF14 | 3 | 300 | — | — | Absent |
| JF15 | 18 | 198 | c.3534C > T (p.I1178) | — | Absent |
| JF19 | 18 | 10000 | c.2997G > T (p.W999C) | — | Absent |
| JF32 | 17 | 2800 | — | — | 9% |
| JF35 | 20 | 1800 | c.857T > A (p.V286E) | c.4886 + 1249 G > T | Absent |
| JF67 | 32 | 28000 | c.5341G > A (p.G1781R) | — | Absent |
| JF85 | 17 | 5675 | c.2997G > T (p.W999C) | — | 10% |

[1] The relative expression of dysferlin in monocytes is presented as the proportion of the level in normal control samples.

ADDITIONAL SEQUENCES

>DYSF Pseudoexon 44.1: SEQ ID NO: 116
AAGACACCTACTGTTCCGATGTCATCAAGTCACATATTGCACTTATAAACCGGGGTC
TGTTGAGTTAGTTGTGGTCACTCACCCTGCAGTGAGGACCCAGTCTCCTTGGGGAAA
TGCAGCTTTTGAAGGTGAACCAGCCCTGGCCAGTGATGAGCTCCCACCAAGCAGGG
ATTGGAG > DYSF Intron 43i through intron 45i in the context of Homo sapiens chromosome 2, GRCh38 Primary Assembly, NCBI Reference Sequence: NC_000002.12: SEQ ID NO: 117
GTAACTTTCCTAGAGCCCTCACCTCCCCAGAGTAGCAGGCTCAGGTACAAGTGGC
CTATAGAACCTGGACACAAACTCTGCCTCAGGGAGTTCATAGTAGGTTGGGAAACA
GACAAACACACAAAACTGAGAGGTGCCTGGATGGAGTTGTGTTAAGGACCAAGTGC
TCTAGAAGGTCAGGGAAGGCCAGTGTCAGTACAGGACTTTGGGAAAATGGGGAAG
GCTTCCTGGAAGGAATAGGACTCTTAGGATAGATGAGATTTTGATAGGCTGGGAGG
GAGAAGAAAATAGTGTTTTAAGAGGGGCCAAAAGCATAGGCAAAGGTTTGAAAGA
AAATTGCTTAATGTGTGTCTAGAACAAGAATAAAGCAGAAAGATAAGTAAGGCTGA
GGGTATAGGTTGGGACTCTCAATGGTTAATGGGGAGGAGTGATGGGGAAAGGAG
CAGCGTTAGTGACTGCTATGCCTAGTCATGGCAGAGTCCCAGGTAAAAGGGAATGC
TGGTAACACTCACCCGGTCTTTATTTAAAATTTTGATATTTTGTTCATCATGGACTAT
TGACACTGATTTTAATTTTTAAAATATTTCATTAAAGTACTGTTTATCTTAATAACTA
TTTTGGCCCTTCCTTACATTTTGTGCCCAAGATAAGTGCGTGAGCTGTCTCCCTCTAG
TCATTGCCTGAGATGGAGAGGGGAGATTTGAAGGAGGAAAGGAGTCTGGAGTTATG
GGGAGGTGACAGAGGTGGGAGGCAGAGTAATGTTGGGAAGAGAAAGAAAGAGGA
AAGAAGAGAGGCAGGGGTGGGGCCTGATTTGCCTTTACAGGCATGAGGCTAGGGTC
CCCTCTTGTCTCCTGAGGCAGGTTTAGGCCCAGCATGTGTCCTTCAGGTGGTGGGCG
GAGGCCTGGTATCCCACCCTGTAGCCTCACCTTTCAAGGGACAGAATGGAGCAGTT
CTCAGCCTAGGCACCACTGACGGCCTCCAAGGTGTGGTCATGGCCAGTGGGTTGGT
TTATATGCTTGAAGCCTTCCTGATGCTAGACTAACCCTGGGCACTCTGCAGCCCCAG
CTGCTGGGTCGCTGGCTGAGGGGTGCTGCTGCTTCCAGGAAGCATGGAGGGAGACC
TCCCTGGGCTAGCCTAGGCTGACATAGGCTGACCACCCCTCTCTCATTCCATATGCT
TAAGCAGAGGTCACAGAGAGGACCCCAGCCTGGTCTCGTCATGTGTGTAATGCAGA
CTGTTGTGTTTCTGATAAGGGCCTGGCCTCTCCCAATGGAGCAGTAGATTGGGAGTG
TGAAGGACTCAGGTGCCCCATTCCCACGGCTGGAGCCAAGACCAGAAGCCCATGTC
AGGGTCCAAGTGGAGTGGTGTGGTGTGTGGGAGGGGGCCCTGTCTTGGCAGGACAC
AGCCCACATCTCAACTTCCTGATGGCTGCTCCCTCATCCCATCCAGAGGCAAGGCAC
TCATGAAGCCTCAAAGACAGGTTTGGAAAGTGTTTTCACAGAAGTGTTTTGTCTCCT
CCTCCAGTGTGATCCTTACATCAAGATCTCCATAGGGAAGAAATCAGTGAGTGACC
AGGATAACTACATCCCCTGCACGCTGGAGCCCGTATTTGGAAAGTAAATTGGGGCA
TCTTGGGTCTTGGGGTGGAGGAGCCAGACAGGATAACCCACAGTCTAGTGGGGGAG
ATGTGACTGGCACTGTGAAGTCCGTATCTCTTGGAGCAAAACTGTATTCCTTAAATC
TTGCATGTCTATGGGGCATAGCCTCAGTTAGCCCTTCTTTAGCTGCTAAAGACTTG
ATCCCAACAGAAGCTCCTAGTTAAATGCTAAACAATTACGTCTAAGATCAGAAATC
TACATGGCTTGAGCTCAGGAGTTTGAGACCAGTCTGGGCAACATAGCAAGACCCCA
TCTCTACAAAAAATAAAAAACTTAGCCAGGCATGGTAGTGCATGCCTGTGGTTCCA
GATACTTGGGAGGCTGAGGTGGGAGGATCCCTTGAGCCTAGGAGTTTGAGCTTACA
GTGATCTGTGATCAAACTACTGCACTCCAGCCTGGGTGACAGAGCAAAACCCTGTC
TCAAAAAAAAAAAAAAAAAAAAGAAAGAAAAAGTAGAAATCTGTGTGTAAGCTC
AGAAGATGCATTTGCTAATTCTTTTTTTTTTTAAGATAAACTTTTACTTTGGAATAA
TTTTAGATTTACTAAACAGTTACAGAGACAGTGCATAATTTCCACTTACTCAATTTC
CCCCACTGGTAACCCCTTACTCAATTTCCCCCACTGGTATCATCTTACCTAACCATG
GGACATTTGTCAAAATGAAGAAATCATCATTGGTGCATTACGTTTAACCAAACTAG -continued

ADDITIONAL SEQUENCES

```
ACTTTTTTTTAAAGGATTTCATGTTTTCCCACTAATGTCCTCTTACTAATGTCTCAGG
ATCCAATCTGTTATACGACATTGCATTTAGTAATTAATTCTCTGTAAGTGTCCCACAT
GTGTTTGTAGCAAGAGCTAGAGGAAGAATGTAGACCCAAGATAGTAAAATGATTCC
TGAAATCTGAGAACAAGGAAAGGAAGAATCAATGCCCATTGCATGGGAGTAATTCC
TAGGCATCCTGAATTGCTGTTTGGATGTGAGCTTGTTTAGGCCAGAGAGGGGAGGA
TGCAGAGGGAGGGTGGCAGCTATTTCTCTCGCACCTGCAGAAGACACCTACTGTTC
CGATGTCATCAAGTCACATATTGCACTTATAAACCGGGGTCTGTTGAGTTAGTTGTG
GTCACTCACCCTGCAGTGAGGACCCAGTCTCCTTGGGGAAATGCAGCTTTTGAAGGT
GAACCAGCCCTGGCCAGTGATGAGCTCCCACCAAGCAGGGATTGGAGGGAAGTGGT
AGGTGGGAGAGAGGAACTCTGTATGAGTTCCAGGGGCTGGCGAGCTCCAGGGGCTG
GCGCAGGACCTCAGGCTAATGCTGATGGGGCAGTGGGCAGGGCCTGTTCCACAGTG
GGTGGGCGTGTGTCAGGACTCAGGGGAGATAGGGGAGCCAGTGCAGGAACACACC
CCTCCCATGCCTGTTTCCCCATCTCCCCCCAATCCTGGGCAAGCTGGTCTGCCTGGT
GCTTTAAGCCTCCTTCAGATCACAACAGAAACCCTTCCATTCTATAACCCATGTGTC
AGACGAACACAACGCATGAGGTGGTTTTTGTCACCATGTATTCCATGGCGTTACCTT
CTCCTTTCCCCTGAGGAAACTGACAGGCAGGTGACTTTTCTGCTCACATTGAGCTCA
GCCACTTTAACTCACGAACCCAGTCTCAGGCCATAACCCACTGCCCATTTGTATGGA
ATCCCGAGCTCCCTGATGGCTCTAGGGGAGTGTGTCCCCTCTTTGGATGCAGTTGTG
TGTGTATATGTGTGTATGTATGTGTGTGTATGTGTGTATATGTGCACATATGTGCGT
GCGTGTGTATGTATTTGTGTGTATGTGTGTGTATATGTGTATGTGTGTCTGTGTTCGT
GTGTCTGTGTGGTGTGTGTATATATGTGTGCATGTGTATTTGTGTGTATACATGTGTG
TAGGTGTATGCGTCTGTGTGTGTCTGTGTGTCTGTGTGGCATGTGTGTATTTTGTGTG
TATGTGTCTCTGTGTCCATGTGTCCGTGTATGTGTGTGGTGTGTGTATATGTATGTGT
GTTGTATGTATGTGTGTATGTGTATTTGTATATGTGCGTGTATGTGCATGTGTA
TTTGTATGTGTGTGTATGTGTGTTTGTGTCTGTGTGTCTGTGTGTGGTGTGTGTAT
ATGTGCATTTGTGTATATGTGTGTATGTGTGTGTGTCTGTGTCCATGTATGTGTGT
GTGTGTACGTGAGTACATTTGTGTGCCTGTGTGTGTATATGTGTGCACGTATGTGCA
TGTGTGTGTGTGTGCATATTTGTGTGTGTATGTCTGTGTCCATGTGTCTGCATATGTG
TGTGGTGTGTGTATATTTGTGTATGTTTACGTGTGTGTGTGTGTGCGCGCACGCG
CGTGGTGTAGGGAAGGAAGGGCCCTGCCTTCCTCCCTTCCTGGTCCAGTGTTTCTCC
CTTCCTGCTCTGGCTGACCTCTGAGGTTCTGACTCCTGCAGTGTCTGGGCTGGGGAG
AGGGCCCGTCTCATGTGCCCACCACCGCTGTCATCCGGGTACTCTCTGGACCACGGA
TGTTGAAAGCCGACTTATTTTCCTGTGGGTGCTTTCCAGAGGTTCCTCAGAGAGCCC
CCCGTGAGCCCTCCCACTGCACTTTCTGGGATATGGCAGATGCTGCGTCCCTTTAGC
TGCTGTCCCCAGCCCCTGGTTCTCAGATGGTCAACTCCACAATCTCTCGCTGCTACA
ACCCTCTGGGGGTCTCACAGGGCAGGATTCAGAGCAGTTCCAGTCTGGCCTCAGAG
TGGTTTCTTCTCCTCCCAGGAAGTCCTTGTGTTCCTTGCCCAGGCATGGGCCAGAGT
GCAGCTCCTCCCAAATGTGGCCCCTGCCCTCCTTCTCCATGCCACAAGTTGCTTAAG
TTTCCCTGAGCATGCACCAGGTGCCAGGCTTGTGTCTCTCACCTGCAGGGAGCTCAT
TTTAGGGGGAGAAGGGAGAATACCTCTCCCTTTGATGCACATGGTAGATGGAGTTC
TCAGATACAGCAAGAGCTCTCGCCAGAGAAATCTTTTCACAAATTCTCCCTCCATCC
CATCCCAGAAGTGGATGTGAAGAGTCCAGAAAGCAGGTCCCAGGCCTGGAGTTTCC
AGTCATCGGTAAATTCCAAAGCTCTGGCCCCTTGCTCTGGAGTACCAGTCGTCGGTA
AATTGGAGTCCCCCAATTTACCGGGAGTCCTCCCTGGACTGGAGGTACCAGTCGTCG
GTAAATTCCAAAGCTCTGGCCCCTGGCTCTGGAGTTTCACATCTCTTGCATCTGTTGT
CTCCTGGTGTCGTGGTCAAAGCTTCAGTTTTAATGTGCATTTCCAATTCATTCTTTCG
GTCTGTGGTCCATCAGGCAGGCACTTGCCTTATGCCCAGCACAGTTTATTTGGGAAA
GTCCTGTCCCCCTTCCCCCTACACACACACTCAGGCCCAGTACAGCAGTGCTGTGGG
TGGTTGGGCCTGTAAGATCTGTAGGGGGCCCAAGGAAAGAAGACTCCCTGGGGTAG
TTTCGAGCTCTTGTCCTGCCCTGCCTGTCCCTTGGGTGCCCCGTGTTGGCTGACATCG
GGAATCTGCCCCTCCTGCAGGATGTTCGAGCTGACCTGCACTCTGCCTCTGGAGAAG
GACCTAAAGATCACTCTCTATGACTATGACCTCCTCTCCAAGGACGAAAAGATCGG
TGAGACGGTCGTCGACCTGGAGAACAGGCTGCTGTCCAAGTTTGGGGCTCGCTGTG
GACTCCCACAGACCTACTGTGTGTACGTGGATGGGGGCTGGCTGCCTGCTTCTCTGA
CAACACACCACCCCTGTCTTCTCTGACAACACACCACCACTGAGCACTTACTGTGTG
CCAGCCCTGGGCTTAGCACTTCCTAGGCATTCTCTCATTGAGTCCAATGGGAGTCCT
ATCCCCACTCCACAGATGAAGAAACTGAAGCCCAGAGATGTTATTGCTTGTAAGTG
GTGGAATTAGGATTTGAACCAAGAACCTGGCTCATCACATTGTTATAATCCAGTTAT
CTGTAATGCACATAGAAGGCCTAGAGAGGGCTAGGTACCTGGAAAGGGAGAGAGG
GAAGGAAGGCAGGAAAGAAGCAGGGGAAACAGATGAGAGGACATGTGTGCTGCA
ACTGGGCCCGAAGGGGAATTTTGTGATGGTTTATGTCAGGGGAATGCATGTGAGGA
CTGCACCCCTCTTCCCACCATCTCAAGTCTTCTCTGGGTCTGATTATCTAACTCTGGA
AATTGAAAACATTTAAGTTGCAATTCCGTACTTAAATGAGTCCTTTTCTCTCTGAGC
CTCCATTTCTCCATCTGTAAAATGGGGATGCCCAGTCATGGTGAGCAATCAGATGGG
ACACCCACTGTAAAAGCAAGGAGTGGGCAATGCTGTACATGGGGGTACACCAGTCC
CTGCATGCCCCTCTACCCTCATGAGTGTCCTTGAAGCATCTCATCTATGTCTTGTGCT
TGCTCCTCAG
```

>DYSF Intron 43i through intron 45i in the context of Homo sapiens chromosome 2, alternate assembly CHM1_1.1, whole genome shotgun sequence, NCBI Reference Sequence: NC_018913.2:
SEQ ID NO: 118
```
GTAACTTTCCTAGAGCCCTCACCTCCCCCAGAGTAGCAGGCTCAGGTACAAGTGGC
CTATAGAACCTGGACACAAACTCTGCCTCAGGGAGTTCATAGTAGGTTGGGAAACA
GACAAACACACAAAACTGAGAGGTGCCTGGATGGAGTTGTGTTAAGGACCAAGTGC
TCTAGAAGGTCAGGGAAGGCCAGTGTCAGTACAGGACTTTGGGAAAATGGGAAG
GCTTCCTGGAAGGAATAGGACTCTTAGGATAGATGAGATTTTGATAGGCTGGGAGG
```

-continued

| ADDITIONAL SEQUENCES |
|---|
| GAGAAGAAAATAGTGTTTTAAGAGGGGCCAAAAGCATAGGCAAAGGTTTGAAAGA
AAATTGCTTAATGTGTGTCTAGAACAAGAATAAAGCAGAAAGATAAGTAAGGCTGA
GGGTATAGGTTGGGACTCTCAATGGTGAATGGGGAGGAGTGATGGGGGAAAGGAG
CAGCGTTAGTGACTGCTATGCCTAGTCATGGCAGAGTCCCAGGTAAAAGGGAATGC
TGGTAACACTCACCCGGTCTTTATTTAAAATTTTGATATTTTGTTCATCATGGACTAT
TGACACTGATTTTAATTTTTAAAATATTTCATTAAAGTACTGTTTATCTTAATAACTA
TTTTGGCCCTTCCTTACATTTTGTGCCCAAGATAAGTGCGTGAGCTGTCTCCCTCTAG
TCATTGCCTGAGATGGAGAGGGGAGATTTGAAGGAGGAAAGGAGTCTGGAGTTATG
GGGAGGTGACAGAGGTGGGAGGCAGAGTAATGTTGGGAAGAGAAAGAAAGAGGA
AAGAAGAGAGGCAGGGGTGGGGCCTGATTTGCCTTTACAGGCATGAGGCTAGGGTC
CCCTCTTGTCTCCTGAGGCAGGTTTAGGCCCAGCATGTGTCCTTCAGGTGGTGGGTG
GAGGCCTGGTATCCCACCCTGTAGCCTCACCTTTCAAGGGACAGAATGGAGCAGTT
CTCAGCCTAGGCACCACTGACGGCCTCCAAGGTGTGGTCATGGCCAGTGGGTTGGT
TTATATGCTTGAAGCCTTCCTGATGCTAGACTAACCCTGGGCACTCTGCAGCCCAG
CTGCTGGGTCGCTGGCTGAGGGGTGCTGCTGCTTCCAGGAAGCATGGAGGGAGACC
TCCCTGGGCTAGCCTAGGCTGACATAGGCTGACCACCCCTCTCTCATTCCATATGCT
TAAGCAGAGGTCACAGAGAGGACCCCAGCCTGGTCTCGTCATGTGTGTAATGCAGA
CTGTTGTGTTTCTGATAAGGGCCTGGCCTCTCCCAATGGAGCAGTAGATTGGGAGTG
TGAAGGACTCAGGTGCCCCATTCCCACGGCTGGAGCCAAGACCAGAAGCCCATGTC
AGGGTCCAAGTGGAGTGGTGTGGTGTGTGGGAGGGGGCCCTGTCTTGGCAGGACAC
AGCCCACATCTCAACTTCCTGATGGCTGCTCCCTCATCCCATCCAGAGGCAAGGCAC
TCATGAAGCCTCAAAGACAGGTTTGGAAAGTGTTTTCACAGAAGTGTTTTGTCTCCT
CCTCCAGTGTGATCCTTACATCAAGATCTCCATAGGGAAGAAATCAGTGAGTGACC
AGGATAACTACATCCCCTGCACGCTGGAGCCCGTATTTGGAAAGTAAATTGGGGCA
TCTTGGGTCTTGGGGTGGAGGAGCCAGACAGGATAACCCACAGTCTAGTGGGGGAG
ATGTGACTGGCACTGTGAAGTCCGTATCTCTTGGAGCAAAACTGTATTCCTTAAATC
TTGCATGTCTATGGGGCATAGCCTCAGTTAGCCCTTCTTTAGCTGCTAAAGACTTG
ATCCCAACAGAAGCTCCTAGTTAAATGCTAAACAATTACGTCTAAGATCAGAAATC
TACATGGCTTGAGCTCAGGAGTTTGAGACCAGTCTGGGCAACATAGCAAGACCCCA
TCTCTACAAAAAATAAAAAACTTAGCCAGGCATGGTAGTGCATGCCTGTGGTTCCA
GATACTTGGGAGGCTGAGGTGGGAGGATCCCTTGAGCCTAGGAGTTTGAGCTTACA
GTGATCTGTGATCAAACTACTGCACTCCAGCCTGGGTGACAGAGCAAAACCCTGTC
TCAAAAAAAAAAAAAAAAAAAAAAGAAAGAAAAAGTAGAAATCTGTGTGTAAGCTC
AGAAGATGCATTTGCTAATTCTTTTTTTTTTTAAGATAAACTTTTACTTTGGAATAA
TTTTAGATTTACTAAACAGTTACAGAGACAGTGCATAATTTCCACTTACTCAATTTC
CCCCACTGGTAACCCCTTACTCAATTTCCCCCACTGGTATCATCTTACCTAACCATG
GGACATTTGTCAAAATGAAGAAATCATCATTGGTGCATTACGTTTAACCAAACTAG
ACTTTTTTTTAAAGGATTTCATGTTTTCCCACTAATGTCCTCTTACTAATGTCTCAGG
ATCCAATCTGTTATACGACATTGCATTTAGTAATTAATTCTCTGTAAGTGTCCCACAT
GTGTTTGTAGCAAGAGCTAGAGGAAGAATGTAGACCCAAGATAGTAAAATGATTCC
TGAAATCTGAGAACAAGGAAAGGAAGAATCAATGCCCATTGCATGGGAGTAATTCC
TAGGCATCCTGAATTGCTGTTTGGATGTGAGCTTGTTTAGGCCAGAGAGGGGAGGA
TGCAGAGGGAGGGTGGCAGCTATTTCTCTCGCACCTGCAGAAGACACCTACTGTTC
CGATGTCATCAAGTCACATATTGCACTTATAAACCGGGGTCTGTTGAGTTAGTTGTG
GTCACTCACCCTGCAGTGAGGACCCAGTCTCCTTGGGGAAATGCAGCTTTTGAAGGT
GAACCAGCCCTGGCCAGTGATGAGCTCCCACCAAGCAGGGATTGGAGGGAAGTGGT
AGGTGGGAGAGAGGAACTCTGTATGAGTTCCAGGGGCTGGCGAGCTCCAGGGGCTG
GCGCAGGGCCTCAGGCTAATGCTGATGGGCAGTGGGCAGGGCCTGTTCCACAGTG
GGTGGGGGTGTGTCAGGACTCAGGGGAGATAGGGGAGCCAGTGCAGGAACACACC
CCTCCCCATGCCTGTTTCCCCATCTCCCCCAATCCTGGGCAAGCTGGTCTGCCTGGT
GCTTTAAGCCTCCTTCAGATCACAACAGAAACCCTTCCATTCTATAACCCATGTGTC
AGACGAACACAACGCATGAGGTGGTTTTTGTCACCATGTATTCCATGGCGTTACCTT
CTCCTTTCCCCTGAGGAAACTGACAGGCAGGTGACTTTTCTGCTCACATTGAGCTCA
GCCACTTTAACTCACGAACCCAGTCTCAGGCATAACCCACTGCCCATTTGTATGGA
ATCCCGAGCTCCCTGATGGCTCAGGGGAGTGTGTCCCCTCTTTGGATGCAGTTGTG
TGTGTATATGTGTGTATGTATGTGTGTATGTGTGTATATGTGCACATATGTGCGT
GCGTGTGTATGTATTTGTGTGTATGTGTGTATATGTGTATGTGTCTGTGTTCGT
GTGTCTGTGGTGTGTGTATATATGTGTGCATGTGTATTTGTGTGTATACATGTGTG
TAGGTGTATGCGTCTGTGTGTCTGTGTGTCTGTGTGGCATGTGTGTATTTTGTGTG
TGTGTATGTGTCTCTGTGTCCATGTGTCCGTGTATGTGTGGTGTGTATATGTAT
GTGTGTTGTATGTATGTGTGTATGTGTATTTGTATATGTGCGTGTATGTGCATG
TGTATTTGTATGTGTGTATGTGTGTTTGTGTCTGTGTCTGTGTGGTGTGT
GTATATGTGCATTTGTGTATATGTGTGTATGTGTGTGTCTGTGTCCATGTATGT
GTGTGTGTACGTGAGTACATTTGTGTGCCTGTGTGTATATGTGTGCACGTATG
TGCATGTGTGTGTGTGCATATTTGTGTGTATGTCTGTGTCCATGTGTCTGCATA
TGTGTGGTGTGTGTATATTTGTGTATGTTTACGTGTGTGTGTGTGTGCGCGCAC
GCGCGTGGTGTAGGGAAGGAGGGGCCCTGCCTTCCTCCCTTCCTGGTCCAGTGTTTC
TCCCTTCCTGCTCTGGCTGACCTCTGAGGTTCTGACTCCTGCAGTGTCTGGGCTGGG
GAGAGGGCCCGTCTCATGTGCCGACCACCGCTGTCATCCGGGTACTCTCTGGACCAC
GGATGTTGAAAGCCGACTTATTTTCCTGTGGGTGCTTTCCAGAGGTTCCTCAGAGAG
CCCCCCGTGAGCCCTCCCACTGCACTTTCTGGGATATGGCAGATGCTGCGTCCCTTT
AGCTGCTGTCCCCAGCCCCTGGTTCTCAGATGGTCAACTCCACAATCTCTCGCTGCT
ACAACCCTCTGGGGTCTCACAGGGCAGGATTCAGAGCAGTTCCAGTCTGGCCTCA
GAGTGGTTTCTTCTCCTCCCAGGAAGTCCTTGTGTTCCTTGCCCAGGCATGGGCCAG
AGTGCAGCTCCTCCCAAATGTGGCCCCTGCCCTCCTTCTCCATGCCACAAGTTGCTT
AAGTTTCCCTGAGCATGCACCAGGTGCCAGGCTTGTGTCTCTCACCTGCAGGGAGCT
CATTTTAGGGGGAGAAGGGAGAATACCTCTCCCTTTGATGCACATGGTAGATGGAG |

ADDITIONAL SEQUENCES

```
TTCTCAGATACAGCAAGAGCTCTCGCCAGAGAAATCTTTTCACAAATTCTCCCTCCA
TCCCATCCCAGAAGTGGATGTGAAGAGTCCAGAAAGCAGGTCCCAGGCCTGGAGTT
TCCAGTCATCGGTAAATTCCAAAGCTCTGGCCCCTTGCTCTGGAGTACCAGTCGTCG
GTAAATTGGAGTCCCCCAATTTACCGGGAGTCCTCCCTGGACTGGAGGTACCAGTC
GTCGGTAAATTCCAAAGCTCTGGCCCCTGGCTCTGGAGTTTCACATCTCTTGCATCT
GTTGTCTCCTGGTGTCGTGGTCAAAGCTTCAGTTTTAATGTGCATTTCCAATTCATTC
TTTCGGTCTGTGGTCCATCAGGCAGGCACTTGCCTTATGCCCAGCACAGTTTATTTG
GGAAAGTCCTGTCCCCCTTCCCCCTACACACACATTCAGGCCCAGTACAGCAGTGCT
GTGGGTGGTTGGGCCTGTAAGATCTGTAGGGGGCCCAAGGAAAGAAGACTCCCTGG
GGTAGTTTCGAGCTCTTGTCCTGCCCTGCCTGTCCCTTGGGTGCCCTGTGTTGGCTGA
CATCGGGAATCTGCCCCTCCTGCAGGATGTTCGAGCTGACCTGCACTCTGCCTCTGG
AGAAGGACCTAAAGATCACTCTCTATGACTATGACCTCCTCTCCAAGGACGAAAAG
ATCGGTGAGACGGTCGTCGACCTGGAGAACAGGCTGCTGTCCAAGTTTGGGGCTCG
CTGTGGACTCCCACAGACCTACTGTGTGTACGTGGATGGGGCTGGCTGCCTGCTTC
TCTGACAACACACCACCCCTGTCTTCTCTGACAACACACCACCACTGAGCACTTACT
GTGTGCCAGCCCTGGGCTTAGCACTTCCTAGGCATTCTCTCATTGAGTCCAATGGGA
GTCCTATCCCCACTCCACAGATGAAGAAACTGAAGCCCAGAGATGTTATTGCTTGTA
AGTGGTGGAATTAGGATTTGAACCAAGAACCTGGCTCATCACATTGTTATAATCCA
GTTATCTGTAATGCACATAGAAGGCCTAGAGAGGGCTAGGTACCTGGAAAGGGAGA
GAGGGAAGGAAGGCAGGAAAGAAGCAGGGGAAACAGATGAGGGACATGTGTGC
TGCAACTGGGCCCGAAGGGGAATTTTGTGATGGTTTATGTCAGGGGAATGCATGTG
AGGACTGCACCCCTCTTCCCACCATCTCAAGTCTTCTCTGGGTCTGATTATCTAACTC
TGGAAATTGAAAACATTTAAGTTGCAATTCCGTACTTAAATGAGTCCTTTTCTCTCT
GAGCCTCCATTTCTCCATCTGTAAAATGGGGATGCCCAGTCATGGTGAGCAATCAG
ATGGGACACCCACTGTAAAAGCAAGGAGTGGGCAATGCTGTACATGGGGGTACACC
AGTCCCTGCATGCCCCTCTACCCTCATGAGTGTCCTTGAAGCATCTCATCTATGTCTT
GTGCTTGCTCCTCAG
```

>DYSF Intron 43i through intron 45i in the context of *Homo sapiens* chromosome 2, alternate assembly HuRef whole genome shotgun sequence, NCBI Reference Sequence: AC_000134.1: SEQ ID NO: 119

```
GTAACTTTCCTAGAGCCCTCACCTCCCCCAGAGTAGCAGGCTCAGGTACAAGTGGC
CTATAGAACCTGGACACAAACTCTGCCTCAGGGAGTTCATAGTAGGTTGGGAAACA
GACAAACACACAAAACTGAGAGGTGCCTGGATGGAGTTGTGTTAAGGACCAAGTGC
TCTAGAAGGTCAGGGAAGGCCAGTGTCAGTACAGGACTTTGGGAAAATGGGGAAG
GCTTCCTGGAAGGAATAGGACTCTTAGGATAGATGAGATTTTGATAGGCTGGGAGG
GAGAAGAAAATAGTGTTTTAAGAGGGGCCAAAAGCATAGGCAAAGGTTTGAAAGA
AAATTGCTTAATGTGTGTCTAGAACAAGAATAAAGCAGAAAGATAAGTAAGGCTGA
GGGTATAGGTTGGGACTCTCAATGGTGAATGGGGAGGAGTGATGGGGGAAAGGAG
CAGCGTTAGTGACTGCTATGCCTAGTCATGGCAGAGTCCCAGGTAAAAGGGAATGC
TGGTAACACTCACCCGGTCTTTATTTAAAATTTTGATATTTTGTTCATCATGGACTAT
TGACACTGATTTTAATTTTTAAAATATTTCATTAAAGTACTGTTTATCTTAATAACTA
TTTTGGCCCTTCCTTACATTTTGTGCCCAAGATAAGTGCGTGAGCTGTCTCCCTCTAG
TCATTGCCTGAGATGGAGAGGGGAGATTTGAAGGAGGAAAGGAGTCTGGAGTTATG
GGGAGGTGACAGAGGTGGGAGGCAGAGTAATGTTGGGAAGAGAAAGAAAGAGGA
AAGAAGAGAGGCAGGGGTGGGGCCTGATTTGCCTTTACAGGCATGAGGCTAGGGTC
CCCTCTTGTCTCCTGAGGCAGGTTTAGGCCCAGCATGTGTCCTTCAGGTGGTGGGTG
GAGGCCTGGTATCCCACCCTGTAGCCTCACCTTTCAAGGGACAGAATGGAGCAGTT
CTCAGCCTAGGCACCACTGACGGCCTCCAAGGTGTGGTCATGGCCAGTGGGTTGGT
TTATATGCTTGAAGCCTTCCTGATGCTAGACTAACCCTGGGCACTCTGCAGCCCCAG
CTGCTGGGTCGCTGGCTGAGGGGTGCTGCTGCTTCCAGGAAGCATGGAGGGAGACC
TCCCTGGGCTAGCCTAGGCTGACATAGGCTGACCACCCCTCCTCTCATTCCATATGCT
TAAGCAGAGGTCACAGAGAGGACCCCAGCCTGGTCTCGTCATGTGTAATGCAGA
CTGTTGTGTTTCTGATAAGGGCCTGGCCTCTCCCAATGGAGCAGTAGATTGGGAGTG
TGAAGGACTCAGGTGCCCCATTCCCACGGCTGGAGCCAAGACCAGAAGCCCATGTC
AGGGTCCAAGTGGAGTGGTGTGGTGTGTGGGAGGGGGCCCTGTCTTGGCAGGACAC
AGCCCACATCTCAACTTCCTGATGGCTGCTCCCTCATCCCATCCAGAGGCAAGGCAC
TCATGAAGCCTCAAAGACAGGTTTGGAAAGTGTTTTCACAGAAGTGTTTTGTCTCCT
CCTCCAGTGTGATCCTTACATCAAGATCTCCATAGGGAAGAAATCAGTGAGTGACC
AGGATAACTACATCCCCTGCACGCTGGAGCCCGTATTTGGAAAGTAAATTGGGGCA
TCTTGGGTCTTGGGGTGGAGGAGCCAGACAGGATAACCCACAGTCTAGTGGGGGAG
ATGTGACTGGCACTGTGAAGTCCGTATCTCTTGGAGCAAAACTGTATTCCTTAAATC
TTGCATGTCTATGGGGCATAGCCTCAGTTAGCCCTTCTTTAGCTGCTAAAGACTTG
ATCCCAACAGAAGCTCCTAGTTAAATGCTAAACAATTACGTCTAAGATCAGAAATC
TACATGGCTTGAGCTCAGGAGTTTGAGACCAGTCTGGGCAACATAGCAAGACCCCA
TCTCTACAAAAAATAAAAAACTTAGCCAGGCATGGTAGTGCATGCCTGTGGTTCCA
GATACTTGGGAGGCTGAGGTGGGAGGATCCCTTGAGCCTAGGAGTTTGAGCTTACA
GTGATCTGTGATCAAACTACTGCACTCCAGCCTGGGTGACAGAGCAAAACCCTGTC
TCAAAAAAAAAAAAAAAAAAAAGAAAGAAAAAGTAGAAATCTGTGTGTAAGCTC
AGAAGATGCATTTGCTAATTCTTTTTTTTTTTTAAGATAAACTTTTACTTTGGAATAA
TTTTAGATTTACTAAACAGTTACAGAGACAGTGCATAATTTCCACTTACTCAATTTC
CCCCACTGGTAACCCCTTACTCAATTTCCCCCACTGGTATCATCTTACCTAACCATG
GGACATTTGTCAAAATGAAGAAATCATCATTGGTGCATTACGTTTAACCAAACTAG
ACTTTTTTTTAAAGGATTTCATGTTTTCCCACTAATGTCCTCTTACTAATGTCTCAGG
ATCCAATCTGTTATACGACATTGCATTTAGTAATTAATTCTCTGTAAGTGTCCCACAT
GTGTTTGTAGCAAGAGCTAGAGGAAGAATGTAGACCCAAGATAGTAAAATGATTCC
```

ADDITIONAL SEQUENCES

```
TGAAATCTGAGAACAAGGAAAGGAAGAATCAATGCCCATTGCATGGGAGTAATTCC
TAGGCATCCTGAATTGCTGTTTGGATGTGAGCTTGTTTAGGCCAGAGAGGGGAGGA
TGCAGAGGGAGGGTGGCAGCTATTTCTCTCGCACCTGCAGAAGACACCTACTGTTC
CGATGTCATCAAGTCACATATTGCACTTATAAACCGGGGTCTGTTGAGTTAGTTGTG
GTCACTCACCCTGCAGTGAGGACCCAGTCTCCTTGGGGAAATGCAGCTTTTGAAGGT
GAACCAGCCCTGGCCAGTGATGAGCTCCCACCAAGCAGGGATTGGAGGGAAGTGGT
AGGTGGGAGAGAGGAACTCTGTATGAGTTCCAGGGGCTGGCGAGCTCCAGGGGCTG
GCGCAGGGCCTCAGGCTAATGCTGATGGGGCAGTGGGCAGGGCCTGTTCCACAGTG
GGTGGGGGTGTGTCAGGACTCAGGGGAGATAGGGGAGCCAGTGCAGGAACACACC
CCTCCCATGCCTGTTTCCCCATCTCCCCCCAATCCTGGGCAAGCTGGTCTGCCTGGT
GCTTTAAGCCTCCTTCAGATCACAACAGAAACCCTTCCATTCTATAACCCATGTGTC
AGACGAACACAACGCATGAGGTGGTTTTTGTCACCATGTATTCCATGGCGTTACCTT
CTCCTTTCCCTGAGGAAACTGACAGGCAGGTGACTTTTCTGCTCACATTGAGCTCA
GCCACTTTAACTCACGAACCCAGTCTCAGGCCATAACCCACTGCCCATTTGTATGGA
ATCCCGAGCTCCCTGATGGCTCTAGGGGAGTGTGTCCCCTCTTTGGATGCAGTTGTG
TGTGTATATGTGTATGTATGTGTGTGTATGTGTGTATATGTGCACATATGTGCGT
GCGTGTGTATGTATTTGTGTGTGTGTGTATATGTGTATGTGTGTTCGTGTGTCT
GTGTGGTGTGTATATATGTGCATGTGTATTTGTGTGTATACATGTGTGTAGGT
GTATGCGTCTGTGTGTGTCTGTGTGTCTGTGTGGCATGTGTGTATTTTGTGTGTGT
ATGTGTCTCTGTGTCCATGTGTCCGTGTATGTGTGTGGTGTGTGTATATGTATGTG
TTGTATGTATGTGTGTGTATGTGTATTTGTATATGTGTGCGTGTATGTGCATGTGTAT
TTGTATGTGTGTGTATGTGTGTTTGTGTCTGTGTGTCTGTGTGTGGTGTGTATA
TGTGCATTTGTGTATATGTGTGTGTATGTGTGTGTCTGTGTCCATGTATGTGTGTG
TGTGTACGTGAGTACATTTGTGTGCCTGTGTGTATATGTGTGCACGTATGTGCAT
GTGTGTGTGTGTGCATATTTGTGTGTGTATGTCTGTGTCCATGTGTCTGCATATGTGT
GTGGTGTGTGTATATTTGTGTATGTTTACGTGTGTGTGTGTGTGCGCGCACGCGC
GTGGTGTAGGGAAGGAAGGGCCCTGCCTTCCTCCCTTCCTGGTCCAGTGTTTCTCCC
TTCCTGCTCTGGCTGACCTCTGAGGTTCTGACTCCTGCAGTGTCTGGGCTGGGGAGA
GGGCCCGTCTCATGTGCCCACCACCGCTGTCATCCGGGTACTCTCTGGACCACGGAT
GTTGAAAGCCGACTTATTTTCCTGTGGGTGCTTTCCAGAGGTTCCTCAGAGAGCCCC
CCGTGAGCCCTCCCACTGCACTTTCTGGGATATGGCAGATGCTGCGTCCCTTTAGCT
GCTGTCCCAGCCCTGGTTCTCAGATGGTCAACTCCACAATCTCTCGCTGCTACAA
CCCTCTGGGGGTCTCACAGGGCAGGATTCAGAGCAGTTCCAGTCTGGCCTCAGAGT
GGTTTCTTCTCCTCCCAGGAAGTCCTTGTGTTCCTTGCCCAGGCATGGGCCAGAGTG
CAGCTCCTCCCAAATGTGGCCCCTGCCCTCCTTCTCCATGCCACAAGTTGCTTAAGT
TTCCCTGAGCATGCACCAGGTGCCAGGCTTGTGTCTCTCACCTGCAGGGAGCTCATT
TTAGGGGGAGAAGGGAGAATACCTCTCCCTTTGATGCACATGGTAGATGGAGTTCT
CAGATACAGCAAGAGCTCTCGCCAGAGAAATCTTTTCACAAATTCTCCCTCCATCCC
ATCCCAGAAGTGGATGTGAAGAGTCCAGAAAGCAGGTCCCAGGCCTGGAGTTTCCA
GTCATCGGTAAATTCCAAAGCTCTGGCCCCTTGCTCTGGAGTACCAGTCGTCGGTAA
ATTGGAGTCCCCCAATTTACCGGGAGTCCTCCCTGGACTGGAGGTACCAGTCGTCGG
TAAATTCCAAAGCTCTGGCCCCTGGCTCTGGAGTTTCACATCTCTTGCATCTGTTGTC
TCCTGGTGTCGTGGTCAAAGCTTCAGTTTTAATGTGCATTTCCAATTCATTCTTTCGG
TCTGTGGTCCATCAGGCAGGCACTTGCCTTATGCCCAGCACAGTTTATTTGGGAAAG
TCCTGTCCCCCTTCCCCCTACACACACATTCAGGCCCAGTACAGCAGTGCTGTGGGT
GGTTGGGCCTGTAAGATCTGTAGGGGGCCCAAGGAAAGAAGACTCCCTGGGGTAGT
TTCGAGCTCTTGTCCTGCCCTGCCTGTCCCTTGGGTGCCCTGTGTTGGCTGACATCGG
GAATCTGCCCCTCCTGCAGGATGTTCGAGCTGACCTGCACTCTGCCTCTGGAGAAGG
ACCTAAAGATCACTCTCTATGACTATGACCTCCTCTCCAAGGACGAAAAGATCGGT
GAGACGGTCGTCGACCTGGAGAACAGGCTGCTGTCCAAGTTTGGGGCTCGCTGTGG
ACTCCCACAGACCTACTGTGTGTACGTGGATGGGGGCTGGCTGCCTGCTTCTCTGAC
AACACACCACCCCTGTCTTCTCTGACAACACACCACCACTGAGCACTTACTGTGTGC
CAGCCCTGGGCTTAGCACTTCCTAGGCATTCTCTCATTGAGTCCAATGGGAGTCCTA
TCCCCACTCCACAGATGAAGAAACTGAAGCCCAGAGATGTTATTGCTTGTAAGTGG
TGGAATTAGGATTTGAACCAAGAACCTGGCTCATCACATTGTTATAATCCAGTTATC
TGTAATGCACATAGAAGGCCTAGAGAGGGCTAGGTACCTGGAAAGGGAGAGAGGG
AAGGAAGGCAGGAAAGAAGCAGGGGAAACAGATGAGAGGACATGTGTGCTGCAAC
TGGGCCCGAAGGGGAATTTTGTGATGGTTTATGTCAGGGGAATGCATGTGAGGACT
GCACCCCTCTTCCCACCATCTCAAGTCTTCTCTGGGTCTGATTATCTAACTCTGGAAA
TTGAAAACATTTAAGTTGCAATTCCGTACTTAAATGAGTCCTTTTCTCTCTGAGCCTC
CATTTCTCCATCTGTAAAATGGGGATGCCCAGTCATGGTGAGCAATCAGATGGGAC
ACCCACTGTAAAAGCAAGGAGTGGGCAATGCTGTACATGGGGGTACACCAGTCCCT
GCATGCCCCTCTACCCTCATGAGTGTCCTTGAAGCATCTCATCTATGTCTTGTGCTTG
CTCCTCAG

> DYSF Intron 44 in the context of a c.4886 + 1249 (G > T)
mutation: SEQ ID NO: 120
GTAAATTGGGGCATCTTGGGTCTTGGGGTGGAGGAGCCAGACAGGATAACCCACAG
TCTAGTGGGGAGATGTGACTGGCACTGTGAAGTCCGTATCTCTTGGAGCAAAACT
GTATTCCTTAAATCTTGCATGTCTATGGGGGCATAGCCTCAGTTAGCCCTTCTTTAGC
TGCTAAAGACTTGATCCCAACAGAAGCTCCTAGTTAAATGCTAAACAATTACGTCTA
AGATCAGAAATCTACATGGCTTGAGCTCAGGAGTTTGAGACCAGTCTGGGCAACAT
AGCAAGACCCCATCTCTACAAAAAATAAAAAACTTAGCCAGGCATGGTAGTGCATG
CCTGTGGTTCCAGATACTTGGGAGGCTGAGGTGGGAGGATCCCTTGAGCCTAGGAG
TTTGAGCTTACAGTGATCTGTGATCAAACTACTGCACTCCAGCCTGGGTGACAGAGC
AAAACCCTGTCTCAAAAAAAAAAAAAAAAAAAAGAAAGAAAAGTAGAAATCTG
TGTGTAAGCTCAGAAGATGCATTTGCTAATTCTTTTTTTTTTTAAGATAAACTTTTA
```

| ADDITIONAL SEQUENCES |
|---|
| CTTTGGAATAATTTTAGATTTACTAAACAGTTACAGAGACAGTGCATAATTTCCACT<br>TACTCAATTTCCCCCACTGGTAACCCCTTACTCAATTTCCCCCACTGGTATCATCTTA<br>CCTAACCATGGGACATTTGTCAAAATGAAGAAATCATCATTGGTGCATTACGTTTAA<br>CCAAACTAGACTTTTTTTTAAAGGATTTCATGTTTTCCCACTAATGTCCTCTTACTAA<br>TGTCTCAGGATCCAATCTGTTATACGACATTGCATTTAGTAATTAATTCTCTGTAAGT<br>GTCCCACATGTGTTTGTAGCAAGAGCTAGAGGAAGAATGTAGACCCAAGATAGTAA<br>AATGATTCCTGAAATCTGAGAACAAGGAAAGGAAGAATCAATGCCCATTGCATGGG<br>AGTAATTCCTAGGCATCCTGAATTGCTGTTTGGATGTGAGCTTGTTTAGGCCAGAGA<br>GGGGAGGATGCAGAGGGAGGGTGGCAGCTATTTCTCTCGCACCTGCAG<br><br>>Intron 44: SEQ ID NO: 121<br>GTAAATTGGGGCATCTTGGGTCTTGGGGTGGAGGAGCCAGACAGGATAACCCACAG<br>TCTAGTGGGGGAGATGTGACTGGCACTGTGAAGTCCGTATCTCTTGGAGCAAAACT<br>GTATTCCTTAAATCTTGCATGTCTATGGGGGCATAGCCTCAGTTAGCCCTTCTTTAGC<br>TGCTAAAGACTTGATCCCAACAGAAGCTCCTAGTTAAATGCTAAACAATTACGTCTA<br>AGATCAGAAATCTACATGGCTTGAGCTCAGGAGTTTGAGACCAGTCTGGGCAACAT<br>AGCAAGACCCCATCTCTACAAAAAATAAAAAACTTAGCCAGGCATGGTAGTGCATG<br>CCTGTGGTTCCAGATACTTGGGAGGCTGAGGTGGGAGGATCCCTTGAGCCTAGGAG<br>TTTGAGCTTACAGTGATCTGTGATCAAACTACTGCACTCCAGCCTGGGTGACAGAGC<br>AAAACCCTGTCTCAAAAAAAAAAAAAAAAAAAAAGAAAGAAAAAGTAGAAATCTG<br>TGTGTAAGCTCAGAAGATGCATTTGCTAATTCTTTTTTTTTTTAAGATAAACTTTTA<br>CTTTGGAATAATTTTAGATTTACTAAACAGTTACAGAGACAGTGCATAATTTCCACT<br>TACTCAATTTCCCCCACTGGTAACCCCTTACTCAATTTCCCCCACTGGTATCATCTTA<br>CCTAACCATGGGACATTTGTCAAAATGAAGAAATCATCATTGGTGCATTACGTTTAA<br>CCAAACTAGACTTTTTTTTAAAGGATTTCATGTTTTCCCACTAATGTCCTCTTACTAA<br>TGTCTCAGGATCCAATCTGTTATACGACATTGCATTTAGTAATTAATTCTCTGTAAGT<br>GTCCCACATGTGTTTGTAGCAAGAGCTAGAGGAAGAATGTAGACCCAAGATAGTAA<br>AATGATTCCTGAAATCTGAGAACAAGGAAAGGAAGAATCAATGCCCATTGCATGGG<br>AGTAATTCCTAGGCATCCTGAATTGCTGTTTGGATGTGAGCTTGTTTAGGCCAGAGA<br>GGGGAGGATGCAGAGGGAGGGTGGCAGCTATTTCTCTCGCACCTGCAGAAGACACC<br>TACTGTTCCGATGTCATCAAGTCACATATTGCACTTATAAACCGGGGTCTGTTGAGT<br>TAGTTGTGGTCACTCACCCTGCAGTGAGGACCCAGTCTCCTTGGGGAAATGCAGCTT<br>TTGAAGGTGAACCAGCCCTGGCCAGTGATGAGCTCCCACCAAGCAGGGATTGGAGG<br>GAAGTGGTAGGTGGGAGAGAGGAACTCTGTATGAGTTCCAGGGGCTGGCGAGCTCC<br>AGGGGCTGGCGCAGGACCTCAGGCTAATGCTGATGGGGCAGTGGGCAGGGCCTGTT<br>CCACAGTGGGTGGGCGTGTGTCAGGACTCAGGGGAGATAGGGGGAGCCAGTGCAGG<br>AACACACCCCTCCCATGCCTGTTTCCCCATCTCCCCCCAATCCTGGGCAAGCTGGTC<br>TGCCTGGTGCTTTAAGCCTCCTTCAGATCACAACAGAAACCCTTCCATTCTATAACC<br>CATGTGTCAGACGAACACAACGCATGAGGTGGTTTTTGTCACCATGTATTCCATGGC<br>GTTACCTTCTCCTTTCCCCTGAGGAAACTGACAGGCAGGTGACTTTTCTGCTCACAT<br>TGAGCTCAGCCACTTTAACTCACGAACCCAGTCTCAGGCCATAACCCACTGCCCATT<br>TGTATGGAATCCCGAGCTCCCTGATGGCTCTAGGGGAGTGTGTCCCCTCTTTGGATG<br>CAGTTGTGTGTATATGTGTATGTATGTGTGTATGTGTGTATATGTGCACAT<br>ATGTGCGTGCGTGTATGTATTTGTGTATGTGTGTATATGTGTATGTGTCT<br>GTGTTCGTGTGTCTGTGTGGTGTGTGTATATATGTGTGCATGTGTATTTGTGTGTATA<br>CATGTGTGTAGGTGTATGCGTCTGTGTGTGTCTGTGTGTCTGTGTGGCATGTGTGTAT<br>TTTGTGTGTATGTGTCTCTGTGTCCATGTGTCCGTGTATGTGTGGTGTGTGTATAT<br>GTATGTGTGTTGTATGTATGTGTGTATGTGTATTTGTATATGTGTGCGTGTATGTG<br>CATGTGTATTTGTATGTGTGTGTATGTGTGTTTGTGTCTGTGTGTCTGTGTGTGGT<br>GTGTGTATATGTGCATTTGTGTATATGTGTGTGTATGTGTGTGTGTCTGTGTCCATGT<br>ATGTGTGTGTGTACGTGAGTACATTTGTGTGCCTGTGTGTATATGTGTGCACG<br>TATGTGCATGTGTGTGTGTGCATATTTGTGTGTGTATGTCTGTGTCCATGTGTCTG<br>CATATGTGTGGTGTGTGTATATTTGTGTATGTTTACGTGTGTGTGTGTGCGC<br>GCACGCGCGTGGTGTAGGGAAGGAAGGGCCCTGCCTTCCTCCCTTCCTGGTCCAGT<br>GTTTCTCCCTTCCTGCTCTGGCTGACCTCTGAGGTTCTGACTCCTGCAGTGTCTGGGC<br>TGGGGAGAGGGCCCGTCTCATGTGCCCACCACCGCTGTCATCCGGGTACTCTCTGGA<br>CCACGGATGTTGAAAGCCGACTTATTTTCCTGTGGGTGCTTTCCAGAGGTTCCTCAG<br>AGAGCCCCCGTGAGCCCTCCCACTGCACTTTCTGGGATATGGCAGATGCTGCGTCC<br>CTTTAGCTGCTGTCCCCAGCCCCTGGTTCTCAGATGGTCAACTCCACAATCTCTCGCT<br>GCTACAACCCTCTGGGGTCTCACAGGGCAGGATTCAGAGCAGTTCCAGTCTGGCC<br>TCAGAGTGGTTTCTTCTCCTCCCAGGAAGTCCTTGTGTTCCTTGCCCAGGCATGGGC<br>CAGAGTGCAGCTCCTCCCAAATGTGGCCCCTGCCCTCCTTCTCCATGCCACAAGTTG<br>CTTAAGTTTCCCTGAGCATGCACCAGGTGCCAGGCTTGTGTCTCTCACCTGCAGGGA<br>GCTCATTTTAGGGGGAGAAGGGAGAATACCTCTCCCTTTGATGCACATGGTAGATG<br>GAGTTCTCAGATACAGCAAGAGCTCTCGCCAGAGAAATCTTTTCACAAATTCTCCCT<br>CCATCCCATCCCAGAAGTGGATGTGAAGAGTCCAGAAAGCAGGTCCCAGGCCTGGA<br>GTTTCCAGTCATCGGTAAATTCCAAAGCTCTGGCCCCTTGCTCTGGAGTACCAGTCG |

-continued

| ADDITIONAL SEQUENCES |
|---|
| TCGGTAAATTGGAGTCCCCCAATTTACCGGGAGTCCTCCCTGGACTGGAGGTACCA<br>GTCGTCGGTAAATTCCAAAGCTCTGGCCCCTGGCTCTGGAGTTTCACATCTCTTGCA<br>TCTGTTGTCTCCTGGTGTCGTGGTCAAAGCTTCAGTTTTAATGTGCATTTCCAATTCA<br>TTCTTTCGGTCTGTGGTCCATCAGGCAGGCACTTGCCTTATGCCCAGCACAGTTTATT<br>TGGGAAAGTCCTGTCCCCCTTCCCCCTACACACACACTCAGGCCCAGTACAGCAGTG<br>CTGTGGGTGGTTGGGCCTGTAAGATCTGTAGGGGGCCCAAGGAAAGAAGACTCCCT<br>GGGGTAGTTTCGAGCTCTTGTCCTGCCCTGCCTGTCCCTTGGGTGCCCCGTGTTGGCT<br>GACATCGGGAATCTGCCCCTCCTGCAG |
| >Immunogenic sequence for anti-PE44.1 antibody: SEQ ID NO: 122<br>CAFEGEPALASDELPPSRDWR |

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

What is claimed is:

1. An expression construct encoding an antisense nucleic acid having a region of complementarity that is complementary with a pseudoexon sequence between exons 43 and 46 encoded by a human DYSF gene, wherein the region of complementarity is complementary with at least 8 contiguous nucleotides of a sequence as set forth in any one of SEQ ID NOs: 116, 117, 118, 119, 120, or 121.

2. The expression construct of claim 1, wherein the human DYSF gene comprises a c.4886+1249 (G>T) mutation.

3. The expression construct of claim 1, wherein the antisense nucleic acid expressed from the vector, when present in a cell that contains the human DYSF gene, alters splicing of a pre-messenger RNA expressed from the human DYSF gene such that the pseudoexon sequence is not incorporated between exons 44 and 45.

4. A recombinant AAV comprising the expression construct of claim 1.

5. The expression construct of claim 1, wherein the DYSF gene comprises a mutation that causes a premature stop codon.

6. The expression construct of claim 5, wherein the premature stop codon is within a region encoding a C2D domain of a dysferlin protein encoded by the DYSF gene.

7. The expression construct of claim 6, wherein the mutation that causes the premature stop codon is a c.3444_3445delTGinsAA mutation.

8. The expression construct of claim 1, wherein the antisense nucleic acid is 10-25 nucleotides in length.

9. The expression construct of claim 8, wherein the antisense nucleic acid is 20 nucleotides in length.

10. The expression construct of claim 1, wherein the region of complementarity is complementary with at least 10 contiguous nucleotides of a sequence as set forth in any one of SEQ ID NOs: 116, 117, 118, 119, 120, or 121.

11. The expression construct of claim 10, wherein the region of complementarity is complementary with at least 15 contiguous nucleotides of a sequence as set forth in any one of SEQ ID NOs: 116, 117, 118, 119, 120, or 121.

12. The expression construct of claim 11, wherein the region of complementarity is complementary with at least 20 contiguous nucleotides of a sequence as set forth in any one of SEQ ID NOs: 116, 117, 118, 119, 120, or 121.

13. A cell comprising the expression construct of claim 1.

14. A composition comprising the expression construct of claim 1 and a pharmaceutically-acceptable carrier.

15. The expression construct of claim 1, wherein the antisense nucleic acid comprises a sequence of any one of SEQ ID NOs: 53, 55, 57, or 82-98.

* * * * *

SEQUENCE LISTING

<160> NUMBER OF SEQ ID NOS: 134

<210> SEQ ID NO 1
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 1
aggtgcaaaa tgccgtgt                                                 18

<210> SEQ ID NO 2
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 2
ttcacccctg caaacacc                                                 18

<210> SEQ ID NO 3
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 3
cacacccgac accgacat                                                 18

<210> SEQ ID NO 4
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 4
ctccgcctca tctccagtg                                                19

<210> SEQ ID NO 5
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 5
cgactctgcc tgacctgga                                                19

<210> SEQ ID NO 6
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 6
aatggtgccc acgtccat                                                 18

<210> SEQ ID NO 7
<211> LENGTH: 21
<212> TYPE: DNA
<213> ORGANISM: Artificial Sequence

```
<220> FEATURE:
<223> OTHER INFORMATION: Synthetic Polynucleotide

<400> SEQUENCE: 7
tcgttctctc aggacagatg c                                              21

<210> SEQ ID NO 8
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 8
ctgagggttg gccgtctt                                                  18

<210> SEQ ID NO 9
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 9
gacccctttg tggaggtca                                                 19

<210> SEQ ID NO 10
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 10
gctccaccag cttggtctc                                                 19

<210> SEQ ID NO 11
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 11
gggggaaggt gtggcttat                                                 19

<210> SEQ ID NO 12
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 12
cagcgagtcc acgtcctc                                                  18

<210> SEQ ID NO 13
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 13
ccagctgctt gggattgc                                                  18
```

<210> SEQ ID NO 14
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 14
tcccacaatt cttgccaca                                              19

<210> SEQ ID NO 15
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 15
gcccaccaag tcctcttctc                                             20

<210> SEQ ID NO 16
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 16
aagccgggtc tggttctc                                               18

<210> SEQ ID NO 17
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 17
tcacctgagc ttcgtggaa                                              19

<210> SEQ ID NO 18
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 18
ttctccagtg gctccatgc                                              19

<210> SEQ ID NO 19
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 19
ccacctcgag taccgcaag                                              19

<210> SEQ ID NO 20
<211> LENGTH: 20
<212> TYPE: DNA
<213> ORGANISM: Artificial Sequence
<220> FEATURE:
<223> OTHER INFORMATION: Synthetic Polynucleotide

```
<400> SEQUENCE: 20
cgtacagctc caccacaatg                                              20

<210> SEQ ID NO 21
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 21
aacaccctta accccacctg                                              20

<210> SEQ ID NO 22
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 22
cggaggttcc tgatgacaca                                              20

<210> SEQ ID NO 23
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 23
ccccagcctc gtggtaga                                                18

<210> SEQ ID NO 24
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 24
accttcaggg tgtcaaaatc c                                            21

<210> SEQ ID NO 25
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 25
tgcctccata ggggagagg                                               19

<210> SEQ ID NO 26
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 26
tgcaggtcag ctcgaaca                                                18

<210> SEQ ID NO 27
```

```
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 27
tggagcccgt atttggaa                                                 18

<210> SEQ ID NO 28
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 28 tgcaggggc tgtagagg                                                  18

<210> SEQ ID NO 29
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 29
cgtctggctc tgcatgtg                                                 18

<210> SEQ ID NO 30
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 30
ccactcgtgc tgggattt                                                 19

<210> SEQ ID NO 31
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 31
ctgccagctg agcaagtctg                                               20

<210> SEQ ID NO 32
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 32
gccgccacag gatgaact                                                 18

<210> SEQ ID NO 33
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 33
```

```
ccgacacctc cttcctgtg                                              19

<210> SEQ ID NO 34
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 34
ttgtggttcc aactgtttta tactga                                      26

<210> SEQ ID NO 35
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 35
cctgggtgac agagcaaaac                                             20

<210> SEQ ID NO 36
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 36
gcctaaacaa gctcacatcc a                                           21

<210> SEQ ID NO 37
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 37
tgaaatctga gaacaaggaa agga                                        24

<210> SEQ ID NO 38
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 38
aatggaaggg tttctgttgt ga                                          22

<210> SEQ ID NO 39
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 39
cctcccatgc ctgtttcc                                               18

<210> SEQ ID NO 40
<211> LENGTH: 26
<212> TYPE: DNA
```

```
<213> ORGANISM: Artificial Sequence
<220> FEATURE:
<223> OTHER INFORMATION: Synthetic Polynucleotide

<400> SEQUENCE: 40
tatacacaca caactgcatc caaaga                                          26

<210> SEQ ID NO 41
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 41
acccagtctc aggccataac c                                               21

<210> SEQ ID NO 42
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 42
agggcccttc cttccctca                                                  18

<210> SEQ ID NO 43
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 43
atgtctgtgt ccatgtgtct gc                                              22

<210> SEQ ID NO 44
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 44
atctgagaac tccatctacc atgtg                                           25

<210> SEQ ID NO 45
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 45
tcacctgcag ggagctcat                                                  19

<210> SEQ ID NO 46
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 46
ggaaggggga caggactttt                                                 19
```

<210> SEQ ID NO 47
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 47
ttggagtccc ccaatttacc                                               20

<210> SEQ ID NO 48
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 48
gcaaatgcat cttctgagct t                                             21

<210> SEQ ID NO 49
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 49
gatgagctcc caccaagca                                                19

<210> SEQ ID NO 50
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 50
agcccctgga actcatacag a                                             21

<210> SEQ ID NO 51
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 51
cacctaccac ttccctcca                                                19

<210> SEQ ID NO 52
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 52
acctaccact tacctcca                                                 18

<210> SEQ ID NO 53
<211> LENGTH: 22
<212> TYPE: RNA
<213> ORGANISM: Artificial Sequence
<220> FEATURE:

<223> OTHER INFORMATION: Synthetic Polynucleotide

<400> SEQUENCE: 53
gaacaguagg ugucuucugc ag                                              22

<210> SEQ ID NO 54
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 54
ctgcagaaga cacctactgt tc                                              22

<210> SEQ ID NO 55
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 55
ccagggcugg uucaccuuca aa                                              22

<210> SEQ ID NO 56
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 56
tttgaaggtg aaccagccct gg                                              22

<210> SEQ ID NO 57
<211> LENGTH: 20
<212> TYPE: RNA
<213> ORGANISM: Artificial Sequence
<220> FEATURE:
<223> OTHER INFORMATION: Synthetic Polynucleotide

<400> SEQUENCE: 57
cuccaauccc ugcuuggugg                                                 20

<210> SEQ ID NO 58
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 58
ccaccaagca gggattggag                                                 20

<210> SEQ ID NO 59
<211> LENGTH: 20
<212> TYPE: RNA
<213> ORGANISM: Artificial Sequence
<220> FEATURE:
<223> OTHER INFORMATION: Synthetic Polynucleotide

<400> SEQUENCE: 59
acggcgugac uaguggugag                                                 20

```
<210> SEQ ID NO 60
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 60
taactacatc ccctgcacgc                                              20

<210> SEQ ID NO 61
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 61
cgaccgtctc accgatcttt                                              20

<210> SEQ ID NO 62
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 62
agtgaggacc cagtctcctt                                              20

<210> SEQ ID NO 63
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 63
agctcgaaca tcctccaatc c                                            21

<210> SEQ ID NO 64
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 64
gcccgtattt ggaaagatgt                                              20

<210> SEQ ID NO 65
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 65
ccgtctcacc gatcttttcg                                              20

<210> SEQ ID NO 66
<211> LENGTH: 20
<212> TYPE: DNA
<213> ORGANISM: Artificial Sequence
<220> FEATURE:
<223> OTHER INFORMATION: Synthetic Polynucleotide
```

```
<400> SEQUENCE: 66
cgtgcattat cgttccctgg                                                   20

<210> SEQ ID NO 67
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 67
aggcatcctt cttggcaatg g                                                 21

<210> SEQ ID NO 68
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 68
accacagtcc atgccatcac                                                   20

<210> SEQ ID NO 69
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 69
accacagtcc atgccatcac                                                   20

<210> SEQ ID NO 70
<211> LENGTH: 21
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (11)..(11)
<223> OTHER INFORMATION: n represents t or c

<400> SEQUENCE: 70
atgtggatga ngccatccag t                                                 21

<210> SEQ ID NO 71
<211> LENGTH: 21
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (11)..(11)
<223> OTHER INFORMATION: n represents a or t

<400> SEQUENCE: 71
ttgggctctc ngtggatgag a                                                 21

<210> SEQ ID NO 72
<211> LENGTH: 21
<212> TYPE: DNA
<213> ORGANISM: Artificial Sequence
<220> FEATURE:
<223> OTHER INFORMATION: Synthetic Polynucleotide
```

```
<220> FEATURE:
<221> NAME/KEY: misc_feature
<222> LOCATION: (11)..(11)
<223> OTHER INFORMATION: n represents c or a

<400> SEQUENCE: 72
gtgcttagat nctggcatgg g                                              21

<210> SEQ ID NO 73
<211> LENGTH: 21
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (11)..(11)
<223> OTHER INFORMATION: n represents g or a

<400> SEQUENCE: 73
gaccccagga ntgcttggtc c                                              21

<210> SEQ ID NO 74
<211> LENGTH: 22
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (11)..(11)
<223> OTHER INFORMATION: n represents t or a
<220> FEATURE:
<221> NAME/KEY: misc_feature
<222> LOCATION: (12)..(12)
<223> OTHER INFORMATION: n represents g or a

<400> SEQUENCE: 74
ttggtgaaga nnggaaccgc ta                                             22

<210> SEQ ID NO 75
<211> LENGTH: 22
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (11)..(11)
<223> OTHER INFORMATION: n represents g or t

<400> SEQUENCE: 75
ggattggagg naagtggtag gt                                             22

<210> SEQ ID NO 76
<211> LENGTH: 21
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (11)..(11)
<223> OTHER INFORMATION: n represents a or g

<400> SEQUENCE: 76
ctggcgcagg ncctcaggct a                                              21

<210> SEQ ID NO 77
```

```
<211> LENGTH: 21
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (11)..(11)
<223> OTHER INFORMATION: n represents c or g

<400> SEQUENCE: 77
agtgggtggg ngtgtgtcag g                                          21

<210> SEQ ID NO 78
<211> LENGTH: 21
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (11)..(11)
<223> OTHER INFORMATION: n represents c or t

<400> SEQUENCE: 78
tacacacaca ntcaggccca g                                          21

<210> SEQ ID NO 79
<211> LENGTH: 21
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (11)..(11)
<223> OTHER INFORMATION: n represents c or t

<400> SEQUENCE: 79
ttgggtgccc ngtgttggct g                                          21

<210> SEQ ID NO 80
<211> LENGTH: 21
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (11)..(11)
<223> OTHER INFORMATION: n represents a or g

<400> SEQUENCE: 80
tagggaagga ngggccctgc c                                          21

<210> SEQ ID NO 81
<211> LENGTH: 21
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (11)..(11)
<223> OTHER INFORMATION: n represents c or g

<400> SEQUENCE: 81
ctcatgtgcc naccaccgct g                                          21
```

```
<210> SEQ ID NO 82
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 82
caccuaccac uuaccuccaa uc                                              22

<210> SEQ ID NO 83
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 83
ccucugcauc cuccccucuc ug                                              22

<210> SEQ ID NO 84
<211> LENGTH: 20
<212> TYPE: RNA
<213> ORGANISM: Artificial Sequence
<220> FEATURE:
<223> OTHER INFORMATION: Synthetic Polynucleotide

<400> SEQUENCE: 84
gcgagagaaa uagcugccac                                                 20

<210> SEQ ID NO 85
<211> LENGTH: 20
<212> TYPE: RNA
<213> ORGANISM: Artificial Sequence
<220> FEATURE:
<223> OTHER INFORMATION: Synthetic Polynucleotide

<400> SEQUENCE: 85
auacagaguu ccucucuccc                                                 20

<210> SEQ ID NO 86
<211> LENGTH: 23
<212> TYPE: RNA
<213> ORGANISM: Artificial Sequence
<220> FEATURE:
<223> OTHER INFORMATION: Synthetic Polynucleotide

<400> SEQUENCE: 86
cagcaauuca ggaugccuag gaa                                             23

<210> SEQ ID NO 87
<211> LENGTH: 23
<212> TYPE: RNA
<213> ORGANISM: Artificial Sequence
<220> FEATURE:
<223> OTHER INFORMATION: Synthetic Polynucleotide

<400> SEQUENCE: 87
gccuaaacaa gcucacaucc aaa                                             23

<210> SEQ ID NO 88
<211> LENGTH: 20
<212> TYPE: RNA
<213> ORGANISM: Artificial Sequence
<220> FEATURE:
<223> OTHER INFORMATION: Synthetic Polynucleotide
```

```
<400> SEQUENCE: 88
auagcugcca cccucccucu                                              20

<210> SEQ ID NO 89
<211> LENGTH: 23
<212> TYPE: RNA
<213> ORGANISM: Artificial Sequence
<220> FEATURE:
<223> OTHER INFORMATION: Synthetic Polynucleotide

<400> SEQUENCE: 89
gucuucugca ggugcgagag aaa                                          23

<210> SEQ ID NO 90
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 90
uaugugacuu gaugacaucg ga                                           22

<210> SEQ ID NO 91
<211> LENGTH: 23
<212> TYPE: RNA
<213> ORGANISM: Artificial Sequence
<220> FEATURE:
<223> OTHER INFORMATION: Synthetic Polynucleotide

<400> SEQUENCE: 91
cagaccccgg uuuauaagug caa                                          23

<210> SEQ ID NO 92
<211> LENGTH: 23
<212> TYPE: RNA
<213> ORGANISM: Artificial Sequence
<220> FEATURE:
<223> OTHER INFORMATION: Synthetic Polynucleotide

<400> SEQUENCE: 92
gugagugacc acaacuaacu caa                                          23

<210> SEQ ID NO 93
<211> LENGTH: 23
<212> TYPE: RNA
<213> ORGANISM: Artificial Sequence
<220> FEATURE:
<223> OTHER INFORMATION: Synthetic Polynucleotide

<400> SEQUENCE: 93
ggagacuggg uccucacugc agg                                          23

<210> SEQ ID NO 94
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 94
uucaaaagcu gcauuucccc aa                                           22

<210> SEQ ID NO 95
<211> LENGTH: 23
```

```
<212> TYPE: RNA
<213> ORGANISM: Artificial Sequence
<220> FEATURE:
<223> OTHER INFORMATION: Synthetic Polynucleotide

<400> SEQUENCE: 95
ugggagcuca ucacuggcca ggg                                              23

<210> SEQ ID NO 96
<211> LENGTH: 23
<212> TYPE: RNA
<213> ORGANISM: Artificial Sequence
<220> FEATURE:
<223> OTHER INFORMATION: Synthetic Polynucleotide

<400> SEQUENCE: 96
agcucgccag ccccuggaac uca                                              23

<210> SEQ ID NO 97
<211> LENGTH: 23
<212> TYPE: RNA
<213> ORGANISM: Artificial Sequence
<220> FEATURE:
<223> OTHER INFORMATION: Synthetic Polynucleotide

<400> SEQUENCE: 97
gagguccugc gccagccccu gga                                              23

<210> SEQ ID NO 98
<211> LENGTH: 23
<212> TYPE: RNA
<213> ORGANISM: Artificial Sequence
<220> FEATURE:
<223> OTHER INFORMATION: Synthetic Polynucleotide

<400> SEQUENCE: 98
cugccccauc agcauuagcc uga                                              23

<210> SEQ ID NO 99
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 99
gattggaggt aagtggtagg tg                                               22

<210> SEQ ID NO 100
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 100
cagagagggg aggatgcaga gg                                               22

<210> SEQ ID NO 101
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 101
```
gtggcagcta tttctctcgc                                        20

<210> SEQ ID NO 102
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 102
gggagagagg aactctgtat                                        20

<210> SEQ ID NO 103
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 103
ttcctaggca tcctgaattg ctg                                    23

<210> SEQ ID NO 104
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 104
tttggatgtg agcttgttta ggc                                    23

<210> SEQ ID NO 105
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 105
agagggaggg tggcagctat                                        20

<210> SEQ ID NO 106
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 106
tttctctcgc acctgcagaa gac                                    23

<210> SEQ ID NO 107
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 107
tccgatgtca tcaagtcaca ta                                     22

<210> SEQ ID NO 108
<211> LENGTH: 23
<212> TYPE: DNA
<213> ORGANISM: Artificial Sequence

```
<220> FEATURE:
<223> OTHER INFORMATION: Synthetic Polynucleotide

<400> SEQUENCE: 108
ttgcacttat aaaccggggt ctg                                          23

<210> SEQ ID NO 109
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 109
ttgagttagt tgtggtcact cac                                          23

<210> SEQ ID NO 110
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 110
cctgcagtga ggacccagtc tcc                                          23

<210> SEQ ID NO 111
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 111
ttggggaaat gcagcttttg aa                                           22

<210> SEQ ID NO 112
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 112
ccctggccag tgatgagctc cca                                          23

<210> SEQ ID NO 113
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 113
tgagttccag gggctggcga gct                                          23

<210> SEQ ID NO 114
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 114
tccaggggct ggcgcaggac ctc                                          23
```

<210> SEQ ID NO 115
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 115
tcaggctaat gctgatgggg cag                                          23

<210> SEQ ID NO 116
<211> LENGTH: 177
<212> TYPE: DNA
<213> ORGANISM: Artificial Sequence
<220> FEATURE:
<223> OTHER INFORMATION: Synthetic Polynucleotide

<400> SEQUENCE: 116
aagacaccta ctgttccgat gtcatcaagt cacatattgc acttataaac cggggtctgt    60
tgagttagtt gtggtcactc accctgcagt gaggacccag tctccttggg gaaatgcagc   120
ttttgaaggt gaaccagccc tggccagtga tgagctccca ccaagcaggg attggag      177

<210> SEQ ID NO 117
<211> LENGTH: 6128
<212> TYPE: DNA
<213> ORGANISM: Homo sapiens

<400> SEQUENCE: 117
gtaactttcc tagagccctc acctccccca gagtagcagg ctcaggtaca agtggcctat    60
agaacctgga cacaaactct gcctcaggga gttcatagta ggttgggaaa cagacaaaca   120
cacaaaactg agaggtgcct ggatggagtt gtgttaagga ccaagtgctc tagaaggtca   180
gggaaggcca gtgtcagtac aggactttgg gaaaatgggg aaggcttcct ggaaggaata   240
ggactcttag gatagatgag attttgatag gctgggaggg agaagaaaat agtgttttaa   300
gaggggccaa aagcataggc aaaggtttga agaaaattg cttaatgtgt gtctagaaca   360
agaataaagc agaaagataa gtaaggctga gggtataggt tgggactctc aatggttaat   420
ggggaggagt gatggggaa aggagcagcg ttagtgactg ctatgcctag tcatggcaga   480
gtcccaggta aaagggaatg ctggtaacac tcacccggtc tttatttaaa attttgatat   540
tttgttcatc atggactatt gacactgatt ttaattttta aaatatttca ttaaagtact   600
gtttatctta ataactattt tggcccttcc ttacattttg tgcccaagat aagtgcgtga   660
gctgtctccc tctagtcatt gcctgagatg gagagggag atttgaagga ggaaaggagt   720
ctggagttat ggggaggtga cagaggtggg aggcagagta atgttgggaa gagaaagaaa   780
gaggaaagaa gagaggcagg ggtggggcct gatttgcctt tacaggcatg aggctagggt   840
cccctcttgt ctcctgaggc aggtttaggc ccagcatgtg tccttcaggt ggtgggcgga   900
ggcctggtat cccaccctgt agcctcacct ttcaagggac agaatggagc agttctcagc   960
ctaggcacca ctgacggcct ccaaggtgtg gtcatggcca gtgggttggt ttatatgctt  1020
gaagccttcc tgatgctaga ctaacccctgg gcactctgca gccccagctg ctgggtcgct  1080
ggctgagggg tgctgctgct tccaggaagc atggaggag acctccctgg gctagcctag  1140
gctgacatag gctgaccacc cctctctcat tccatatgct taagcagagg tcacagagag  1200
gaccccagcc tggtctcgtc atgtgtgtaa tgcagactgt tgtgtttctg ataagggcct  1260
ggcctctccc aatggagcag tagattggga gtgtgaagga ctcaggtgcc ccattcccac  1320

```
ggctggagcc aagaccagaa gcccatgtca gggtccaagt ggagtggtgt ggtgtgtggg    1380
agggggccct gtcttggcag gacacagccc acatctcaac ttcctgatgg ctgctccctc    1440
atcccatcca gaggcaaggc actcatgaag cctcaaagac aggtttggaa agtgttttca    1500
cagaagtgtt ttgtctcctc ctccagtgtg atccttacat caagatctcc atagggaaga    1560
aatcagtgag tgaccaggat aactacatcc cctgcacgct ggagcccgta tttggaaagt    1620 aaattgggc atcttgggtc ttggggtgga ggagccagac aggataaccc acagtctagt     1680
gggggagatg tgactggcac tgtgaagtcc gtatctcttg gagcaaaact gtattcctta    1740
aatcttgcat gtctatgggg gcatagcctc agttagccct tctttagctg ctaaagactt    1800
gatcccaaca gaagctccta gttaaatgct aaacaattac gtctaagatc agaaatctac    1860
atggcttgag ctcaggagtt tgagaccagt ctgggcaaca tagcaagacc ccatctctac    1920
aaaaaataaa aaacttagcc aggcatggta gtgcatgcct gtggttccag atacttggga    1980
ggctgaggtg ggaggatccc ttgagcctag gagtttgagc ttacagtgat ctgtgatcaa    2040
actactgcac tccagcctgg gtgacagagc aaaaccctgt ctcaaaaaaa aaaaaaaaa     2100 aaaagaaaga aaaagtagaa atctgtgtgt aagctcagaa gatgcatttg ctaattcttt    2160 tttttttta agataaactt ttactttgga ataattttag atttactaaa cagttacaga     2220
gacagtgcat aatttccact tactcaattt cccccactgg taaccccta ctcaatttcc     2280 cccactggta tcatcttacc taaccatggg acatttgtca aaatgaagaa atcatcattg    2340
gtgcattacg tttaaccaaa ctagactttt ttttaaagga tttcatgttt tcccactaat    2400
gtcctcttac taatgtctca ggatccaatc tgttatacga cattgcattt agtaattaat    2460
tctctgtaag tgtcccacat gtgtttgtag caagagctag aggaagaatg tagacccaag    2520
atagtaaaat gattcctgaa atctgagaac aaggaaagga agaatcaatg cccattgcat    2580
gggagtaatt cctaggcatc ctgaattgct gtttggatgt gagcttgttt aggccagaga    2640
ggggaggatg cagagggagg gtggcagcta tttctctcgc acctgcagaa gacacctact    2700
gttccgatgt catcaagtca catattgcac ttataaaccg gggtctgttg agttagttgt    2760
ggtcactcac cctgcagtga ggacccagtc tccttgggga aatgcagctt ttgaaggtga    2820
accagccctg gccagtgatg agctcccacc aagcagggat tggagggaag tggtaggtgg    2880
gagagaggaa ctctgtatga gttccagggg ctggcgagct ccaggggctg gcgcaggacc    2940
tcaggctaat gctgatgggg cagtgggcag ggcctgttcc acagtgggtg ggcgtgtgtc    3000
aggactcagg ggagataggg gagccagtgc aggaacacac cctcccatg cctgtttccc     3060 catctccccc caatcctggg caagctggtc tgcctggtgc tttaagcctc cttcagatca    3120
caacagaaac ccttccattc tataacccat gtgtcagacg aacacaacgc atgaggtggt    3180
ttttgtcacc atgtattcca tggcgttacc ttctcctttc ccctgaggaa actgacaggc    3240
aggtgacttt tctgctcaca ttgagctcag ccactttaac tcacgaaccc agtctcaggc    3300
cataacccac tgcccatttg tatggaatcc cgagctccct gatggctcta ggggagtgtg    3360
tccctctttt ggatgcagtt gtgtgtgtat atgtgtgtat gtatgtgtgt gtatgtgtgt    3420
atatgtgcac atatgtgcgt gcgtgtgtat gtatttgtgt gtatgtgtgt gtatgtgtgt    3480
atgtgtgtct gtgttcgtgt gtctgtgtgg tgtgtgtata tatgtgtgca tgtgtatttg    3540
tgtgtataca tgtgtgtagg tgtatgcgtg tgtgtgtgtc tgtgtgtctg tgtggcatgt    3600
gtgtattttg tgtgtatgtg tctctgtgtc catgtgtccg tgtatgtgtg tggtgtgtgt    3660
```

```
atatgtatgt gtgttgtatg tatgtgtgtg tatgtgtatt tgtatatgtg tgcgtgtatg    3720
tgcatgtgta tttgtatgtg tgtgtgtatg tgtgtttgtg tctgtgtgtc tgtgtgtggt    3780
gtgtgtatat gtgcatttgt gtatatgtgt gtgtatgtgt gtgtgtctgt gtccatgtat    3840
gtgtgtgtgt gtacgtgagt acatttgtgt gcctgtgtgt gtatatgtgt gcacgtatgt    3900
gcatgtgtgt gtgtgtgcat atttgtgtgt gtatgtctgt gtccatgtgt ctgcatatgt    3960
gtgtggtgtg tgtatatttg tgtatgttta cgtgtgtgtg tgtgtgtgcg cgcacgcgcg    4020
tggtgtaggg aaggaagggc cctgccttcc tcccttcctg gtccagtgtt tctcccttcc    4080
tgctctggct gacctctgag gttctgactc ctgcagtgtc tgggctgggg agagggcccg    4140
tctcatgtgc ccaccaccgc tgtcatccgg gtactctctg gaccacggat gttgaaagcc    4200
gacttatttt cctgtgggtg ctttccagag gttcctcaga gagcccccg tgagccctcc     4260 cactgcactt tctgggatat ggcagatgct gcgtcccttt agctgctgtc cccagcccct    4320
ggttctcaga tggtcaactc cacaatctct cgctgctaca accctctggg ggtctcacag    4380
ggcaggattc agagcagttc cagtctggcc tcagagtggt ttcttctcct cccaggaagt    4440
ccttgtgttc cttgcccagg catgggccag agtgcagctc ctcccaaatg tggcccctgc    4500
cctccttctc catgccacaa gttgcttaag tttccctgag catgcaccag gtgccaggct    4560
tgtgtctctc acctgcaggg agctcatttt aggggagaa gggagaatac ctctccctttt   4620 gatgcacatg gtagatggag ttctcagata cagcaagagc tctcgccaga gaatctttt    4680 cacaaattct ccctccatcc catcccagaa gtggatgtga agagtccaga aagcaggtcc    4740
caggcctgga gtttccagtc atcggtaaat tccaaagctc tggccccttg ctctggagta    4800
ccagtcgtcg gtaaattgga gtcccccaat ttaccgggag tcctccctgg actggaggta    4860
ccagtcgtcg gtaaattcca aagctctggc cctggctct ggagtttcac atctcttgca    4920
tctgttgtct cctggtgtcg tggtcaaagc ttcagtttta atgtgcattt ccaattcatt    4980
ctttcggtct gtggtccatc aggcaggcac ttgccttatg cccagcacag tttatttggg    5040
aaagtcctgt ccccccttccc cctacacaca cactcaggcc cagtacagca gtgctgtggg   5100
tggttgggcc tgtaagatct gtaggggggcc caaggaaaga agactccctg ggtagtttc    5160 gagctcttgt cctgccctgc ctgtcccttg ggtgccccgt gttggctgac atcgggaatc    5220
tgcccctcct gcaggatgtt cgagctgacc tgcactctgc ctctggagaa ggacctaaag    5280
atcactctct atgactatga cctcctctcc aaggacgaaa agatcggtga gacggtcgtc    5340
gacctggaga acaggctgct gtccaagttt ggggctcgct gtggactccc acagacctac    5400
tgtgtgtacg tggatggggg ctggctgcct gcttctctga acacacacca cccctgtctt    5460
ctctgacaac acaccaccac tgagcactta ctgtgtgcca gccctgggct agcacttcc    5520 taggcattct ctcattgagt ccaatgggag tcctatcccc actccacaga tgaagaaact    5580
gaagcccaga gatgttattg cttgtaagtg gtggaattag gatttgaacc aagaacctgg    5640
ctcatcacat tgttataatc cagttatctg taatgcacat agaaggccta gagagggcta    5700
ggtacctgga aagggagaga gggaaggaag gcaggaaaga agcaggggaa acagatgaga    5760
ggacatgtgt gctgcaactg ggcccgaagg ggaattttgt gatggtttat gtcagggaa    5820 tgcatgtgag gactgcaccc ctcttcccac catctcaagt cttctctggg tctgattatc    5880
taactctgga aattgaaaac atttaagttg caattccgta cttaaatgag tccttttctc    5940
tctgagcctc catttctcca tctgtaaaat ggggatgccc agtcatggtg agcaatcaga    6000
tgggacaccc actgtaaaag caaggagtgg gcaatgctgt acatgggggt acaccagtcc    6060
```

```
ctgcatgccc ctctaccctc atgagtgtcc ttgaagcatc tcatctatgt cttgtgcttg    6120
ctcctcag                                                              6128

<210> SEQ ID NO 118
<211> LENGTH: 6132
<212> TYPE: DNA
<213> ORGANISM: Homo sapiens

<400> SEQUENCE: 118
gtaactttcc tagagccctc acctccccca gagtagcagg ctcaggtaca agtggcctat      60
agaacctgga cacaaactct gcctcaggga gttcatagta ggttgggaaa cagacaaaca     120
cacaaaactg agaggtgcct ggatggagtt gtgttaagga ccaagtgctc tagaaggtca     180
gggaaggcca gtgtcagtac aggactttgg gaaaatgggg aaggcttcct ggaaggaata     240
ggactcttag gatagatgag attttgatag gctgggaggg agaagaaaat agtgttttaa     300
gaggggccaa aagcataggc aaggtttga aagaaaattg cttaatgtgt gtctagaaca      360
agaataaagc agaaagataa gtaaggctga gggtataggt tgggactctc aatggtgaat     420
ggggaggagt gatgggggaa aggagcagcg ttagtgactg ctatgcctag tcatggcaga     480
gtcccaggta aagggaatg ctggtaacac tcacccggtc tttatttaaa attttgatat      540
tttgttcatc atggactatt gacactgatt ttaattttta aaatatttca ttaaagtact     600
gtttatctta ataactattt tggccctccc ttacattttg tgcccaagat aagtgcgtga     660
gctgtctccc tctagtcatt gcctgagatg gagaggggag atttgaagga ggaaaggagt     720
ctggagttat ggggaggtga cagaggtggg aggcagagta atgttgggaa gagaaagaaa     780
gaggaaagaa gagaggcagg ggtgggcct gatttgcctt tacaggcatg aggctagggt       840
cccctcttgt ctcctgaggc aggtttaggc ccagcatgtg tccttcaggt ggtgggtgga     900
ggcctggtat cccaccctgt agcctcacct ttcaagggac agaatggagc agttctcagc     960
ctaggcacca ctgacggcct ccaaggtgtg gtcatggcca gtgggttggt ttatatgctt    1020
gaagccttcc tgatgctaga ctaaccctgg gcactctgca gccccagctg ctgggtcgct    1080
ggctgagggg tgctgctgct tccaggaagc atggaggag acctccctgg gctagcctag     1140
gctgacatag gctgaccacc cctctctcat tccatatgct taagcagagg tcacagagag    1200
gaccccagcc tggtctcgtc atgtgtgtaa tgcagactgt tgtgtttctg ataagggcct    1260
ggcctctccc aatggagcag tagattggga gtgtgaagga ctcaggtgcc ccattccac     1320 ggctggagcc aagaccagaa gcccatgtca gggtccaagt ggagtggtgt ggtgtgtggg    1380 aggggggccct gtcttggcag gacacagccc acatctcaac ttcctgatgg ctgctccctc   1440
atcccatcca gaggcaaggc actcatgaag cctcaaagac aggtttggaa agtgttttca    1500
cagaagtgtt ttgtctcctc ctccagtgtg atccttacat caagatctcc ataggaaga    1560 aatcagtgag tgaccaggat aactacatcc cctgcacgct ggagcccgta tttggaaagt    1620 aaattgggc atcttgggtc ttggggtgga ggagccagac aggataaccc acagtctagt     1680
gggggagatg tgactggcac tgtgaagtcc gtatctcttg gagcaaaact gtattcctta    1740
aatcttgcat gtctatgggg gcatagcctc agttagccc tctttagctg ctaaagactt     1800
gatcccaaca gaagctccta gttaaatgct aaacaattac gtctaagatc agaaatctac    1860
atggcttgag ctcaggagtt tgagaccagt ctgggcaaca tagcaagacc ccatctctac    1920
aaaaaataaa aaacttagcc aggcatggta gtgcatgcct gtggttccag atacttggga    1980
```

-continued

```
ggctgaggtg ggaggatccc ttgagcctag gagtttgagc ttacagtgat ctgtgatcaa    2040
actactgcac tccagcctgg gtgacagagc aaaaccctgt ctcaaaaaaa aaaaaaaaaa    2100 aaagaaaga aaagtagaa atctgtgtgt aagctcagaa gatgcatttg ctaattcttt     2160
ttttttttta agataaactt ttactttgga ataattttag atttactaaa cagttacaga   2220
gacagtgcat aatttccact tactcaattt cccccactgg taacccctta ctcaatttcc   2280
cccactggta tcatcttacc taaccatggg acatttgtca aaatgaagaa atcatcattg   2340
gtgcattacg tttaaccaaa ctagactttt ttttaaagga tttcatgttt tcccactaat   2400
gtcctcttac taatgtctca ggatccaatc tgttatacga cattgcattt agtaattaat   2460
tctctgtaag tgtcccacat gtgtttgtag caagagctag aggaagaatg tagacccaag   2520
atagtaaaat gattcctgaa atctgagaac aaggaaagga agaatcaatg cccattgcat   2580
gggagtaatt cctaggcatc ctgaattgct gtttggatgt gagcttgttt aggccagaga   2640
ggggaggatg cagagggagg gtggcagcta tttctctcgc acctgcagaa gacacctact   2700
gttccgatgt catcaagtca catattgcac ttataaaccg gggtctgttg agttagttgt   2760
ggtcactcac cctgcagtga ggacccagtc tccttgggga aatgcagctt ttgaaggtga   2820
accagccctg gccagtgatg agctcccacc aagcagggat tggagggaag tggtaggtgg   2880
gagagaggaa ctctgtatga gttccagggg ctggcgagct ccaggggctg gcgcagggcc   2940
tcaggctaat gctgatgggg cagtgggcag ggcctgttcc acagtgggtg ggggtgtgtc   3000
aggactcagg ggagataggg gagccagtgc aggaacacac ccctcccatg cctgtttccc   3060
catctccccc caatcctggg caagctggtc tgcctggtgc tttaagcctc cttcagatca   3120
caacagaaac ccttccattc tataacccat gtgtcagacg aacacaacgc atgaggtggt   3180
ttttgtcacc atgtattcca tggcgttacc ttctcctttc ccctgaggaa actgacaggc   3240
aggtgacttt tctgctcaca ttgagctcag ccactttaac tcacgaaccc agtctcaggc   3300 cataaccac tgcccatttg tatggaatcc cgagctccct gatggctcta ggggagtgtg   3360
tccctctttt ggatgcagtt gtgtgtgtat atgtgtgtat gtatgtgtgt gtatgtgtgt   3420
atatgtgcac atatgtgcgt gcgtgtgtat gtatttgtgt gtatgtgtgt gtatatgtgt   3480
atgtgtgtct gtgttcgtgt gtctgtgtgg tgtgtgtata tatgtgtgca tgtgtatttg   3540
tgtgtataca tgtgtgtagg tgtatgcgtc tgtgtgtgtc tgtgtgtctg tgtggcatgt   3600
gtgtattttg tgtgtgtgta tgtgtctctg tgtccatgtg tccgtgtatg tgtgtggtgt   3660
gtgtatatgt atgtgtgttg tatgtatgtg tgtgtatgtg tatttgtata tgtgtgcgtg   3720
tatgtgcatg tgtatttgta tgtgtgtgtg tatgtgtgtt tgtgtctgtg tgtctgtgtg   3780
tggtgtgtgt atatgtgcat ttgtgtatat gtgtgtgtat gtgtgtgtgt ctgtgtccat   3840
gtatgtgtgt gtgtgtacgt gagtacattt gtgtgcctgt gtgtgtatat gtgtgcacgt   3900
atgtgcatgt gtgtgtgtgt gcatatttgt gtgtgtatgt ctgtgtccat gtgtctgcat   3960
atgtgtgtgg tgtgtgtata tttgtgtatg tttacgtgtg tgtgtgtgtg tgcgcgcacg   4020
cgcgtggtgt agggaaggag gggccctgcc ttcctcccctt cctggtccag tgtttctccc   4080
ttcctgctct ggctgacctc tgaggttctg actcctgcag tgtctgggct ggggagaggg   4140
cccgtctcat gtgccgacca ccgctgtcat ccgggtactc tctggaccac ggatgttgaa   4200
agccgactta ttttcctgtg ggtgcttccc agaggttcct cagagagccc ccgtgagcc    4260 ctcccactgc actttctggg atatggcaga tgctgcgtcc ctttagctgc tgtccccagc   4320
ccctggttct cagatggtca actccacaat ctctcgctgc tacaaccctc tgggggtctc   4380
```

```
acagggcagg attcagagca gttccagtct ggcctcagag tggtttcttc tcctcccagg      4440
aagtccttgt gttccttgcc caggcatggg ccagagtgca gctcctccca aatgtggccc      4500
ctgccctcct tctccatgcc acaagttgct taagtttccc tgagcatgca ccaggtgcca      4560
ggcttgtgtc tctcacctgc agggagctca ttttaggggg agaagggaga atacctctcc      4620
ctttgatgca catggtagat ggagttctca gatacagcaa gagctctcgc cagagaaatc      4680
ttttcacaaa ttctccctcc atcccatccc agaagtggag gtgaagagtc cagaaagcag      4740
gtcccaggcc tggagtttcc agtcatcggt aaattccaaa gctctggccc cttgctctgg      4800
agtaccagtc gtcggtaaat tggagtcccc caatttaccg ggagtcctcc ctggactgga      4860
ggtaccagtc gtcggtaaat tccaaagctc tggcccctgg ctctggagtt tcacatctct      4920
tgcatctgtt gtctcctggt gtcgtggtca aagcttcagt tttaatgtgc atttccaatt      4980
cattctttcg gtctgtggtc catcaggcag gcacttgcct tatgcccagc acagtttatt      5040
tgggaaagtc ctgtccccct tccccctaca cacacattca ggcccagtac agcagtgctg      5100
tgggtggttg ggcctgtaag atctgtaggg ggcccaagga agaagactc cctggggtag       5160 tttcgagctc ttgtcctgcc ctgcctgtcc cttgggtgcc ctgtgttggc tgacatcggg      5220
aatctgcccc tcctgcagga tgttcgagct gacctgcact ctgcctctgg agaaggacct      5280
aaagatcact ctctatgact atgacctcct ctccaaggac gaaagatcg gtgagacggt       5340 cgtcgacctg gagaacaggc tgctgtccaa gtttggggct cgctgtggac tcccacagac      5400
ctactgtgtg tacgtggatg ggggctggct gcctgcttct ctgacaacac accacccctg      5460
tcttctctga caacacacca ccactgagca cttactgtgt gccagccctg ggcttagcac      5520
ttcctaggca ttctctcatt gagtccaatg ggagtcctat ccccactcca cagatgaaga      5580
aactgaagcc cagagatgtt attgcttgta agtggtggaa ttaggatttg aaccaagaac      5640
ctggctcatc acattgttat aatccagtta tctgtaatgc acatagaagg cctagagagg      5700
gctaggtacc tggaaaggga gagagggaag gaaggcagga agaagcagg ggaaacagat       5760 gagaggacat gtgtgctgca actgggcccg aaggggaatt ttgtgatggt ttatgtcagg      5820
ggaatgcatg tgaggactgc acccctcttc ccaccatctc aagtcttctc tgggtctgat      5880
tatctaactc tggaaattga aaacatttaa gttgcaattc cgtacttaaa tgagtccttt      5940
tctctctgag cctccatttc tccatctgta aaatggggat gcccagtcat ggtgagcaat      6000
cagatgggac acccactgta aaagcaagga gtgggcaatg ctgtacatgg gggtacacca      6060
gtccctgcat gcccctctac cctcatgagt gtccttgaag catctcatct atgtcttgtg      6120
cttgctcctc ag                                                          6132
```

<210> SEQ ID NO 119
<211> LENGTH: 6126
<212> TYPE: DNA
<213> ORGANISM: Homo sapiens

<400> SEQUENCE: 119

```
gtaactttcc tagagccctc acctccccca gagtagcagg ctcaggtaca agtggcctat        60
agaacctgga cacaaactct gcctcaggga gttcatagta ggttgggaaa cagacaaaca       120
cacaaaactg agaggtgcct ggatggagtt tgttaagga ccaagtgctc tagaaggtca        180
gggaaggcca gtgtcagtac aggactttgg gaaaatgggg aaggcttcct ggaaggaata       240
ggactcttag gatagatgag attttgatag gctgggaggg agaagaaaat agtgttttaa       300
```

```
gaggggccaa aagcataggc aaaggtttga aagaaaattg cttaatgtgt gtctagaaca    360
agaataaagc agaaagataa gtaaggctga gggtataggt tgggactctc aatggtgaat    420
ggggaggagt gatgggggaa aggagcagcg ttagtgactg ctatgcctag tcatggcaga    480
gtcccaggta aagggaatg ctggtaacac tcacccggtc tttatttaaa attttgatat     540
tttgttcatc atggactatt gacactgatt ttaattttta aatatttca ttaaagtact     600 gtttatctta ataactattt tggcccttcc ttacattttg tgcccaagat aagtgcgtga    660
gctgtctccc tctagtcatt gcctgagatg gagagggag atttgaagga ggaaaggagt     720
ctggagttat gggaggtga cagaggtggg aggcagagta atgttgggaa gagaaagaaa     780
gaggaaagaa gagaggcagg ggtggggcct gatttgcctt tacaggcatg aggctagggt    840
cccctcttgt ctcctgaggc aggtttaggc ccagcatgtg tccttcaggt ggtgggtgga    900
ggcctggtat cccaccctgt agcctcacct ttcaagggac agaatggagc agttctcagc    960
ctaggcacca ctgacggcct ccaaggtgtg gtcatggcca gtgggttggt ttatatgctt    1020
gaagccttcc tgatgctaga ctaaccctgg gcactctgca gccccagctg ctgggtcgct    1080
ggctgagggg tgctgctgct tccaggaagc atggagggag acctccctgg gctagcctag    1140
gctgacatag gctgaccacc cctctctcat tccatatgct taagcagagg tcacagagag    1200
gaccccagcc tggtctcgtc atgtgtgtaa tgcagactgt tgtgtttctg ataagggcct    1260
ggcctctccc aatggagcag tagattggga gtgtgaagga ctcaggtgcc ccattcccac    1320
ggctggagcc aagaccagaa gcccatgtca gggtccaagt ggagtggtgt ggtgtgtggg    1380 aggggggccct gtcttggcag gacacagccc acatctcaac ttcctgatgg ctgctccctc    1440
atcccatcca gaggcaaggc actcatgaag cctcaaagac aggtttggaa agtgttttca    1500
cagaagtgtt ttgtctcctc ctccagtgtg atccttacat caagatctcc atagggaaga    1560
aatcagtgag tgaccaggat aactacatcc cctgcacgct ggagcccgta tttggaaagt    1620
aaattggggc atcttgggtc ttggggtgga ggagccagac aggataaccc acagtctagt    1680
gggggagatg tgactggcac tgtgaagtcc gtatctcttg gagcaaaact gtattcctta    1740
aatcttgcat gtctatgggg gcatagcctc agttagccct tctttagctg ctaaagactt    1800
gatcccaaca gaagctccta gttaaatgct aaacaattac gtctaagatc agaaatctac    1860
atggcttgag ctcaggagtt tgagaccagt ctgggcaaca tagcaagacc ccatctctac    1920
aaaaaataaa aaacttagcc aggcatggta gtgcatgcct gtggttccag atacttggga    1980
ggctgaggtg ggaggatccc ttgagcctag gagtttgagc ttacagtgat ctgtgatcaa    2040
actactgcac tccagcctgg gtgacagagc aaaaccctgt ctcaaaaaaa aaaaaaaaaa    2100
aaaagaaaga aaaagtagaa atctgtgtgt aagctcagaa gatgcatttg ctaattcttt    2160 tttttttta agataaactt ttactttgga ataattttag atttactaaa cagttacaga    2220
gacagtgcat aatttccact tactcaattt cccccactgg taacccctta ctcaatttcc    2280
cccactggta tcatcttacc taaccatggg acatttgtca aaatgaagaa atcatcattg    2340
gtgcattacg tttaaccaaa ctagactttt ttttaaagga tttcatgttt tcccactaat    2400
gtcctcttac taatgtctca ggatccaatc tgttatacga cattgcattt agtaattaat    2460
tctctgtaag tgtcccacat gtgtttgtag caagagctag aggaagaatg tagacccaag    2520
atagtaaaat gattcctgaa atctgagaac aaggaaagga agaatcaatg cccattgcat    2580
gggagtaatt cctaggcatc ctgaattgct gtttggatgt gagcttgttt aggccagaga    2640
ggggaggatg cagagggagg gtggcagcta tttctctcgc acctgcagaa gacacctact    2700
```

```
gttccgatgt catcaagtca catattgcac ttataaaccg gggtctgttg agttagttgt   2760
ggtcactcac cctgcagtga ggacccagtc tccttgggga aatgcagctt ttgaaggtga   2820
accagccctg gccagtgatg agctcccacc aagcagggat tggagggaag tggtaggtgg   2880
gagagaggaa ctctgtatga gttccagggg ctggcgagct ccaggggctg cgcagggcc    2940 tcaggctaat gctgatgggg cagtgggcag ggcctgttcc acagtgggtg ggggtgtgtc   3000
aggactcagg ggagataggg gagccagtgc aggaacacac ccctcccatg cctgtttccc   3060
catctccccc caatcctggg caagctggtc tgcctggtgc tttaagcctc cttcagatca   3120
caacagaaac ccttccattc tataacccat gtgtcagacg aacacaacgc atgaggtggt   3180
ttttgtcacc atgtattcca tggcgttacc ttctcctttc ccctgaggaa actgacaggc   3240
aggtgacttt tctgctcaca ttgagctcag ccactttaac tcacgaaccc agtctcaggc   3300
cataacccac tgcccatttg tatggaatcc cgagctccct gatggctcta ggggagtgtg   3360
tccctctttt ggatgcagtt gtgtgtgtat atgtgtgtat gtatgtgtgt gtatgtgtgt   3420
atatgtgcac atatgtgcgt gcgtgtgtat gtatttgtgt gtgtgtgtgt atatgtgtat   3480
gtgtgtgttc gtgtgtctgt gtggtgtgtg tatatatgtg tgcatgtgta tttgtgtgta   3540
tacatgtgtg taggtgtatg cgtctgtgtg tgtctgtgtg tctgtgtggc atgtgtgtat   3600
tttgtgtgtg tgtatgtgtc tctgtgtcca tgtgtccgtg tatgtgtgtg gtgtgtgtat   3660
atgtatgtgt gttgtatgta tgtgtgtgta tgtgtatttg tatatgtgtg cgtgtatgtg   3720
catgtgtatt tgtatgtgtg tgtgtatgtg tgttttgtgtc tgtgtgtctg tgtgtggtgt   3780
gtgtatatgt gcatttgtgt atatgtgtgt gtatgtgtgt gtgtctgtgt ccatgtatgt   3840
gtgtgtgtgt acgtgagtac atttgtgtgc ctgtgtgtgt atatgtgtgc acgtatgtgc   3900
atgtgtgtgt gtgtgcatat ttgtgtgtgt atgtctgtgt ccatgtgtct gcatatgtgt   3960
gtggtgtgtg tatatttgtg tatgtttacg tgtgtgtgtg tgtgtgcgcg cacgcgcgtg   4020
gtgtagggaa ggaagggccc tgccttcctc ccttcctggt ccagtgtttc tcccttcctg   4080
ctctggctga cctctgaggt tctgactcct gcagtgtctg ggctggggag agggcccgtc   4140
tcatgtgccc accaccgctg tcatccgggt actctctgga ccacggatgt tgaaagccga   4200
cttattttcc tgtgggtgct ttccagaggt tcctcagaga gcccccgtg agccctccca    4260 ctgcactttc tgggatatgg cagatgctgc gtcccttttag ctgctgtccc cagccctgg   4320 ttctcagatg gtcaactcca caatctctcg ctgctacaac cctctggggg tctcacaggg   4380
caggattcag agcagttcca gtctggcctc agagtggttt cttctcctcc caggaagtcc   4440
ttgtgttcct tgcccaggca tgggccagag tgcagctcct cccaaatgtg gcccctgccc   4500
tccttctcca tgccacaagt tgcttaagtt ccctgagca tgcaccaggt gccaggcttg    4560
tgtctctcac ctgcagggag ctcatttttag ggggagaagg gagaatacct ctcccttttga  4620 tgcacatggt agatggagtt ctcagataca gcaagagctc tcgccagaga aatcttttca   4680
caaattctcc ctccatccca tcccagaagt ggatgtgaag agtccagaaa gcaggtccca   4740
ggcctggagt ttccagtcat cggtaaaattc caaagctctg gcccccttgct ctggagtacc  4800 agtcgtcggt aaattggagt cccccaattt accgggagtc ctccctggac tggaggtacc   4860
agtcgtcggt aaattccaaa gctctggccc ctggctctgg agtttcacat ctcttgcatc   4920
tgttgtctcc tggtgtcgtg gtcaaagctt cagttttaat gtgcatttcc aattcattct   4980
ttcggtctgt ggtccatcag gcaggcactt gccttatgcc cagcacagtt tatttgggaa   5040
```

```
agtcctgtcc cccttccccc tacacacaca ttcaggccca gtacagcagt gctgtgggtg      5100
gttgggcctg taagatctgt aggggggccca aggaaagaag actccctggg gtagtttcga    5160
gctcttgtcc tgccctgcct gtcccttggg tgccctgtgt tggctgacat cgggaatctg     5220
cccctcctgc aggatgttcg agctgacctg cactctgcct ctggagaagg acctaaagat    5280
cactctctat gactatgacc tcctctccaa ggacgaaaag atcggtgaga cggtcgtcga     5340
cctggagaac aggctgctgt ccaagtttgg ggctcgctgt ggactccac  agacctactg     5400 tgtgtacgtg gatgggggct ggctgcctgc ttctctgaca acacaccacc cctgtcttct    5460
ctgacaacac accaccactg agcacttact gtgtgccagc cctgggctta gcacttccta    5520
ggcattctct cattgagtcc aatgggagtc ctatccccac tccacagatg aagaaactga    5580
agcccagaga tgttattgct tgtaagtggt ggaattagga tttgaaccaa gaacctggct    5640
catcacattg ttataatcca gttatctgta atgcacatag aaggcctaga gagggctagg    5700
tacctggaaa gggagagagg gaaggaaggc aggaaagaag caggggaaac agatgagagg    5760
acatgtgtgc tgcaactggg cccgaagggg aattttgtga tggtttatgt caggggaatg   5820
catgtgagga ctgcacccct cttcccacca tctcaagtct tctctgggtc tgattatcta    5880
actctggaaa ttgaaaacat ttaagttgca attccgtact taaatgagtc cttttctctc    5940
tgagcctcca tttctccatc tgtaaaatgg ggatgcccag tcatggtgag caatcagatg    6000
ggacacccac tgtaaaagca aggagtgggc aatgctgtac atgggggtac accagtccct    6060
gcatgcccct ctaccctcat gagtgtcctt gaagcatctc atctatgtct tgtgcttgct    6120
cctcag                                                                6126

<210> SEQ ID NO 120
<211> LENGTH: 1070
<212> TYPE: DNA
<213> ORGANISM: Artificial Sequence
<220> FEATURE:
<223> OTHER INFORMATION: Synthetic Polynucleotide

<400> SEQUENCE: 120
gtaaattggg gcatcttggg tcttggggtg gaggagccag acaggataac ccacagtcta      60
gtgggggaga tgtgactggc actgtgaagt ccgtatctct tggagcaaaa ctgtattcct     120
taaatcttgc atgtctatgg gggcatagcc tcagttagcc cttctttagc tgctaaagac    180
ttgatcccaa cagaagctcc tagttaaatg ctaaacaatt acgtctaaga tcagaaatct    240
acatggcttg agctcaggag tttgagacca gtctgggcaa catagcaaga ccccatctct    300
acaaaaaata aaaaacttag ccaggcatgg tagtgcatgc ctgtggttcc agatacttgg    360
gaggctgagg tgggaggatc ccttgagcct aggagtttga gcttacagtg atctgtgatc     420
aaactactgc actccagcct gggtgacaga gcaaaccct gtctcaaaaa aaaaaaaaa      480 aaaaagaaa gaaaagtag aaatctgtgt gtaagctcag aagatgcatt tgctaattct     540 ttttttttt taagataaac ttttacttg gaataatttt agatttacta acagttaca      600 gagacagtgc ataatttcca cttactcaat ttcccccact ggtaacccct tactcaattt   660
cccccactgg tatcatctta cctaaccatg ggacatttgt caaaatgaag aaatcatcat     720
tggtgcatta cgtttaacca aactagactt ttttttaaag gatttcatgt tttcccacta   780
atgtcctctt actaatgtct caggatccaa tctgttatac gacattgcat ttagtaatta     840
attctctgta agtgtcccac atgtgtttgt agcaagagct agaggaagaa tgtagaccca    900
agatagtaaa atgattcctg aaatctgaga acaaggaaag gaagaatcaa tgcccattgc   960
```

| atgggagtaa ttcctaggca tcctgaattg ctgtttggat gtgagcttgt ttaggccaga | 1020 |
| gaggggagga tgcagaggga gggtggcagc tatttctctc gcacctgcag | 1070 |

<210> SEQ ID NO 121
<211> LENGTH: 3616
<212> TYPE: DNA
<213> ORGANISM: Artificial Sequence
<220> FEATURE:
<223> OTHER INFORMATION: Synthetic Polynucleotide

<400> SEQUENCE: 121

| gtaaattggg gcatcttggg tcttggggtg gaggagccag acaggataac ccacagtcta | 60 |
| gtgggggaga tgtgactggc actgtgaagt ccgtatctct tggagcaaaa ctgtattcct | 120 |
| taaatcttgc atgtctatgg gggcatagcc tcagttagcc cttctttagc tgctaaagac | 180 |
| ttgatcccaa cagaagctcc tagttaaatg ctaaacaatt acgtctaaga tcagaaatct | 240 |
| acatggcttg agctcaggag tttgagacca gtctgggcaa catagcaaga ccccatctct | 300 |
| acaaaaaata aaaaacttag ccaggcatgg tagtgcatgc ctgtggttcc agatacttgg | 360 |
| gaggctgagg tgggaggatc ccttgagcct aggagtttga gcttacagtg atctgtgatc | 420 |
| aaactactgc actccagcct gggtgacaga gcaaaccct gtctcaaaaa aaaaaaaaa | 480 |
| aaaaaagaaa gaaaaagtag aaatctgtgt gtaagctcag aagatgcatt tgctaattct | 540 |
| tttttttttt taagataaac ttttactttg gaataatttt agatttacta aacagttaca | 600 |
| gagacagtgc ataatttcca cttactcaat ttcccccact ggtaacccct tactcaattt | 660 |
| cccccactgg tatcatctta cctaaccatg ggacatttgt caaaatgaag aaatcatcat | 720 |
| tggtgcatta cgtttaacca aactagactt tttttaaag gatttcatgt tttcccacta | 780 |
| atgtcctctt actaatgtct caggatccaa tctgttatac gacattgcat ttagtaatta | 840 |
| attctctgta agtgtcccac atgtgttttgt agcaagagct agaggaagaa tgtagaccca | 900 |
| agatagtaaa atgattcctg aaatctgaga acaaggaaag gaagaatcaa tgcccattgc | 960 |
| atgggagtaa ttcctaggca tcctgaattg ctgtttggat gtgagcttgt ttaggccaga | 1020 |
| gaggggagga tgcagaggga gggtggcagc tatttctctc gcacctgcag aagacaccta | 1080 |
| ctgttccgat gtcatcaagt cacatattgc acttataaac cggggtctgt tgagttagtt | 1140 |
| gtggtcactc accctgcagt gaggacccag tctccttggg gaaatgcagc ttttgaaggt | 1200 |
| gaaccagccc tggccagtga tgagctccca ccaagcaggg attggaggga agtggtaggt | 1260 |
| gggagagagg aactctgtat gagttccagg ggctggcgag ctccaggggc tggcgcagga | 1320 |
| cctcaggcta atgctgatgg ggcagtgggc agggcctgtt ccacagtggg tgggcgtgtg | 1380 |
| tcaggactca ggggagatag gggagccagt gcaggaacac acccctccca tgcctgtttc | 1440 |
| cccatctccc cccaatcctg ggcaagctgg tctgcctggt gctttaagcc tccttcagat | 1500 |
| cacaacagaa acccttccat tctataaccc atgtgtcaga cgaacacaac gcatgaggtg | 1560 |
| gttttttgtca ccatgtattc catggcgtta ccttctcctt tcccctgagg aaactgacag | 1620 |
| gcaggtgact tttctgctca cattgagctc agccacttta actcacgaac ccagtctcag | 1680 |
| gccataaccc actgcccatt tgtatggaat cccgagctcc ctgatggctc taggggagtg | 1740 |
| tgtcccctct ttggatgcag ttgtgtgtgt atatgtgtgt atgtatgtgt gtgtatgtgt | 1800 |
| gtatatgtgc acatatgtgc gtgcgtgtgt atgtatttgt gtgtatgtgt gtgtatatgt | 1860 |
| gtatgtgtgt ctgtgttcgt gtgtctgtgt ggtgtgtgta tatatgtgtg catgtgtatt | 1920 |

```
tgtgtgtata catgtgtgta ggtgtatgcg tctgtgtgtg tctgtgtgtc tgtgtggcat    1980
gtgtgtattt tgtgtgtatg tgtctctgtg tccatgtgtc cgtgtatgtg tgtggtgtgt    2040
gtatatgtat gtgtgttgta tgtatgtgtg tgtatgtgta tttgtatatg tgtgcgtgta    2100
tgtgcatgtg tatttgtatg tgtgtgtgta tgtgtgtttg tgtctgtgtg tctgtgtgtg    2160
gtgtgtgtat atgtgcattt gtgtatatgt gtgtgtatgt gtgtgtgtct gtgtccatgt    2220
atgtgtgtgt gtgtacgtga gtacatttgt gtgcctgtgt gtgtatatgt gtgcacgtat    2280
gtgcatgtgt gtgtgtgtgc atatttgtgt gtgtatgtct gtgtccatgt gtctgcatat    2340
gtgtgtggtg tgtgtatatt tgtgtatgtt tacgtgtgtg tgtgtgtgtg cgcgcacgcg    2400
cgtggtgtag ggaaggaagg gccctgcctt cctcccttcc tggtccagtg tttctcccct    2460
cctgctctgg ctgaccctct aggttctgac tcctgcagtg tctgggctgg ggagagggcc    2520
cgtctcatgt gcccaccacc gctgtcatcc gggtactctc tggaccacgg atgttgaaag    2580
ccgacttatt ttcctgtggg tgctttccag aggttcctca gagagccccc cgtgagccct    2640
cccactgcac tttctgggat atggcagatg ctgcgtccct ttagctgctg tccccagccc    2700
ctggttctca gatggtcaac tccacaatct ctcgctgcta caaccctctg ggggtctcac    2760
agggcaggat tcagagcagt tccagtctgg cctcagagtg gtttcttctc ctcccaggaa    2820
gtccttgtgt tccttgccca ggcatgggcc agagtgcagc tcctcccaaa tgtggcccct    2880
gccctccttc tccatgccac aagttgctta agtttccctg agcatgcacc aggtgccagg    2940
cttgtgtctc tcacctgcag ggagctcatt ttaggggag aagggagaat acctctccct    3000
ttgatgcaca tggtagatgg agttctcaga tacagcaaga gctctcgcca gagaaatctt    3060
ttcacaaatt ctccctccat cccatcccag aagtggatgt gaagagtcca gaaagcaggt    3120
cccaggcctg gagtttccag tcatcggtaa attccaaagc tctggcccct tgctctggag    3180
taccagtcgt cggtaaattg gagtccccca atttaccggg agtcctccct ggactggagg    3240
taccagtcgt cggtaaattc caaagctctg gcccctggct ctggagtttc acatctcttg    3300
catctgttgt ctcctggtgt cgtggtcaaa gcttcagttt taatgtgcat ttccaattca    3360
ttctttcggt ctgtggtcca tcaggcaggc acttgcctta tgcccagcac agtttatttg    3420
ggaaagtcct gtccccttc cccctacaca cacactcagg cccagtacag cagtgctgtg    3480
ggtggttggg cctgtaagat ctgtaggggg cccaaggaaa gaagactccc tggggtagtt    3540
tcgagctctt gtcctgccct gcctgtccct tgggtgcccc gtgttggctg acatcgggaa    3600 tctgccctc ctgcag                                                     3616
```

<210> SEQ ID NO 122
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 122

Cys Ala Phe Glu Gly Glu Pro Ala Leu Ala Ser Asp Glu Leu Pro Pro
1               5                   10                  15

Ser Arg Asp Trp Arg
            20

<210> SEQ ID NO 123
<211> LENGTH: 19
<212> TYPE: DNA
<213> ORGANISM: Artificial Sequence

```
<220> FEATURE:
<223> OTHER INFORMATION: Synthetic Polynucleotide

<400> SEQUENCE: 123
gtgtgaacag acccacgat                                                    19

<210> SEQ ID NO 124
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 124
gtcgtacagc tccaccacaa                                                   20

<210> SEQ ID NO 125
<211> LENGTH: 41
<212> TYPE: DNA
<213> ORGANISM: Homo sapiens

<400> SEQUENCE: 125
ataactacat cccctgcacg ctggagcccg tatttggaaa g                            41

<210> SEQ ID NO 126
<211> LENGTH: 39
<212> TYPE: DNA
<213> ORGANISM: Homo sapiens

<400> SEQUENCE: 126
atgttcgagc tgacctgcac tctgcctctg gagaaggac                              39

<210> SEQ ID NO 127
<211> LENGTH: 59
<212> TYPE: PRT
<213> ORGANISM: Artificial Sequence
<220> FEATURE:
<223> OTHER INFORMATION: Synthetic Polypeptide

<400> SEQUENCE: 127

Arg His Leu Leu Phe Arg Cys His Gln Val Thr Tyr Cys Thr Tyr Lys
 1               5                  10                  15

Pro Gly Ser Val Glu Leu Val Val Val Thr His Pro Ala Val Arg Thr
            20                  25                  30

Gln Ser Pro Trp Gly Asn Ala Ala Phe Glu Gly Glu Pro Ala Leu Ala
        35                  40                  45

Ser Asp Glu Leu Pro Pro Ser Arg Asp Trp Arg
    50                  55

<210> SEQ ID NO 128
<211> LENGTH: 15
<212> TYPE: DNA
<213> ORGANISM: Homo sapiens

<400> SEQUENCE: 128
ttggagggaa gtggt                                                        15

<210> SEQ ID NO 129
<211> LENGTH: 12
<212> TYPE: DNA
<213> ORGANISM: Homo sapiens

<400> SEQUENCE: 129
```

```
tggaaagtaa at                                                          12

<210> SEQ ID NO 130
<211> LENGTH: 11
<212> TYPE: DNA
<213> ORGANISM: Artificial Sequence
<220> FEATURE:
<223> OTHER INFORMATION: Synthetic Polynucleotide

<400> SEQUENCE: 130
ttggaggtaa g                                                           11

<210> SEQ ID NO 131
<211> LENGTH: 12
<212> TYPE: DNA
<213> ORGANISM: Homo sapiens

<400> SEQUENCE: 131
ctgcaggatg tt                                                          12

<210> SEQ ID NO 132
<211> LENGTH: 67
<212> TYPE: DNA
<213> ORGANISM: Artificial Sequence
<220> FEATURE:
<223> OTHER INFORMATION: Synthetic Polynucleotide

<400> SEQUENCE: 132
ttaggccaga gagggagga tgcagaggga gggtggcagc tatttctctc gcacctgcag       60
aagacac                                                                67

<210> SEQ ID NO 133
<211> LENGTH: 51
<212> TYPE: PRT
<213> ORGANISM: Homo sapiens

<400> SEQUENCE: 133

Leu Val Arg Ile Tyr Ile Val Arg Ala Phe Gly Leu Gln Pro Lys Asp
1               5                   10                  15

Pro Asn Gly Lys Cys Asp Pro Tyr Ile Lys Ile Ser Ile Gly Lys Lys
            20                  25                  30

Ser Val Ser Asp Gln Asp Asn Tyr Ile Pro Cys Thr Leu Glu Pro Val
        35                  40                  45

Phe Gly Lys
    50

<210> SEQ ID NO 134
<211> LENGTH: 33
<212> TYPE: PRT
<213> ORGANISM: Homo sapiens

<400> SEQUENCE: 134

Met Phe Glu Leu Thr Cys Thr Leu Pro Leu Glu Lys Asp Leu Lys Ile
1               5                   10                  15

Thr Leu Tyr Asp Tyr Asp Leu Leu Ser Lys Asp Glu Lys Ile Gly Glu
            20                  25                  30

Thr
```